United States Patent
Avery et al.

(10) Patent No.: US 10,598,614 B2
(45) Date of Patent: Mar. 24, 2020

(54) METHODS OF PREPARING SINGLE-WALLED CARBON NANOTUBE NETWORKS

(71) Applicant: Alliance for Sustainable Energy, LLC, Golden, CO (US)

(72) Inventors: Azure Dee Avery, Denver, CO (US); Jeffrey Lee Blackburn, Golden, CO (US); Andrew John Ferguson, Louisville, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 187 days.

(21) Appl. No.: 15/741,895

(22) PCT Filed: Jul. 13, 2016

(86) PCT No.: PCT/US2016/042085
§ 371 (c)(1),
(2) Date: Jan. 4, 2018

(87) PCT Pub. No.: WO2017/011551
PCT Pub. Date: Jan. 19, 2017

(65) Prior Publication Data
US 2018/0194629 A1    Jul. 12, 2018

Related U.S. Application Data

(60) Provisional application No. 62/191,911, filed on Jul. 13, 2015, provisional application No. 62/211,064, (Continued)

(51) Int. Cl.
*G01N 23/20* (2018.01)
*H01L 35/22* (2006.01)
(Continued)

(52) U.S. Cl.
CPC ........... *G01N 23/20* (2013.01); *C01B 32/168* (2017.08); *G01N 21/62* (2013.01); *H01L 27/16* (2013.01);
(Continued)

(58) Field of Classification Search
CPC ... C01B 10/168; C01B 32/159; H01L 51/002; H01L 51/0048; H01L 27/16; H01L 35/22;
(Continued)

(56) References Cited

U.S. PATENT DOCUMENTS

| 2012/0052308 A1 | 3/2012 | El-Ashry et al. |
| 2012/0070612 A1 | 3/2012 | Lee et al. |

(Continued)

FOREIGN PATENT DOCUMENTS

| EP | 2 763 200 A1 | 6/2014 |
| WO | WO 2012/054504 A2 | 4/2012 |

OTHER PUBLICATIONS

Chien, Chia-Ling, et al. Novel Syntheses of Thermoelectric and Nanostructured Materials and a System for Purifying and Sorting Metallic and Semiconducting Single Walled Carbon Nanotubes in a Mixed Tube Suspension. Diss. Johns Hopkins University, 2014.*

(Continued)

*Primary Examiner* — Richard M Rump
(74) *Attorney, Agent, or Firm* — Michael A. McIntyre

(57) ABSTRACT

Methods for determining desired doping conditions for a semiconducting single-walled carbon nanotube (s-SWCNT) are provided. One exemplary method includes doping each of a plurality of s-SWCNT networks under a respective set of doping conditions; determining a thermoelectric (TE) power factor as a function of a fractional bleach of an absorption spectrum for the plurality of s-SWCNT networks doped under the respective sets of doping conditions; and using the function to identify one of the TE power factors (Continued)

within a range of the fractional bleach of the absorption spectrum. The identified TE power factor corresponds to the desired doping conditions.

10 Claims, 72 Drawing Sheets

Related U.S. Application Data filed on Aug. 28, 2015, provisional application No. 62/316,709, filed on Apr. 1, 2016.

(51) Int. Cl.
```
H01L 51/00      (2006.01)
G01N 21/62      (2006.01)
C01B 32/168     (2017.01)
H01L 27/16      (2006.01)
B82Y 30/00      (2011.01)
B82Y 40/00      (2011.01)
G01N 15/00      (2006.01)
```
(52) U.S. Cl.
CPC ............ *H01L 35/22* (2013.01); *H01L 51/002* (2013.01); *H01L 51/0048* (2013.01); *B82Y 30/00* (2013.01); *B82Y 40/00* (2013.01); *G01N 2015/0038* (2013.01)

(58) Field of Classification Search
CPC ........ B82Y 30/00; B82Y 40/00; G01N 23/20; G01N 2015/0038
See application file for complete search history.

(56) References Cited

U.S. PATENT DOCUMENTS

| | | |
|---|---|---|
| 2013/0312806 A1 | 11/2013 | Carroll |
| 2014/0230871 A1 | 8/2014 | Nishio et al. |

OTHER PUBLICATIONS

Arnold, M. et al., "Sorting carbon nanotubes by electronic structure using density differentiation," Nature Nanotechnology, vol. 1, 2006, pp. 60-65.

Avery, A. et al., "Thermal and electrical conductivity of approximately 100-nm permalloy, Ni, Co, Al, and Cu films and examination of the Wiedemann-Franz Law," Physical Review B, vol. 92, 2015, pp. 214410 through 214410-10.

Avery, A. et al., "Tunable Thermoelectric Power Factor in Semiconducting Single-Walled Carbon Nanotube Networks," Jan. 2015, retrieved on Sep. 13, 2016, http://thermosymposium.nist.gov/ pdf/abstract_3353.pdf, one page.

Avery, A. et al., "Tailored semiconducting carbon nanotube networks with enhanced thermoelectric properties," Nature Energy, vol. 1, 2016, pp. 1-9.

Barnes, T. et al., "Reversibility, Dopant Desorption, and Tunneling in the Temperature-Dependent Conductivity of Type-Separated, Conductive Carbon Nanotube Networks," ACS Nano, vol. 2, No. 9, 2008, pp. 1968-1976.

Bindl, D. et al., "Enhancing extraction of photogenerated excitons from semiconducting carbon nanotube films as photocurrent," Chemical Physics, vol. 413, 2013, pp. 29-34.

Bindl, D. et al., "Free Carrier Generation and Recombination in Polymere-Wrapped Semiconducting Carbon Nanotube Films and Heterojunctions," Journal of Physical Chemistry Letters, vol. 4, 2013, pp. 3550-3559.

Blackburn, J. et al., "Synthesis and Characterization of Boron-Doped Single-Wall Carbon Nanotubes Produced by the Laser Vaporization Technique," Chemical Materials, vol. 18, 2006, pp. 2558-2566.

Blackburn, J. et al., "Transparent Conductive Single-Walled Carbon Nanotube Networks with Precisely Tunable Ratios of Semiconducting and Metallic Nanotubes," ACS Nano, vol. 2, No. 6, 2008, pp. 1266-1274.

Brady, G. et al., "High performance transistors via aligned polyfluorene-sorted carbon nanotubes," Applied Physics Letters, vol. 104, 2014, pp. 083107-1 through 083107-5.

Brady, G. et al., "Polyfluorene-Sorted, Carbon Nanotube Array Field-Effect Transistors with Increased Current Density and High On/Off Ratio," ACS Nano, vol. 8, No. 11, 2014, pp. 11614-11621.

Bubnova, O. et al., "Optimization of the thermoelectric figure of merit in the conducting polymer poly (3,4-ethylenedioxythiophene)," Nature Materials, vol. 10, Jun. 2011, pp. 429-433.

Bubnova, O. et al., "Semi-metallic polymers," Nature Materials, vol. 13, 2014, pp. 190-194.

Capaz, R. et al., "Excitons in carbon nanotubes: Diameter and chirality trends," Phys. Stat. Sol. (b), vol. 244, No. 11, 2007, pp. 4016-4020.

Casian, A. et al., "Modeling of the Thermoelectric Power Factor in Quasi-One-Dimensional Organic Crystals," 2006 IEEE International Conference on Thermoelectrics, 4 pages.

Chandra, B. et al., "Stable Charge-Transfer Doping of Transparent Single-Walled Carbon Nanotube Films," Chemistry of Materials, vol. 22, 2010, pp. 5179-5183.

Chang, K. et al., "The Thermoelectric Performance of Poly(3,4-ethylenedioxythiophene)/Poly(4-styrenesulfonate) Thin Films," Journal of the Electronic Materials, vol. 38, No. 7, 2009, pp. 1182-1188.

Cho, C. et al., "Completely Organic Multilayer Thin Film with Thermoelectric Power Factor Rivaling Inorganic Tellurides," Advanced Materials, vol. 27, 2015, pp. 2996-3001.

Dillon, A. et al., "A Simple and Complete Purification of Single-Walled Carbon Nanotube Materials," Advanced Materials, vol. 11, No. 16, 1999, pp. 1354-1358.

Dowgiallo, A. et al., "Ultrafast Spectroscopic Signature of Charge Transfer between Single-Walled Carbon Nanotubes and $C_{60}$," ACS NANO, vol. 8, No. 8, 2014, pp. 8573-8581.

Dubey, N. et al., "Conducting Polymers: Efficient Thermoelectric Materials," Journal of Polymer Science Part B: Polymer Physics, 2011, vol. 49, pp. 467-475.

Engtrakul, C. et al., "Solid-State C NMR Assignment of Carbon Resonances on Metallic and Semiconducting Single-Walled Carbon Nanotubes," Journal of the American Chemical Society, vol. 132, 2010, pp. 9956-9957.

Fagan, J. et al., "Isolation of >1 nm Diameter Single-Wall Carbon Nanotube Species Using Aqueous Two-Phase Extraction," ACS Nano, vol. 9, No. 5, 2015, pp. 5377-5390.

Ferguson, A. et al., "Photoinduced Energy and Charge Transfer in P3HT:SWNT Composites," Journal of Physical Chemistry Letters, vol. 1, 2010, pp. 2406-2411.

Glaudell, A. et al., "Impact of the Doping Method on Conductivity and Thermopower in Semiconducting Polythiophenes," Advanced Energy Materials, vol. 5, 2015, 8 pages.

Gui, H. et al., "Redox Sorting of Carbon Nanotubes," Nano Letters, vol. 15, 2015, pp. 1642-1646.

Guillot, S. et al., "Precision printing and optical modeling of ultrathin SWCNT/$C_{60}$ heterojunction solar cells," Nanoscale, vol. 7, 2015, pp. 6556-6566.

Hewitt, C. et al., "Varying the concentration of single walled carbon nanotubes in thin film polymer composites, and its effect on thermoelectric power," Applied Physics Letters, vol. 98, pp. 183110 through 183110-3.

Hewitt, C. et al., "Multilayered Carbon Nanotube/Polymer Composite Based Thermoelectric Fabrics," Nano Letters, vol. 12, 2012, pp. 1307-1310.

Hicks, L. et al., "Effect of quantum-well structures on the thermoelectric figure of merit," Physical Review B, vol. 47, No. 19, 1993, pp. 12727 through 12731.

Hicks, L. et al., "Thermoelectric figure of merit of a one-dimensional conductor," Physical Review B, vol. 47, No. 24, 1993, pp. 16631 through 16634.

Hochbaum, A. et al., "Enhanced thermoelectric performance of rough silicon nanowires," Nature Letters, vol. 451, 2008, pp. 163-168.

(56) References Cited

OTHER PUBLICATIONS

Hone, J. et al., "Thermal conductivity of single-walled carbon nanotubes," Physical Review B, vol. 59, No. 4, 1999, pp. R2514 through R2516.
Itkis, M. et al., "Networks of Semiconducting SWNTs: Contribution of Midgap Electronic States to the Electrical Transport," vol. 48, 2015, pp. 2270-2279.
Janietz, S. et al., "Electrochemical determination of the ionization potential and electron affinity of poly(9,9-dioctylfluorene)," Applied Physics Letters, vol. 73, No. 17, 1998, pp. 2453-2455.
Jensen, B.W. et al., "Vapor-Phase Polymerization of 3,4-Ethylenedioxythiophene: A Route to Highly Conducting Polymer Surface Layers," Macromolecules, vol. 37, 2004, pp. 4538-4543.
Kaiser, A., "Electronic transport properties of conducting polymers and carbon nanotubes," Institute of Physics Publishing, Reports on Progress in Physics, vol. 64, 2001, pp. 1-49.
Kaiser, A. et al., "Electronic conduction in polymers, carbon nanotubes and graphene," Royal Society of Chemistry, Chem. Soc. Rev., vol. 40, 2011, pp. 3786-3801.
Kim, D. et al., "Improved Thermoelectric Behavior of Nanotube-Filled Polymer Composites with Poly(3,4-ethylenedioxythiophene)Poly(styrenesulfonate), ACS Nano, vol. 4, No. 1, 2010, pp. 513-523.
Kim, G., "Thermoelectric transport in organic materials," Dissertation, University of Michigan, 2013, accessed at https://deepblue.lib.umich.edu/handle/2027.42/102350, 14 pages.
Kim, G-H et al., "Engineered doping of organic semiconductors for enhanced thermoelectric efficiency," vol. 12, 2013, pp. 719-723.
Kymakis, E. et al., "Electrical properties of single-wall carbon nanotube-polymer composite films," Journal of Applied Physics, vol. 99, 2006, pp. 084307 through 084302-7.
Liang, Z. et al., "Defect Engineering in π-Conjugated Polymers," Chemistry of Materials, vol. 21, 2009, pp. 4914-4919.
Mistry, K. et al., "n-Type Transparent Conducting Films of Small Molecule and Polymer Amine Doped Single-Walled Carbon Nanotubes," ACS Nano, vol. 5, No. 5, 2011, pp. 3714-3723.
Mistry, K. et al., "High-Yield Dispersions of Large-Diameter Semiconducting Single-Walled Carbon Nanotubes with Tunable Narrow Chirallity Distributions," ACS Nano, vol. 7, No. 3, 2013, pp. 2231-2239.
Mistry, Kevin S., "Investigating Charge Generation and Mobility in Type-Separated Single-Walled Carbon Nanotube Ensembles for Solar Photovoltaics," Dissertation, University of Colorado, retrieved on Sep. 13, 2016, http://scholar.colorado.edu/cgi/viewcontent.cgi?article=1002&context=phys_gradetds, 164 pages.
Nakai, Y. et al., "Giant Seebeck coefficient in semiconducting single-wall carbon nanotube film," Applied Physics Express, vol. 7, 2014, pp. 025103-1 through 025103-4.
Nardes, A.M. et al., "Conductivity, work function, and environmental stability of PEDOT:PSS thin films treated with sorbitol," Organic Electronics, vol. 9, 2008, pp. 727-734.
Nardes, A.M. et al., "A Morphological Model for the Solvent-Enhanced Conductivity of PEDOT:PSS Thin Films," Advanced Functional Materials, vol. 18, 2008, pp. 865-871.
Nardes, A.M. et al., "Anisotropic hopping conduction in spin-coated PEDOT:PSS thin films," Physical Review B, vol. 76, 2007, pp. 085208-1 through 085208-7.
Nardes, A.M. et al., "Microscopic Understanding of the Anisotropic Conductivity of PEDOT:PSS Thin Films," Advanced Materials, vol. 19, 2007, pp. 1196-1200.
Nish, A. et al., "Highly selective dispersion of single-walled carbon nanotubes using aromatic polymers," Nature Nanotechnology, vol. 2, 2007, pp. 640-646.
Parker, W. et al., "Flash Method of Determining Thermal Diffusivity, Heat Capacity, and Thermal Conductivity," Journal of Applied Physics, vol. 32, No. 9, 1961, pp. 1679-1684.
Pochorovski, I. et al., "H-Bonded Supramolecular Polymer for the Selective Dispersion and Subsequent Release of Large-Diameter Semiconducting Single-Walled Carbon Nanotubes," Journal of the American Chemical Society, vol. 137, 2015, pp. 4328-4331.
Piao, M. et al., "Effect of Intertube Junctions on the Thermoelectric Power of Monodispersed Single Walled Carbon Nanotube Networks," Journal of Physical Chemistry C, vol. 118, 2014, 26454-26461.
Pop, E. et al., "Thermal Conductance of an Individual Single-Wall Carbon Nanotube above Room Temperature," Nano Letters, vol. 6, No. 1, 2006, pp. 96-100.
Prasher, R. et al., "Turning Carbon Nanotubes from Exceptional Heat Conductors into Insulators," Physical Review Letters, vol. 102, 2009, pp. 105901-105901-4.
Rivadulla, F. et al., "Layer-by-Layer Polymer Coating of Carbon Nanotubes: Tuning of Electrical Conductivity in Random Networks," Journal of the American Chemical Society, vol. 132, 2010, pp. 3751-3755.
Russ, B. et al., "Power Factor Enhancement in Solution-Processed Organic n-Type Thermoelectrics Through Molecular Design," Advanced Materials, vol. 26, 2014, pp. 3473-3477.
Schuettfort, T. et al., "Observation of a Type II Heterojunction in a Highly Ordered Polymer-Carbon Nanotube Nanohybrid Structure," Nano Letters, vol. 9, No. 11, 2009, pp. 3871-3876.
See, K. et al., "Water-Processable Polymer-Nanocrystal Hybrids for Thermoelectrics," Nano Letters, vol. 10, 2010, pp. 4664-4667.
Snyder, G. et al., "Complex thermoelectric materials," Nature Materials, vol. 7, 2008, pp. 105-114.
Stedman, T. et al., "Thermoelectricity in polymer composites due to fluctuation-induced tunneling," Phys. Chem. Chem. Phys., vol. 17, 2015, pp. 27883-27888.
Sultan, R. et al., "Thermal conductivity of micromachined low-stress silicon-nitride beams from 77 to 325 K," Journal of Applied Physics, vol. 105, 2009, pp. 043501-1 through 043501-7.
Tenent, R. et al., "Ultrasmooth, Large-Area, High-Uniformity, Conductive Transparent Single-Walled-Carbon-Nanotube Films for Photovoltaics Produced by Ultrasonic Spraying," Advanced Materials, vol. 21, 2009, pp. 3210-3216.
Tu, X. et al., "DNA sequence motifs for structure-specific recognition and separation of carbon nanotubes," Nature Letters, vol. 460, 2009, pp. 250-253.
Wang, Y. et al., "Thermoelectric Properties of Molecular Nanowires," Journal of Physical Chemistry C, vol. 115, 2011, pp. 24418-24428.
Wang, D. et al., "Treating Poly(3-hexylthiophene) with Dimethylsulfate Improves Its Photoelectrical Properties," Chemical Materials, vol. 20, 2008, pp. 6307-6309.
Weisman, R. et al., "Dependence of Optical Transition Energies on Structure for Single-Walled Carbon Nanotubes in Aqueous Suspension: An Empirical Kataura Plot," Nano Letters, vol. 3, No. 9, 2003, pp. 1235-1238.
Yu, C. et al., "Thermoelectric Behavior of Segregated-Network Polymer Nanocomposites," Nano Letters, vol. 8, No. 12, 2008, pp. 4428-4432.
Yu, C., "Thermal Conductance and Thermopower of an Individual Single-Wall Carbon Nanotube," Nano Letters, vol. 5, No. 9, 2005, pp. 1842-1846.
Yu, C. "Light-Weight Flexible Carbon Nanotube Based Organic Composites with Large Thermoelectric Power Factors," ACS Nano, vol. 5, No. 10, 2011, pp. 7885-7892.
Zhang, G. et al., "Impacts of doping on thermal and thermoelectric properties of nanomaterials," Nanoscale, vol. 2, 2010, pp. 1058-1068.
Zheng, M. et al., "Structure-Based Carbon Nanotube Sorting by Sequence-Dependent DNA Assembly," Science, vol. 302, 2003, pp. 1545-1548.
Search Report from corresponding PCT application No. PCT/US16/42085 dated Nov. 18, 2016, 4 pages.
Written Opinion from corresponding PCT application No. PCT/US16/42085 dated Nov. 18, 2016, 6 pages.
Avery, A. et al., "Tunable Thermoelectric Power Factor in Semiconducting Single-Walled Carbon Nanotube Networks," Jan. 2015, retrieved on Feb. 16, 2017, http://thermosymposium.nist.gov/pdf/abstract_3353.pdf, one page.
Supplementary European Search Report from corresponding European patent application EP 16 82 5108 dated Feb. 8, 2019, 8 pages.

* cited by examiner

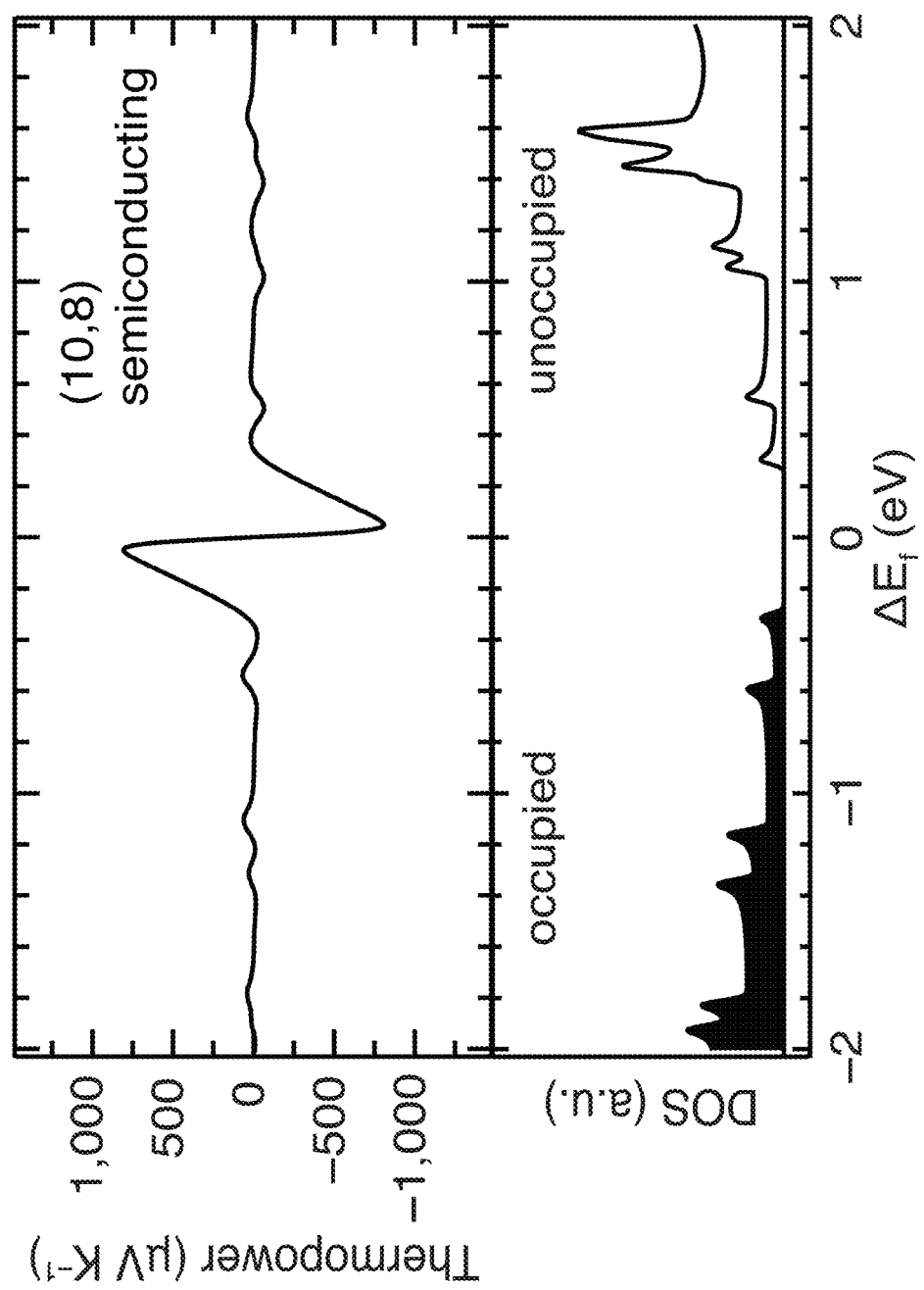

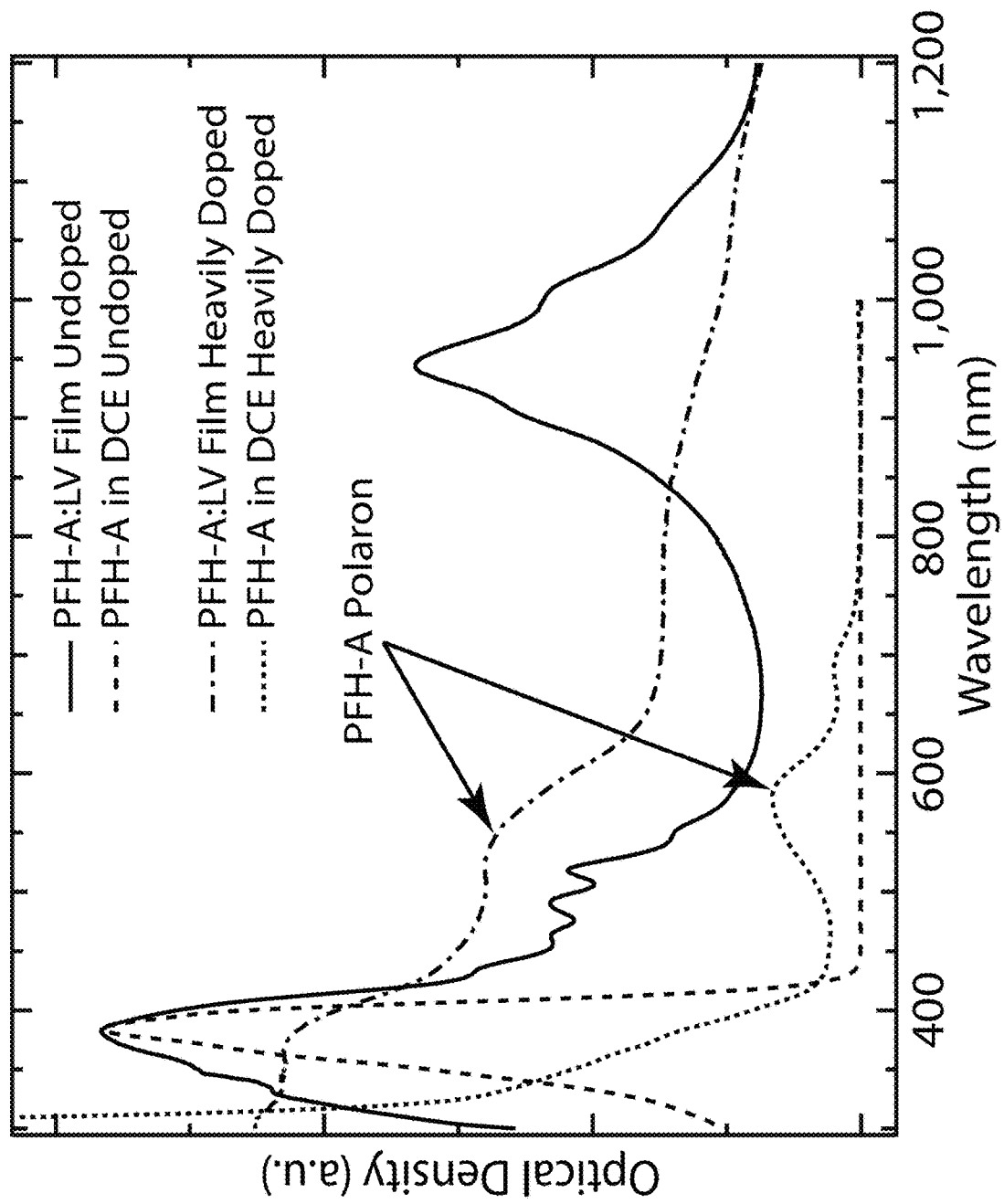

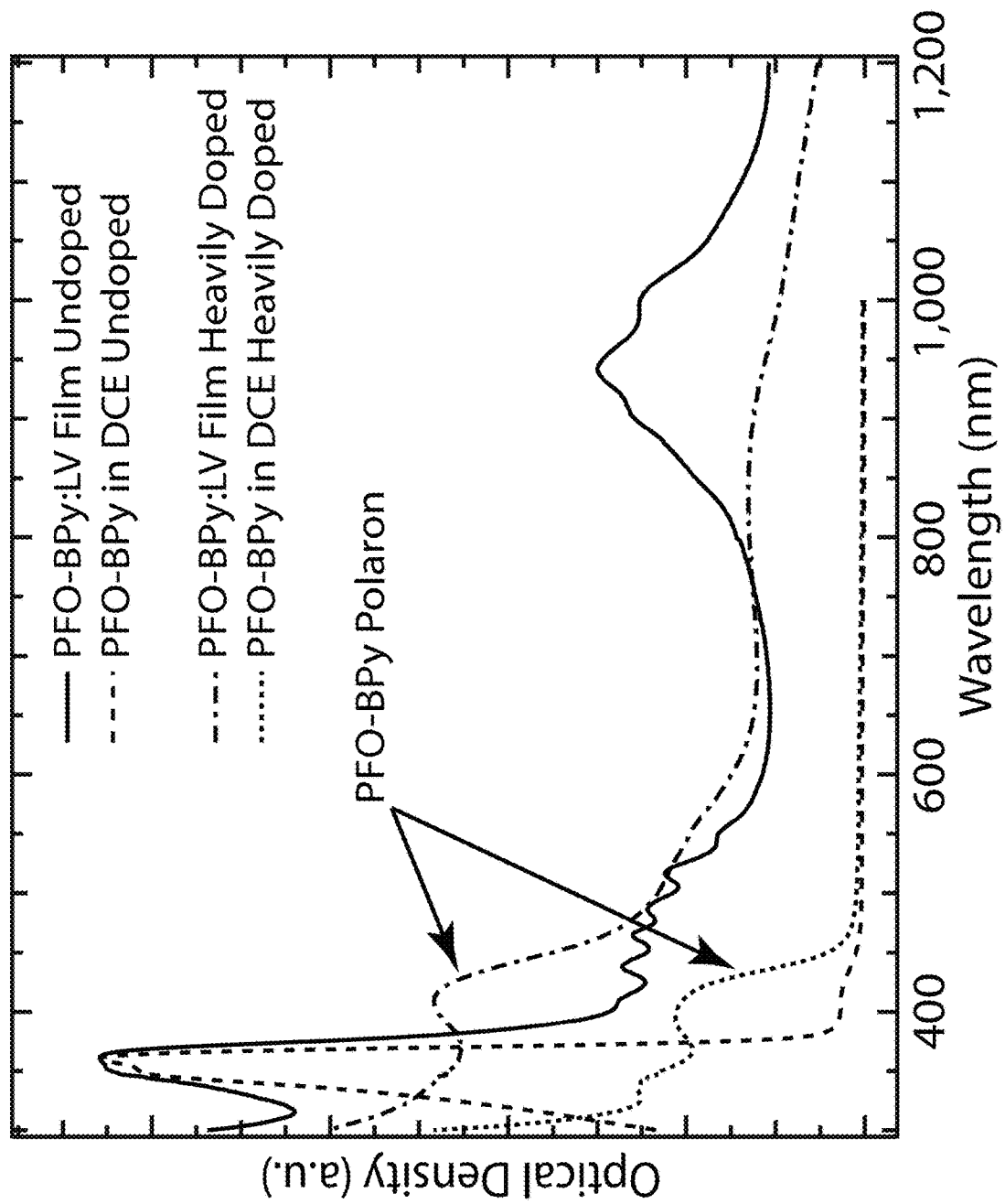

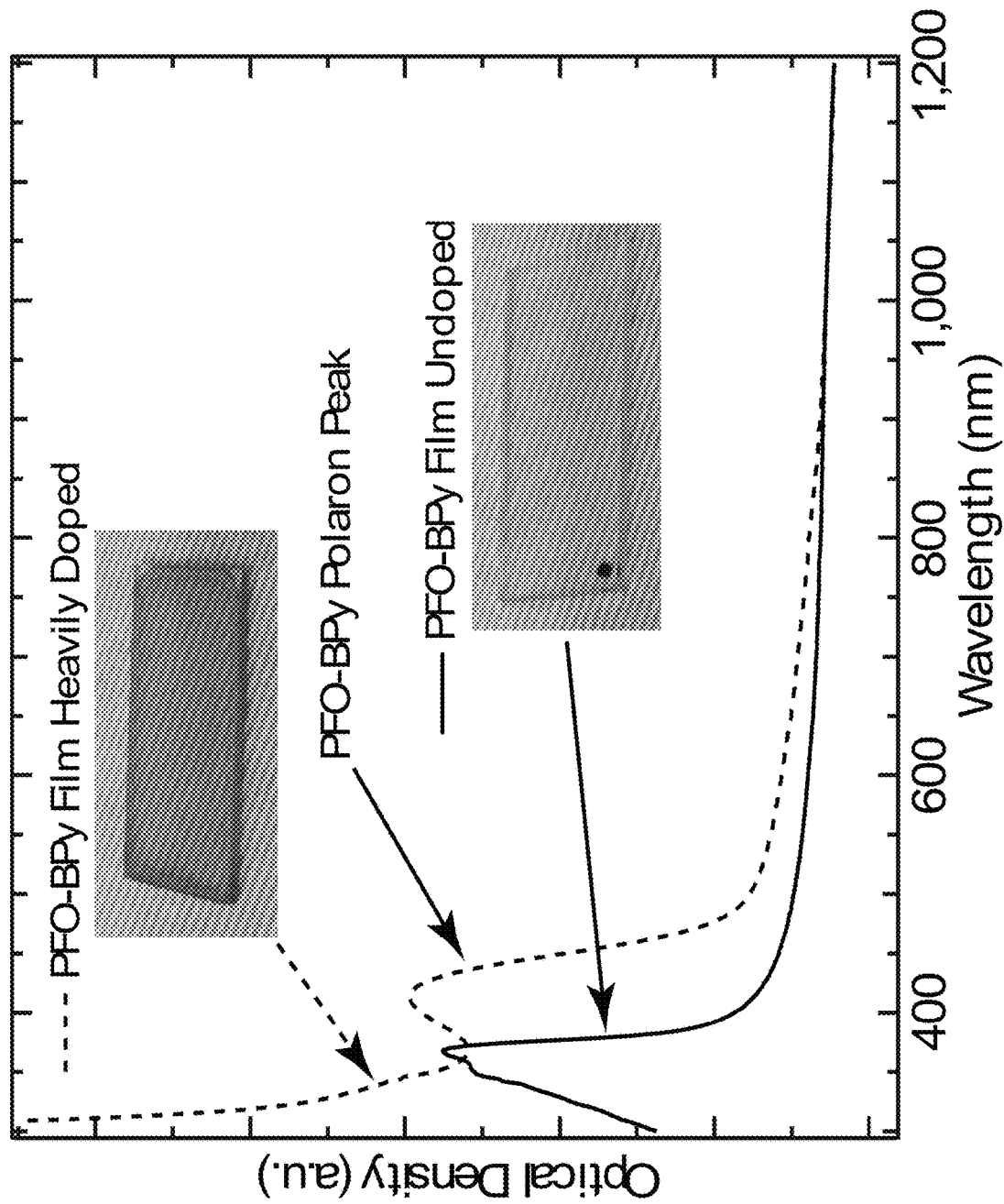

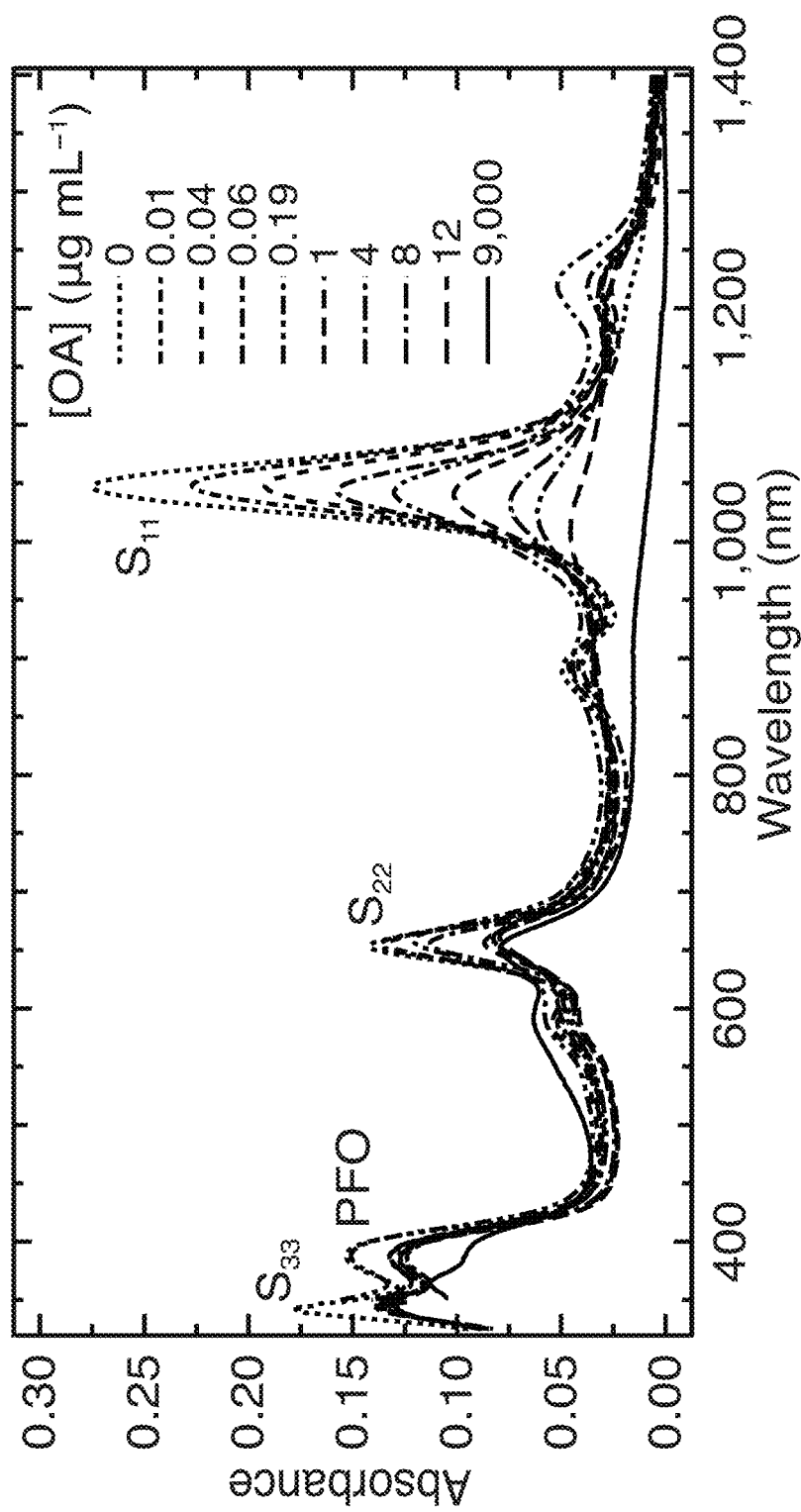

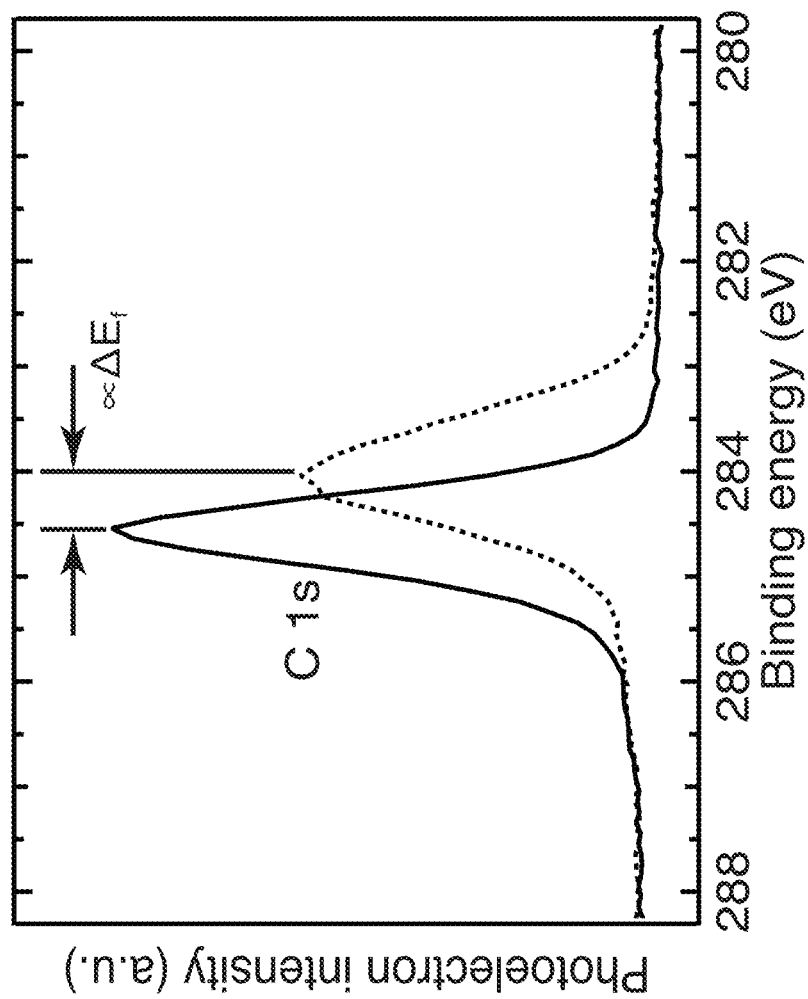

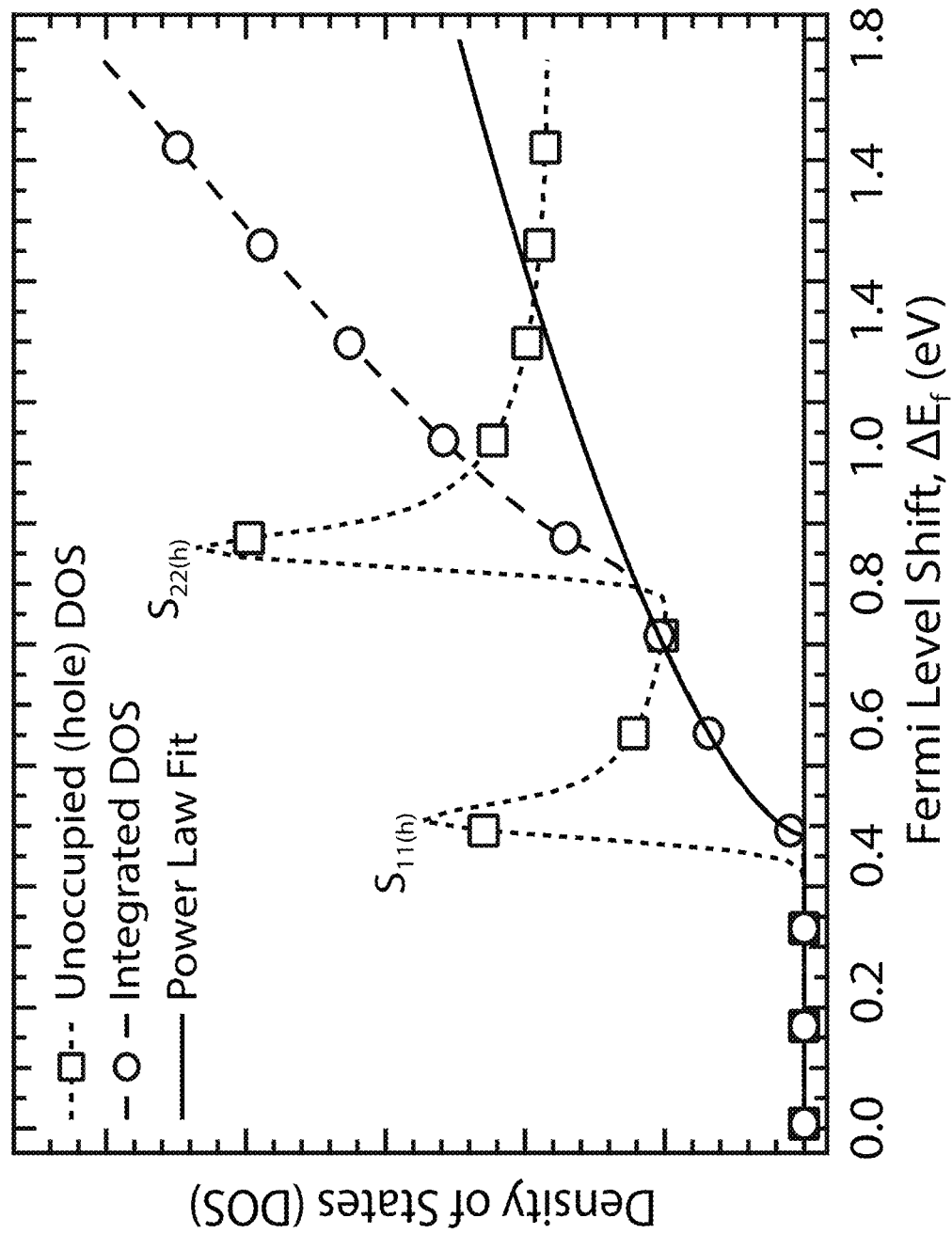

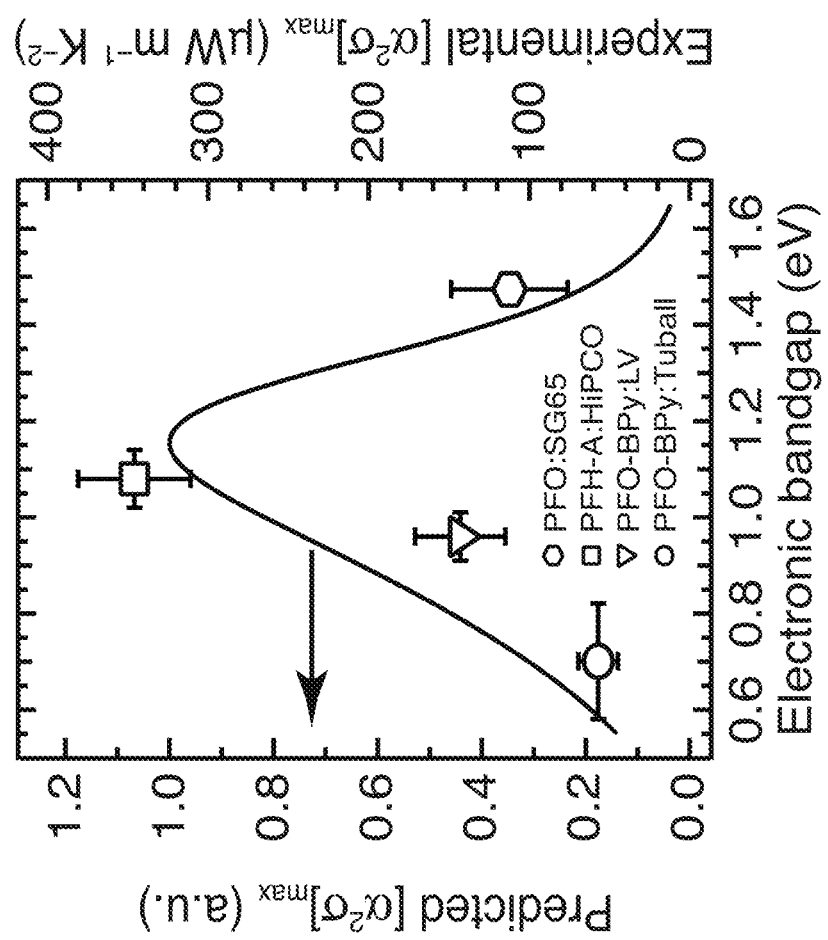

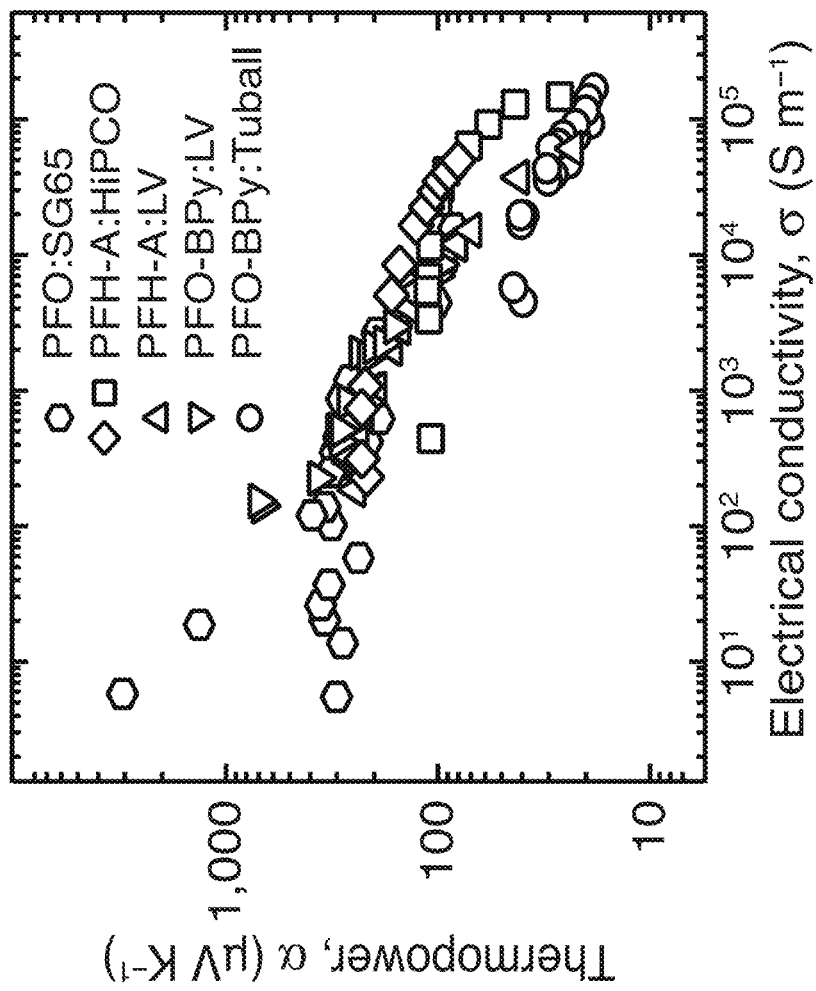

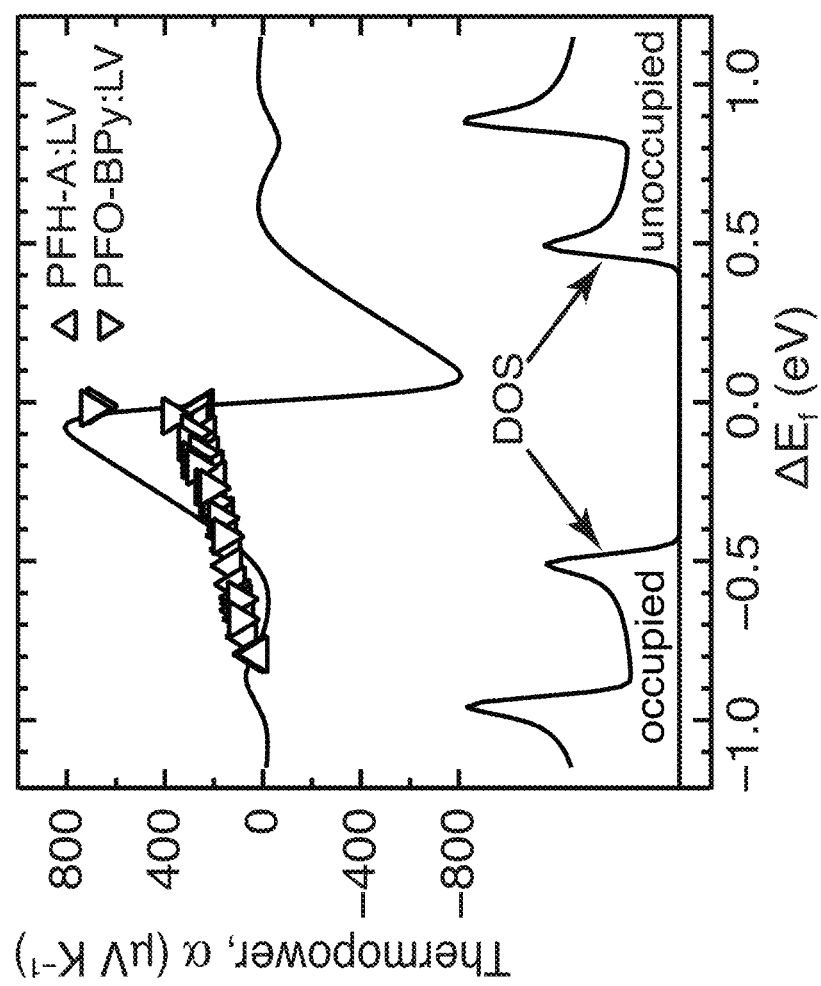

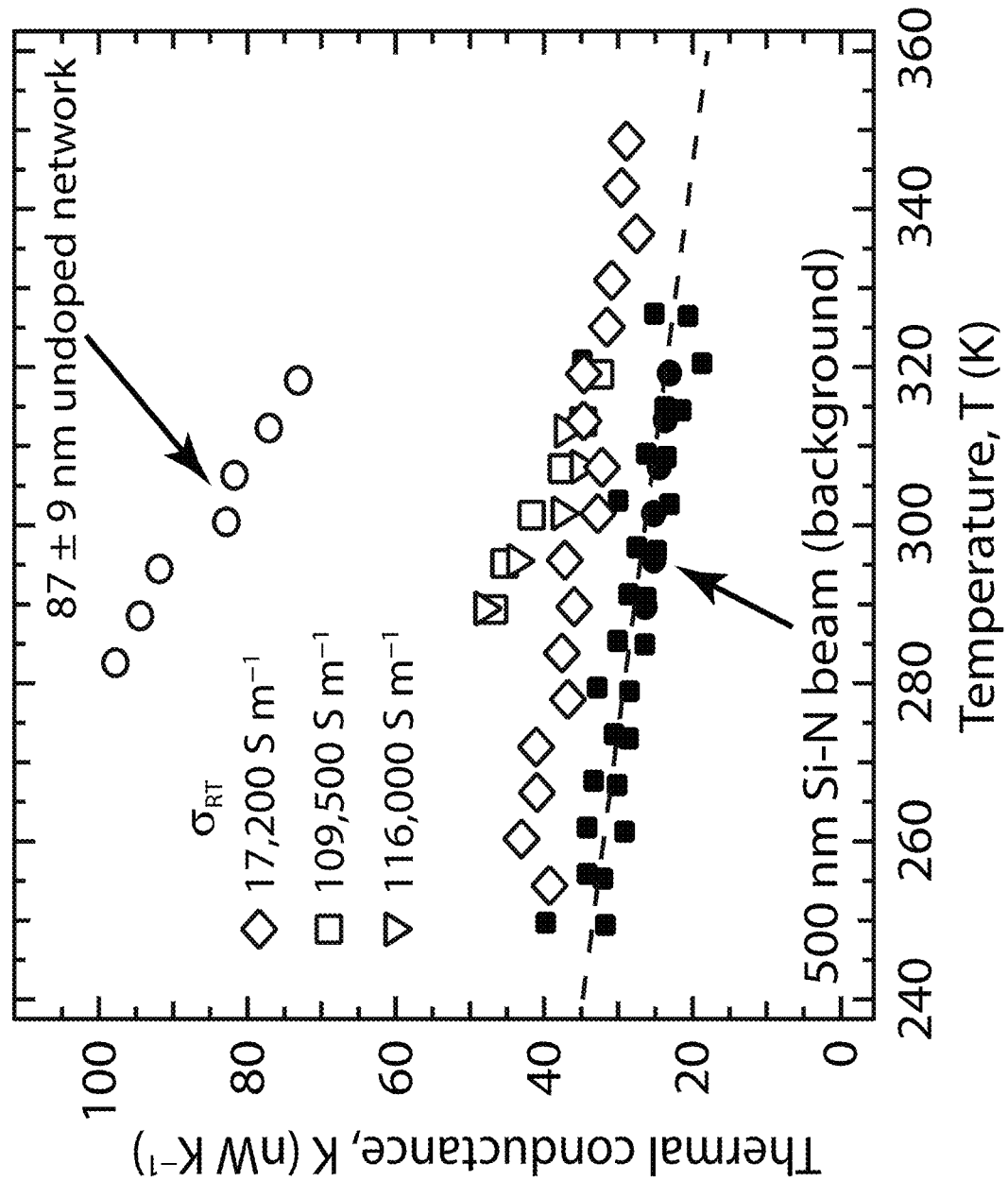

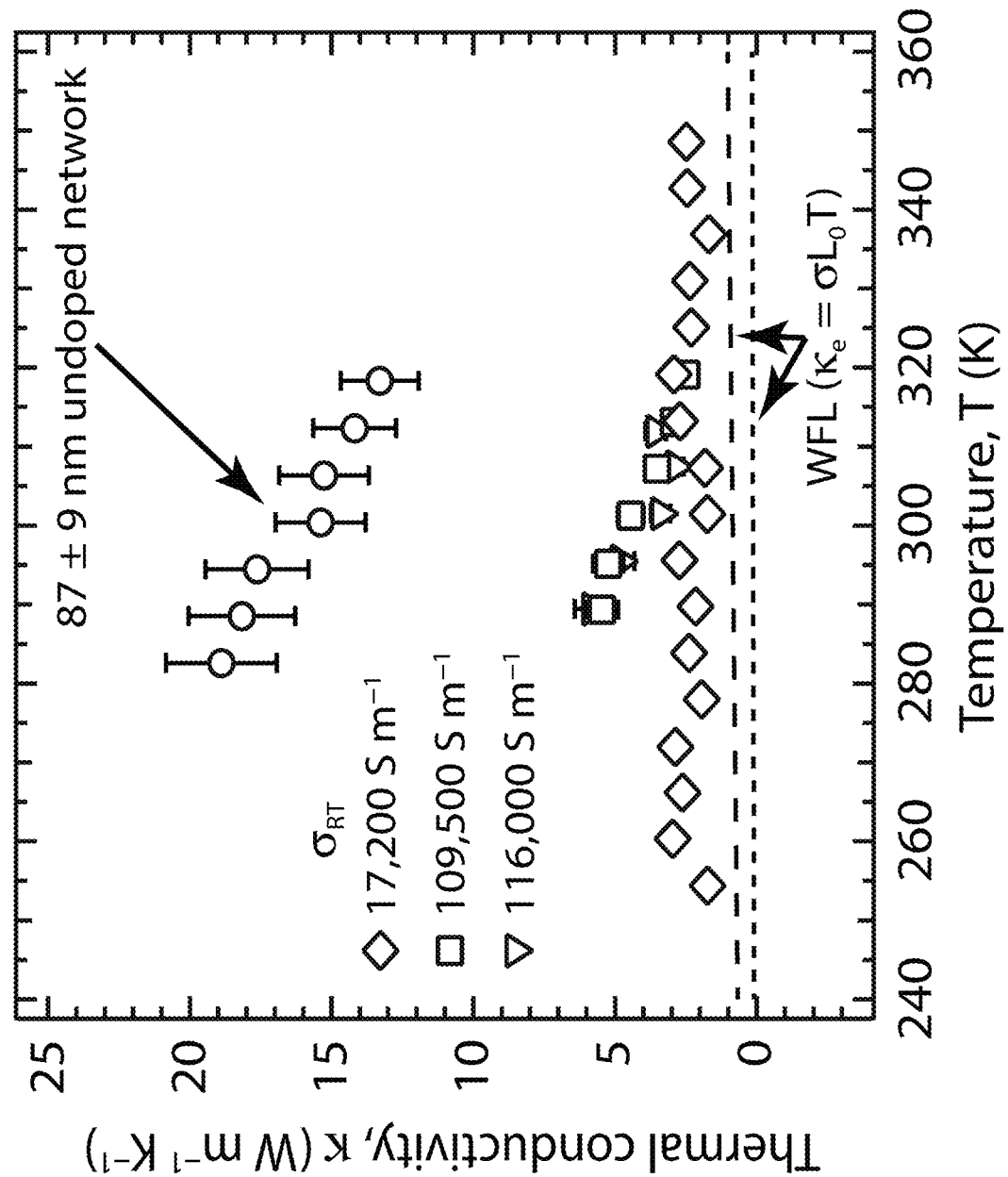

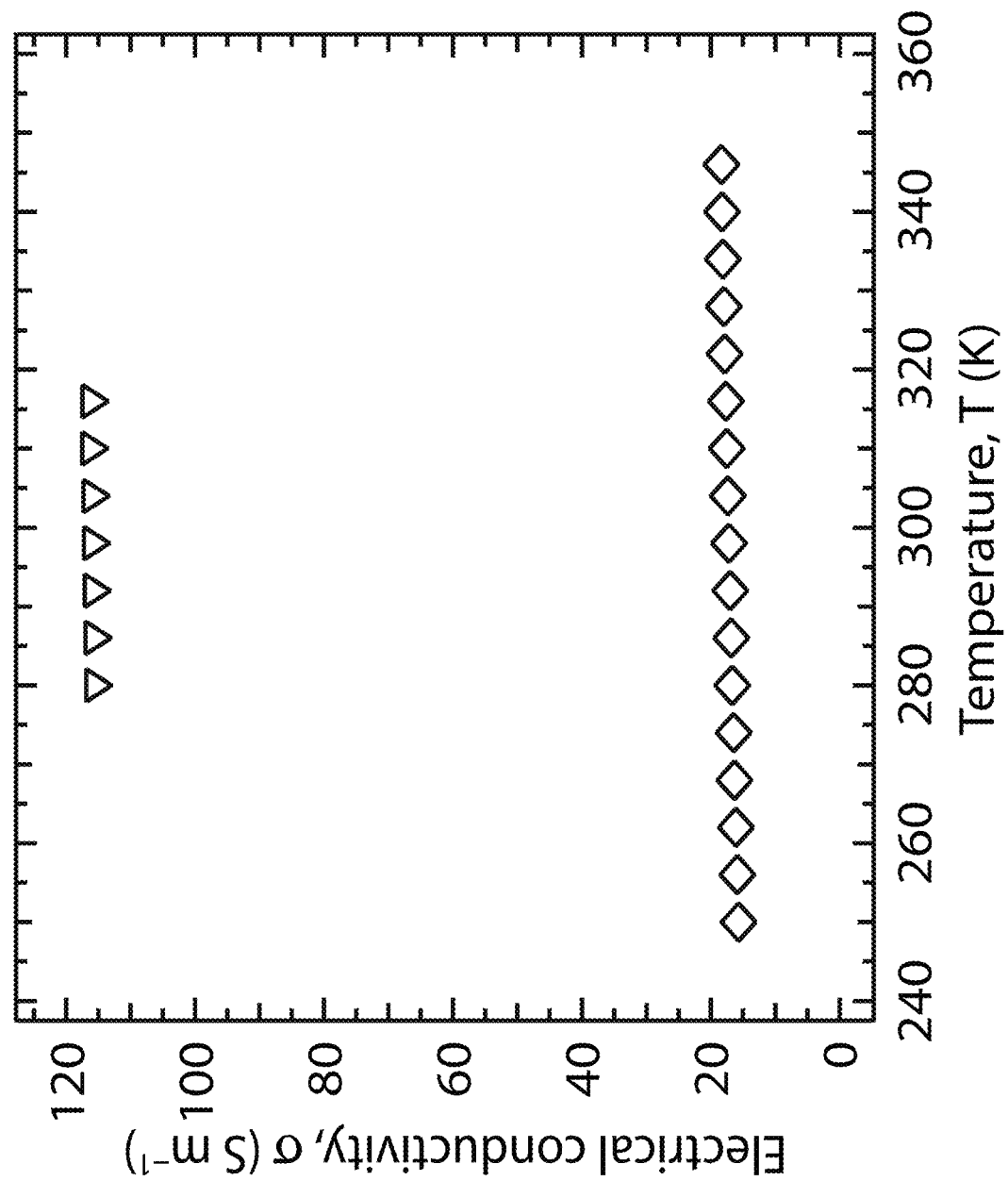

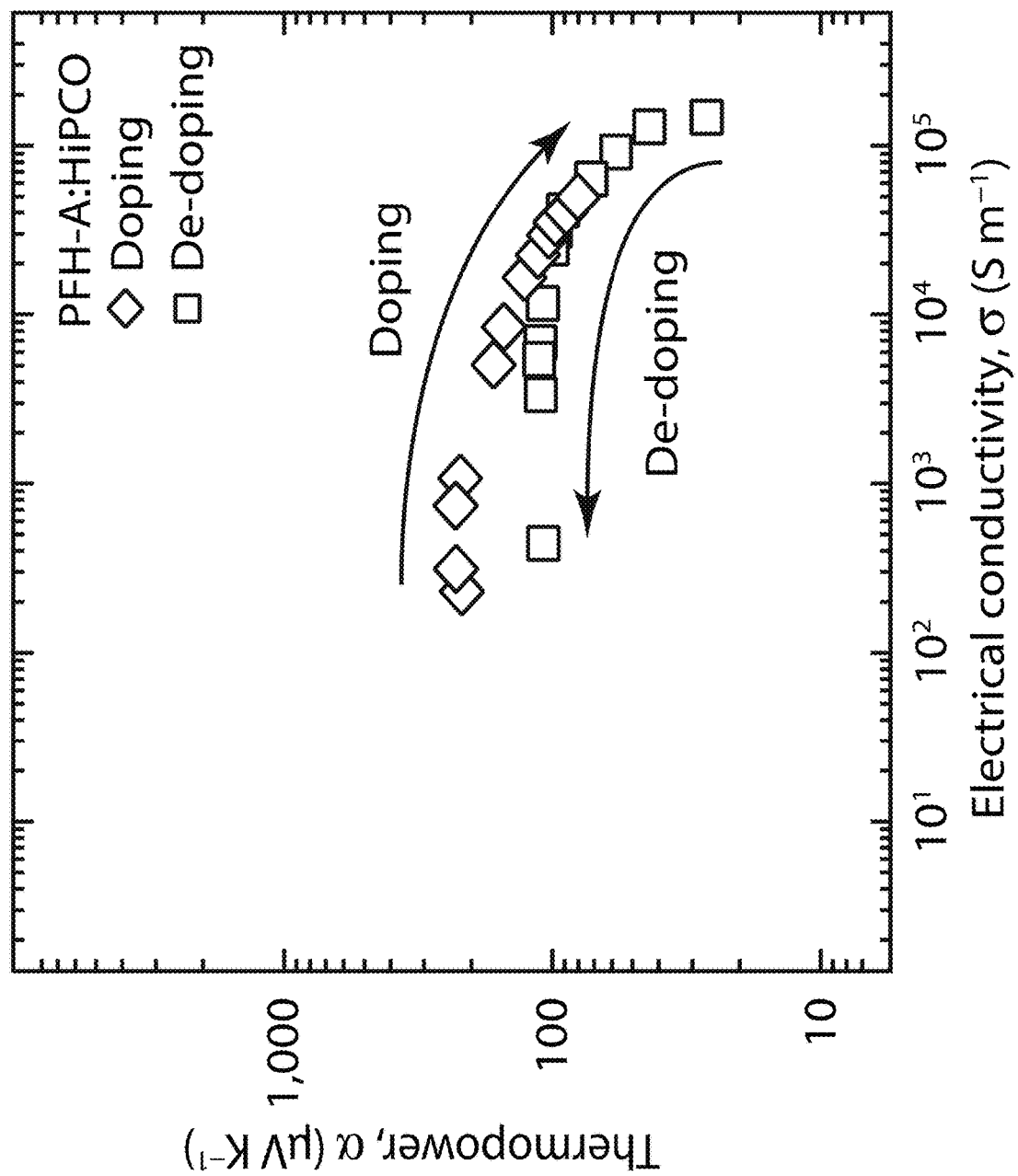

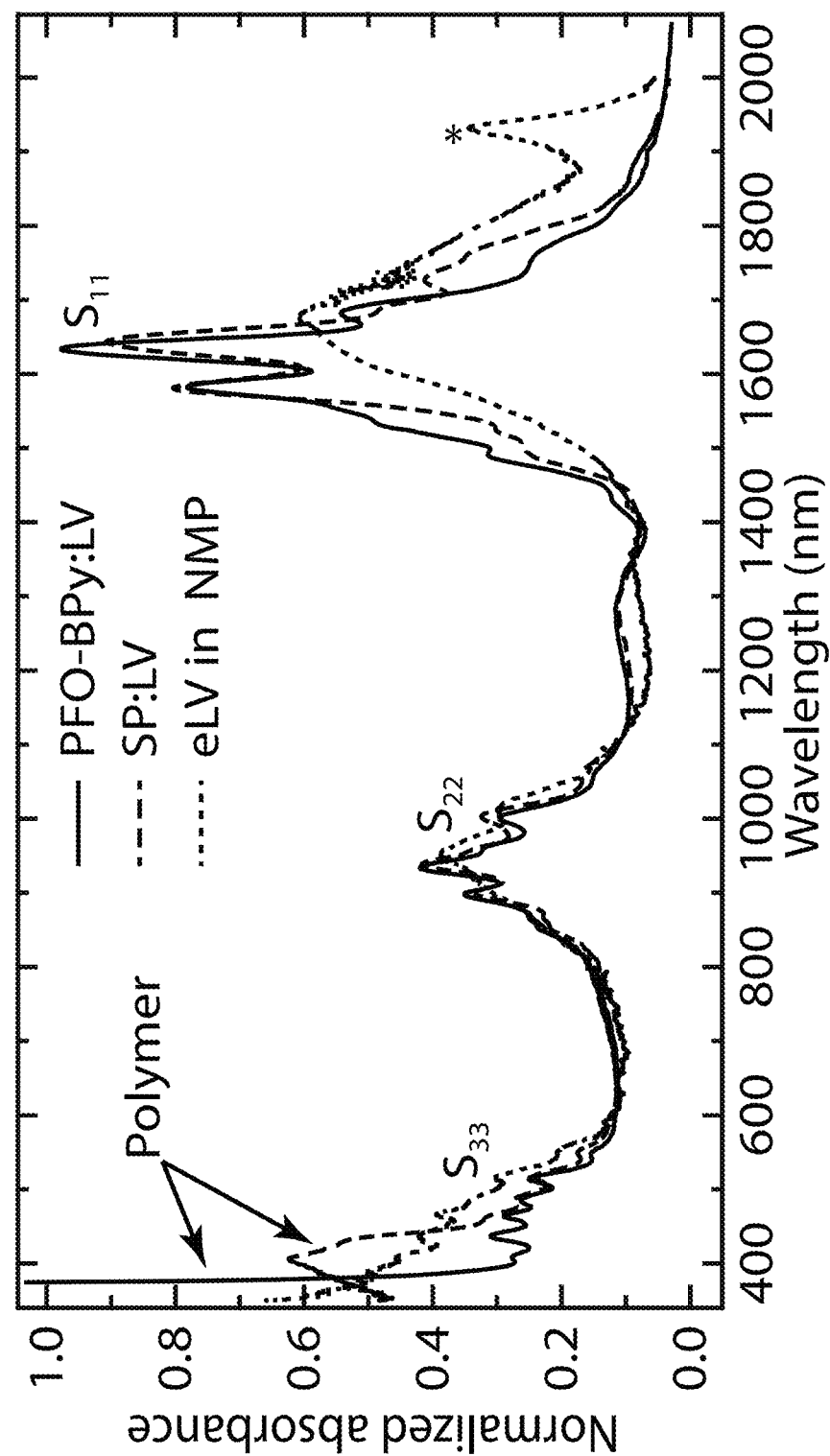

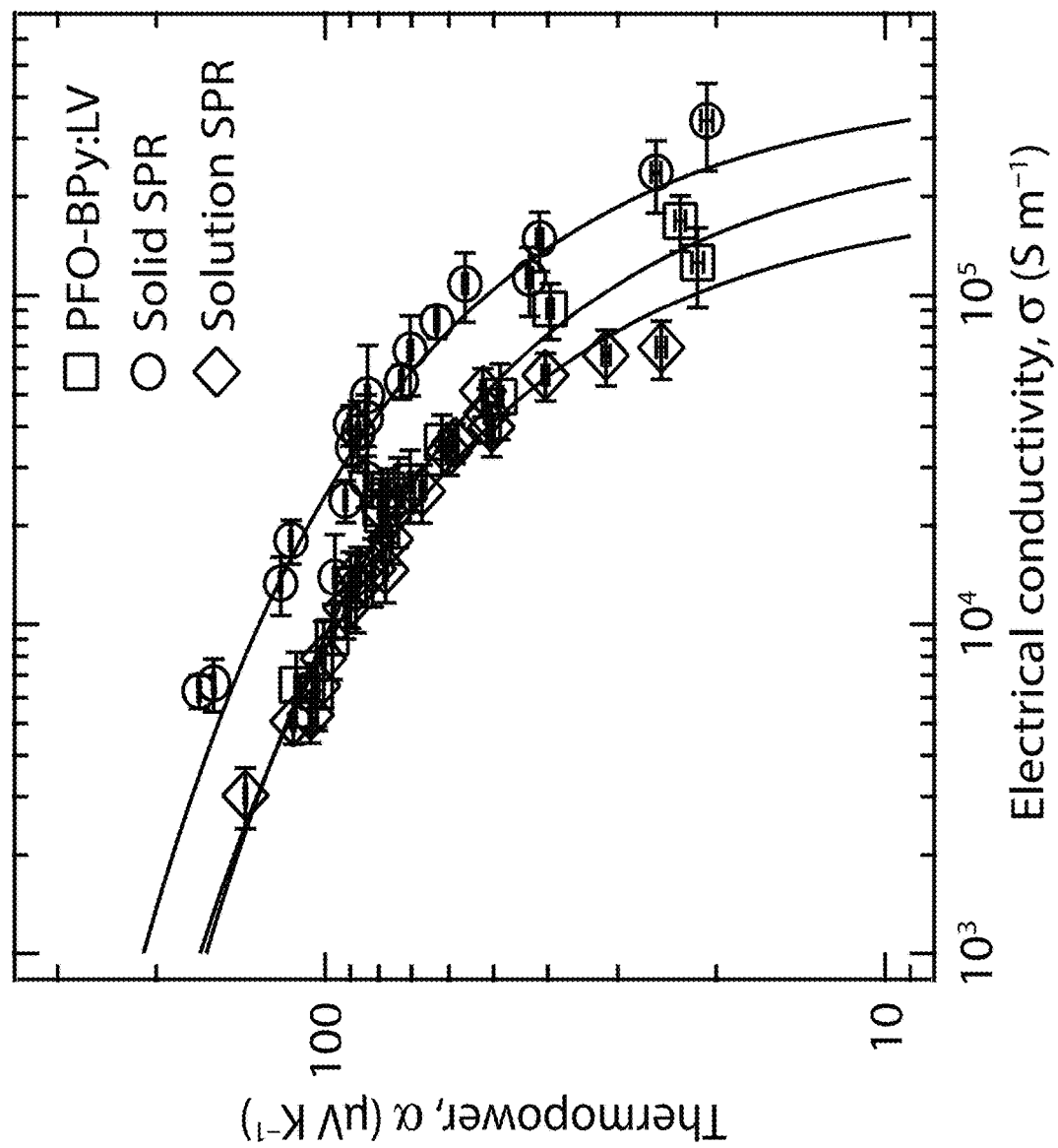

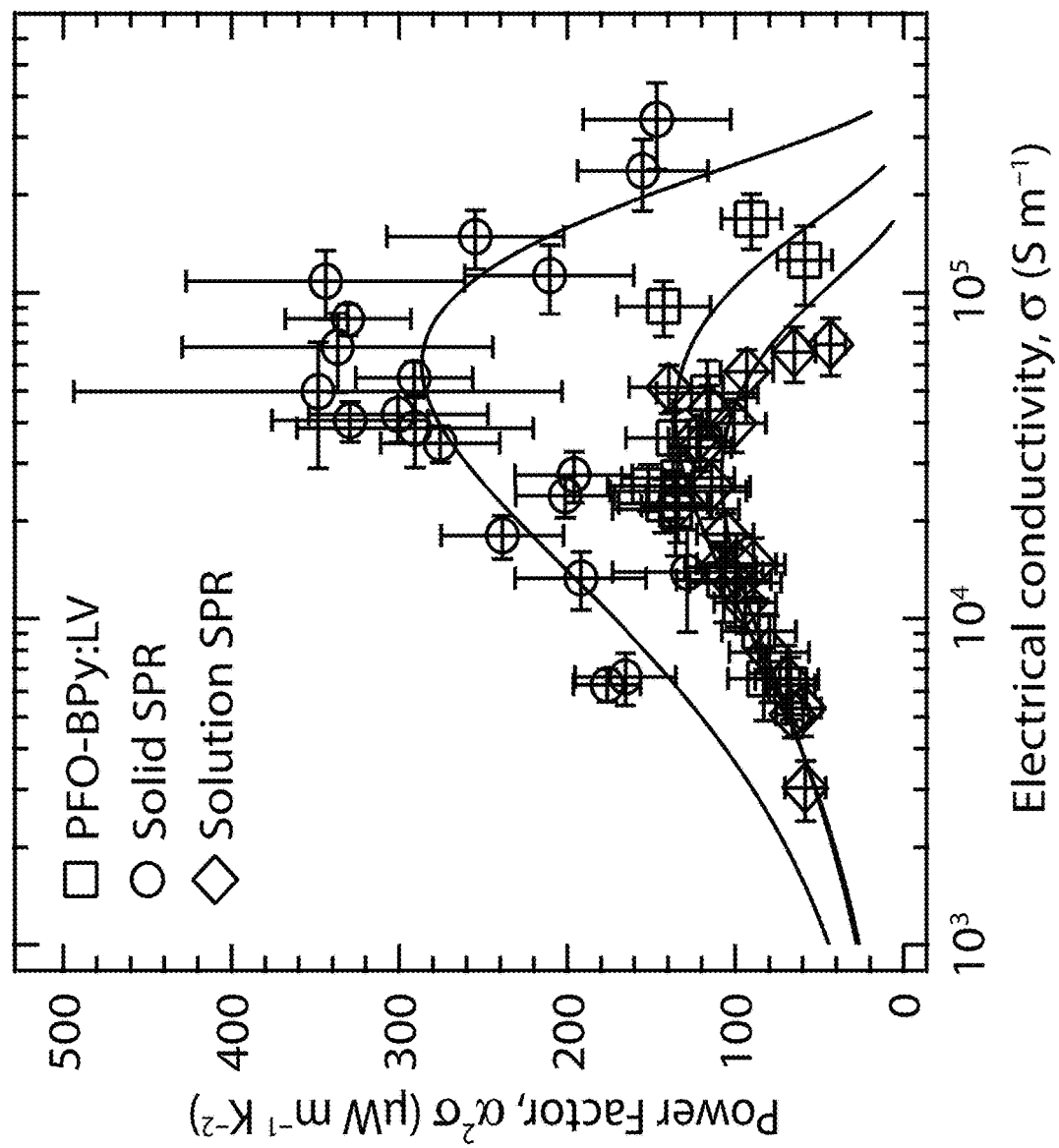

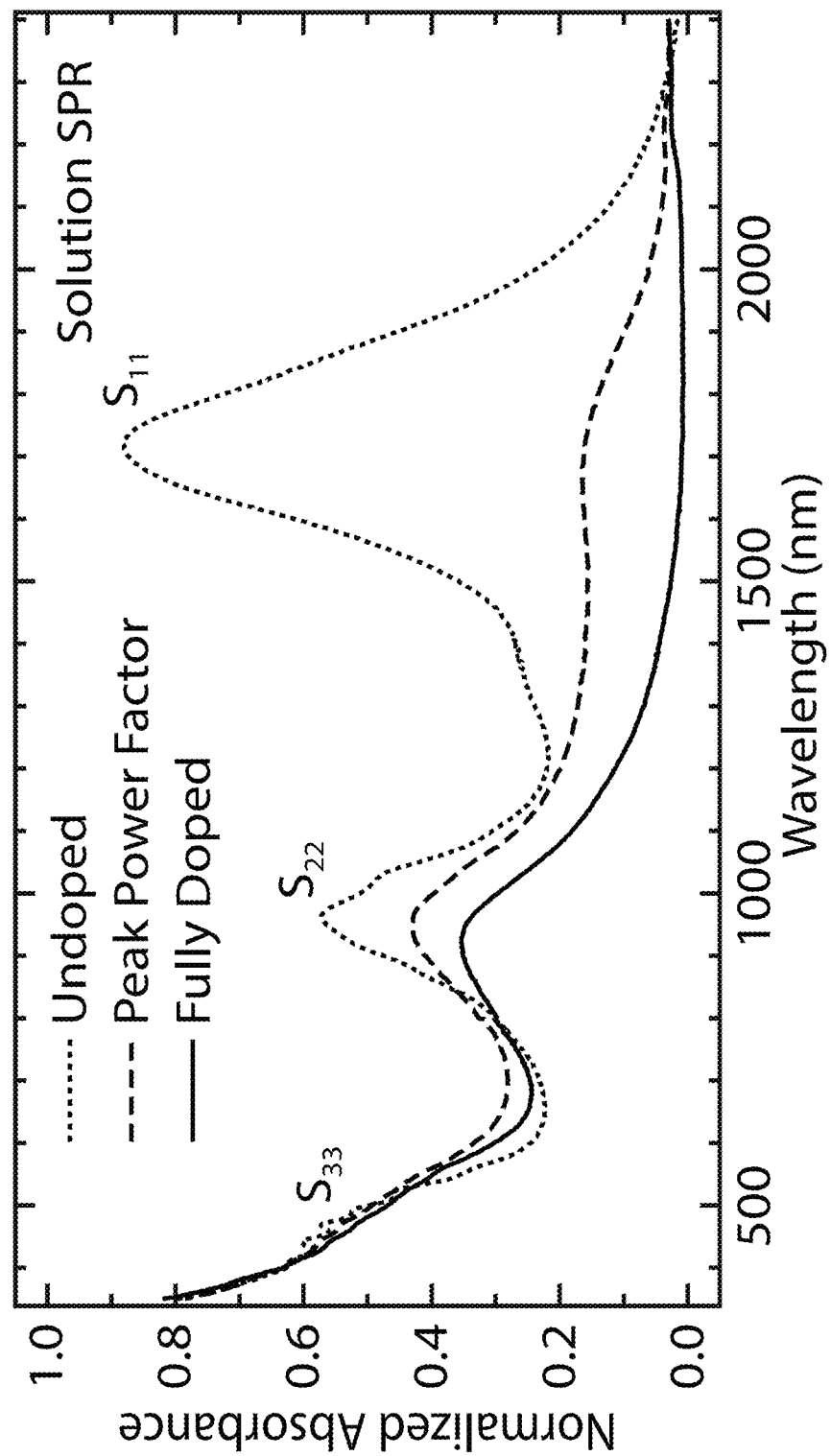

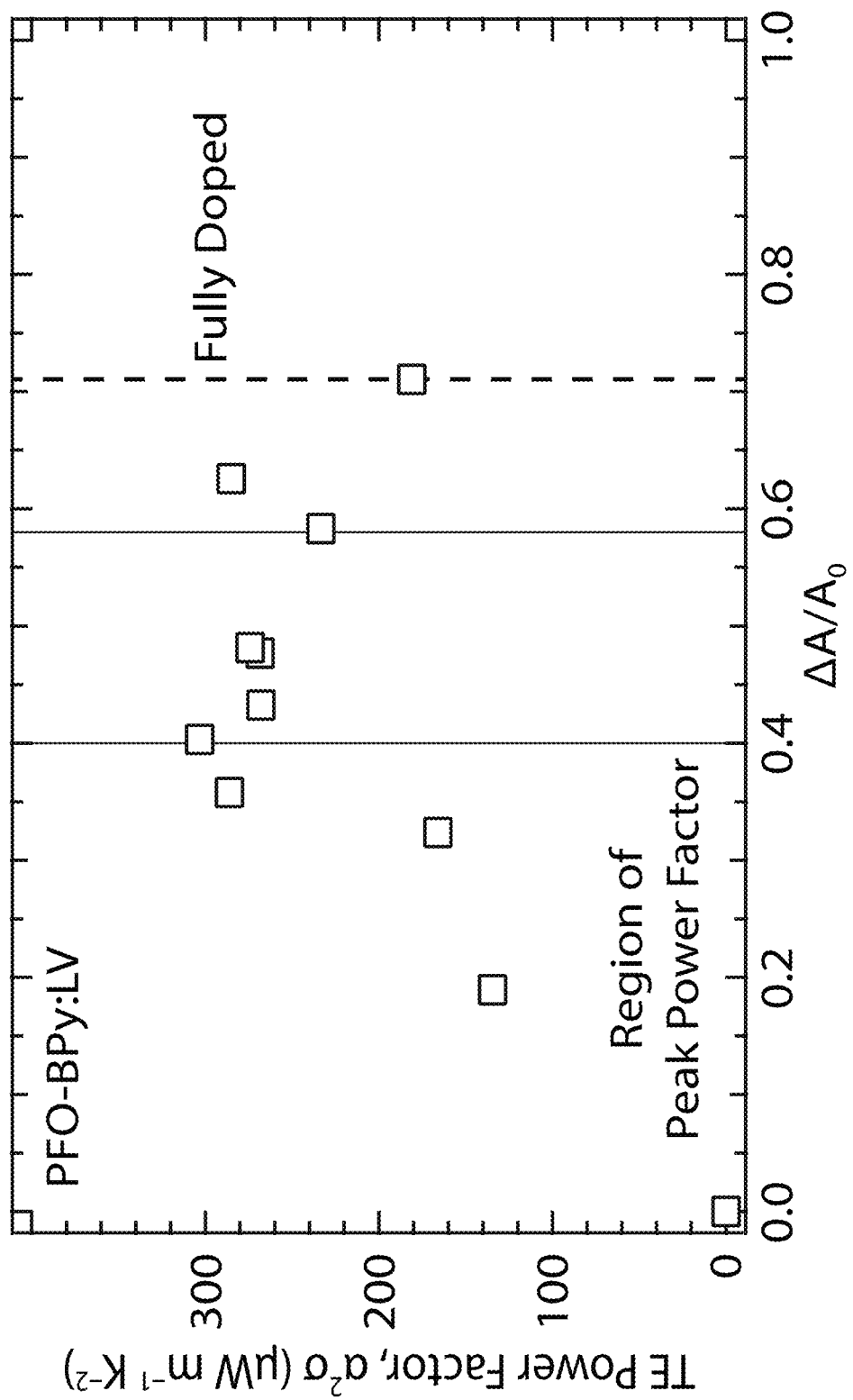

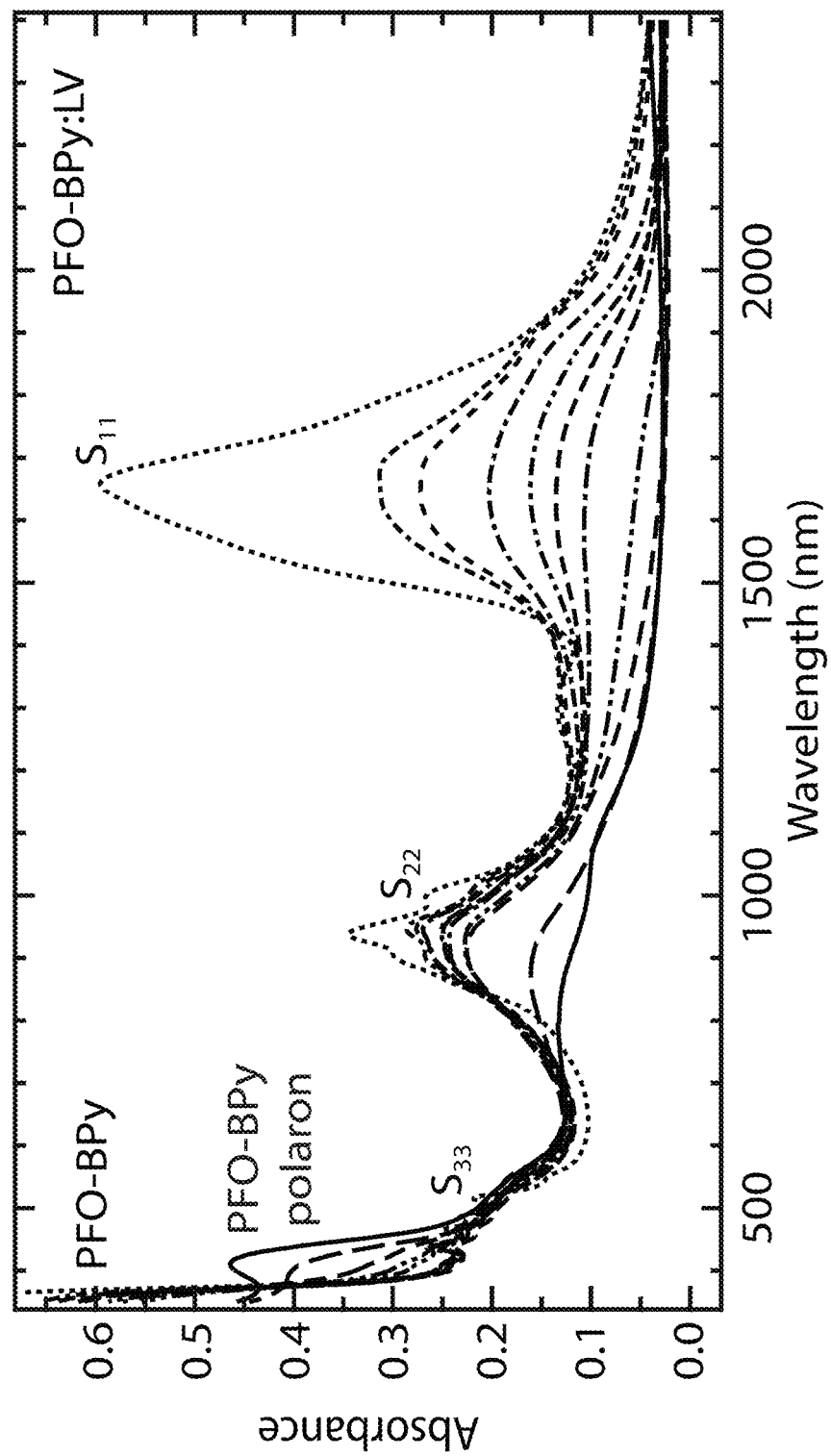

METHODS OF PREPARING SINGLE-WALLED CARBON NANOTUBE NETWORKS

CROSS-REFERENCE TO RELATED APPLICATIONS

This application claims priority under 35 U.S.C. § 119 to U.S. Provisional Patent Application No. 62/191,911, filed on Jul. 13, 2015, U.S. Provisional Patent Application No. 62/211,064, filed on Aug. 28, 2015, and U.S. Provisional Patent Application No. 62/316,709, filed on Apr. 1, 2016, the contents of which are hereby incorporated by reference in their entireties.

CONTRACTUAL ORIGIN

The United States Government has rights in this invention under Contract No. DE-AC36-08GO28308 between the United States Department of Energy and the Alliance for Sustainable Energy, LLC, the Manager and Operator of the National Renewable Energy Laboratory.

BACKGROUND OF THE INVENTION

The present invention relates to single-walled carbon nanotubes (SWCNTs), which may be used for thermoelectric (TE) power generation. The development of inexpensive and efficient TE materials offers the prospect of converting waste heat into pollution-free electricity in standalone power generation systems, cogeneration architectures (e.g., coupled to a photovoltaic module), and/or cooling systems (e.g., microprocessor cooling). It is desirable for efficient TE materials to be good at conducting electricity but not heat, so that a thermal gradient may be maintained to produce the TE effect. However, this is challenging for most material systems, because the electrical and thermal conductivities are typically related to each other via the charge carrier density, such that the thermal conductivity increases as the electrical conductivity increases. Decoupling the electrical and thermal conductivities has been achieved in some inorganic semiconductors (ISCs), such as bismuth telluride ($Bi_2Te_3$), although further improvements in these materials are likely to require the development of complex and/or nanoscale structures. Complex fabrication strategies, combined with material cost, scarcity, toxicity, and disposal, may significantly limit the potential for large-scale deployment of TE devices based on such materials.

The size-tunable physical properties of solution-phase processable nanomaterials may enable diverse strategies for energy harvesting/storage and inexpensive, bottom-up approaches for fabricating devices with unique form and function (e.g., flexible, lightweight, and/or wearable). Nanostructuring of bulk ISCs has shown particular promise for improving TE energy conversion devices, which convert thermal energy from waste and natural heat sources into electricity, due to the beneficial formation of nanoscale interfaces. However, the best-performing ISCs are incompatible with applications that require the TE generator to adopt irregular, or even flexible, form factors.

In contrast, nanostructured organic semiconductors (OSCs), including SWCNTs, offer a number of intriguing technological characteristics for TE applications, such as earth-abundant raw materials, low-cost deposition, and flexible form factors. Despite their promising electronic properties, SWCNTs have received little attention in the context of TE energy conversion, although several studies have focused on the use of SWCNTs as inclusions in composite materials based on conducting polymers. Two recent studies demonstrated higher thermopowers for films enriched in semiconducting (s-SWCNT) species than those containing significant fractions of metallic (m-SWCNT) species. Beyond these results, little has been known about the detailed dependence of the TE power factor and the thermal conductivity on the SWCNT diameter, electronic structure, and carrier density. Although large thermal conductivities ($\kappa > 1{,}000$ W m$^{-1}$ K$^{-1}$) have been observed for individual SWCNTs, much lower values ($\kappa < 35$ W m$^{-1}$ K$^{-1}$) have been obtained for mats of nanotube ropes or bundles.

SUMMARY OF THE INVENTION

Exemplary embodiments of the invention provide methods for determining desired doping conditions for a semiconducting single-walled carbon nanotube (s-SWCNT). One exemplary method includes doping each of a plurality of s-SWCNT networks under a respective set of doping conditions; determining a TE power factor as a function of a fractional bleach of an absorption spectrum for the plurality of s-SWCNT networks doped under the respective sets of doping conditions; and using the function to identify one of the TE power factors within a range of the fractional bleach of the absorption spectrum, wherein the identified TE power factor corresponds to the desired doping conditions.

The doping may include immersing the s-SWCNT network in a solution comprising a charge-transfer dopant until a charge carrier doping level of the s-SWCNT network is saturated; and subsequently reducing the charge carrier doping level of the s-SWCNT network. The charge-transfer dopant may include triethyloxonium hexachloroantimonate (OA).

Alternatively, the doping may include sequentially immersing the s-SWCNT network in solutions comprising increasing concentrations of the charge-transfer dopant. The charge-transfer dopant may include OA.

The method may include controlling a band gap of the s-SWCNT network by adjusting a diameter of carbon nanotubes of the s-SWCNT network. The band gap may be controlled to have a value between approximately 1.0 eV and approximately 1.2 eV.

The method may also include removing at least a portion of a polymer wrapped around carbon nanotubes of the s-SWCNT network. Further, the method may also include, before determining the desired doping conditions, selectively extracting s-SWCNTs from polydisperse SWCNT soot using polyfluorene-based polymers; and performing ultrasonic spray deposition of the s-SWCNTs to form the s-SWCNT networks.

The method may also include doping an s-SWCNT network under the desired doping conditions. The identified TE power factor may be a maximum TE power factor within the range of the fractional bleach of the absorption spectrum. The identified TE power factor may be at least 340 µW m$^{-1}$ K$^{-2}$.

According to another aspect of the invention, a composition is provided. The composition includes a doped s-SWCNT network, wherein the s-SWCNT network has a TE power factor of at least 340 µW m$^{-1}$ K$^{-2}$. The s-SWCNT network may have a band gap between approximately 1.0 eV and approximately 1.2 eV. The s-SWCNT network may be doped with OA.

Other objects, advantages, and novel features of the present invention will become apparent from the following detailed description of the invention when considered in conjunction with the accompanying figures.

BRIEF DESCRIPTION OF THE DRAWINGS

FIGS. 2(a)-2(e) show density functional theory (DFT) calculations of thermopower for m-SWCNTs and s-SWCNTs;

FIGS. 9(a)-9(g) show p-type doping of s-SWCNT networks with OA;

FIG. 10 shows the integrated density of states (DOS) for a semiconducting carbon nanotube;

FIGS. 12(a)-12(f) show TE properties of various polyfluorine/s-SWCNT thin films;

FIGS. 14(a)-14(d) show the temperature-dependent TE properties of undoped and doped PFO-BPy:LV s-SWCNT networks.

FIGS. 16(a) and 16(b) show doping "hysteresis" in TE properties of PFH-A:HiPCO networks;

FIGS. 17(a)-17(f) compare characteristics of s-SWCNT networks having polymer-wrapped tubes with s-SWCNT networks without the polymer-wrapped tubes;

FIGS. 19(a)-19(b) show the TE properties of s-SWCNT networks having polymer-wrapped tubes and s-SWCNT networks without the polymer-wrapped tubes;

FIGS. 20(a)-20(i) show the absorbance, electrical conductivity, and TE power factor of s-SWCNT networks having polymer-wrapped tubes and s-SWCNT networks without the polymer-wrapped tubes; and FIGS. 21(a)-21(c) show more detailed absorption spectra of s-SWCNT networks having polymer-wrapped tubes and s-SWCNT networks without the polymer-wrapped tubes.

DETAILED DESCRIPTION OF EXEMPLARY EMBODIMENTS

Exemplary embodiments of the invention provide s-SWCNT networks with a carefully controlled chirality distribution (or bandgap) and carrier density that are capable of achieving large TE power factors, higher than 340 $\mu W\, m^{-1}\, K^{-2}$, comparable to the best-performing conducting polymers and larger than previously observed for carbon nanotube films. Controlling the carrier doping according to exemplary embodiments of the invention significantly reduces the thermal conductivity $\kappa$ relative to undoped s-SWCNT networks. Removing a polymer wrapped around the carbon nanotubes improves the TE properties of the s-SWCNT networks.

The TE performance of a material is represented by the dimensionless figure-of-merit $zT=(\alpha^2\sigma)T/\kappa$, where $\alpha$ is the thermopower (Seebeck coefficient), $\sigma$ is the electrical conductivity, $\alpha^2\sigma$ is the TE power factor, $\kappa$ is the thermal conductivity, and T is the absolute temperature. The thermopower $\alpha$ is the electromotive force $\Delta V$ generated across a material when it is subjected to the temperature difference $\Delta T$, and is given by $\alpha=\Delta V/\Delta T$. The TE power factor $\alpha^2\sigma$ may be controlled when optimizing the figure-of-merit zT of a material system. To achieve a high figure-of-merit zT, the TE power factor $\alpha^2\sigma$ may be maximized while maintaining a low thermal conductivity $\kappa$.

Figure 1A:
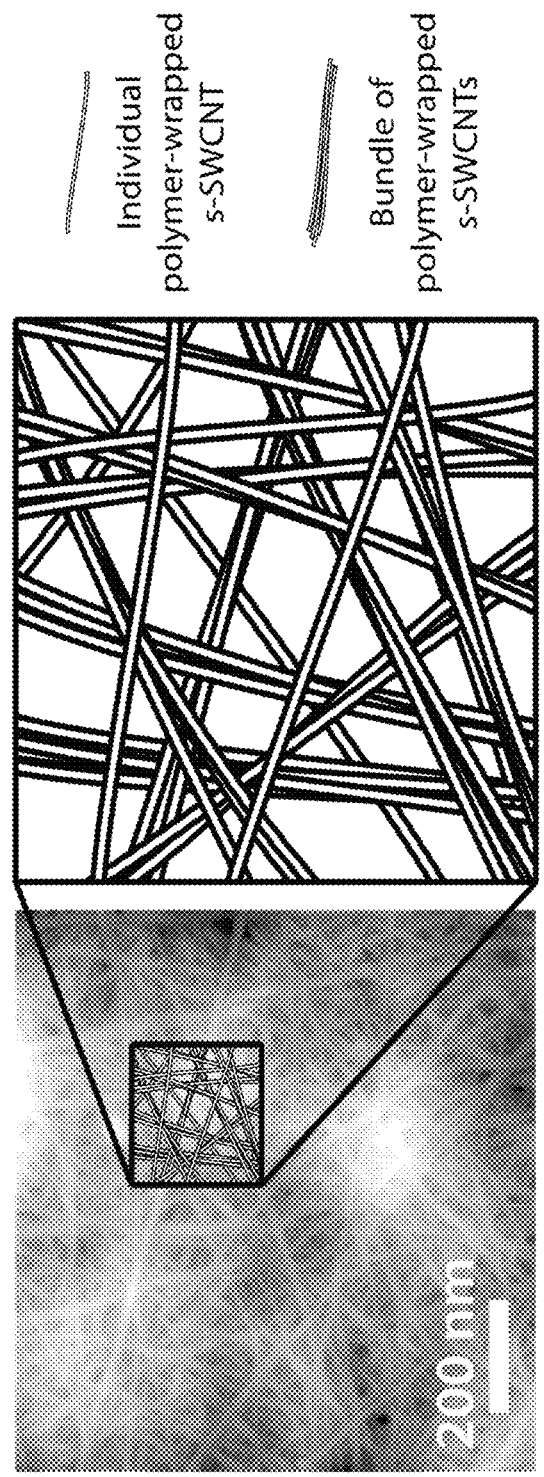
FIGS. 1(a) and 1(b) show atomic force microscopy (AFM) images and corresponding schematics of a nanocomposite network with s-SWCNT inclusions dispersed in a polymer matrix and a network of polymer-free s-SWCNTs, respectively.
Figure 1B:
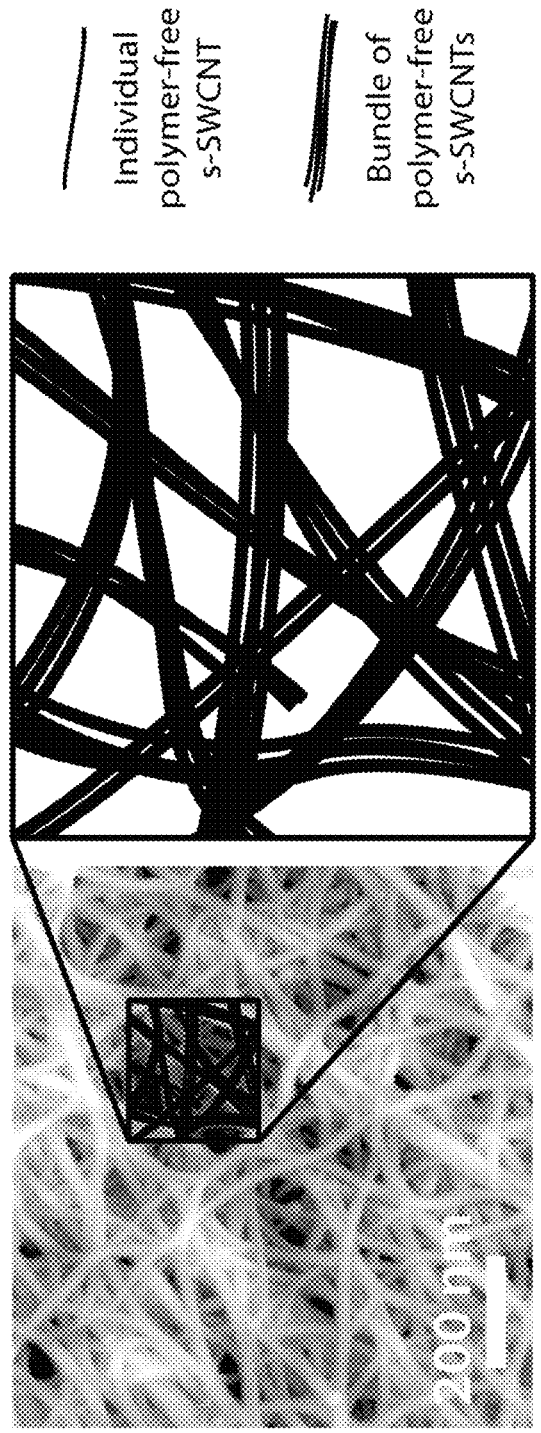

FIGS. 1(a) and 1(b) show AFM images and corresponding schematics of a nanocomposite network with s-SWCNT inclusions dispersed in a polymer matrix and a network of polymer-free s-SWCNTs, respectively. In both cases, the networks can include individual s-SWCNTs and bundles or ropes of s-SWCNTs. It is possible to control thermal and electrical transport properties by reducing the dimensionality of a sample. On a smaller length scale, boundary interfaces and inclusions introduce interfaces that can be effective scattering centers for vibrons or phonons, or allow transmission of only high energy electrons.

As discussed in further detail below, according to exemplary embodiments of the present invention, s-SWCNTs are enriched with any suitable material, such as conjugated polymers or copolymers based on various chemical moieties (for example, fluorene, thiophene, carbazole, etc), DNA, or surfactants, and are extracted from raw SWCNT soot, which may be a raw nanotube material. The s-SWCNTs are composed of carbon atoms, but may include substitutionally-doped elements, such as nitrogen or boron atoms, in place of some carbon atoms. Uniform thin films of s-SWCNTs are then formed by any suitable method, such as ultrasonic spraying. Next the s-SWCNT films are doped using a thermally stable p-type or n-type dopant. Any suitable charge-transfer dopant, such as Lewis acids or bases (such as 2,3,5,6-Tetrafluoro-tetracyanoquinodimethane (F4-TCNQ), triethyloxonium hexachloroantimonate (OA), hydrazine, and/or ethylenediamine), and/or Brönsted-Lowry acids or bases (such as nitric acid, sulphuric acid, and/or trifluoroacetic acid), may be used. Lewis or Brönsted acids will generate p-type s-SWCNT networks (where holes are majority carriers), and Lewis or Brönsted bases will generate n-type s-SWCNT networks (where electrons are majority carriers). The doping level is tuned via the amount of adsorbed dopant. By tuning the doping level, the TE power factor $\alpha^2\sigma$ may be optimized.

Exemplary embodiments of the present invention provide thin films of a potentially inexpensive organic material that can efficiently convert waste heat to electricity. As discussed above, exemplary methods use enriched s-SWCNTs and tune their TE properties by using controllable amounts of dopant molecules to tune the Fermi energy of the s-SWCNTs that constitute the film. The s-SWCNTs may also have tunable colors, which may be used in TE fabrics, because they are nanomaterials with diameter-tunable bandgaps. The polymer, the diameter distribution, the electronic structure of particular s-SWCNTs, and/or the overall composition of the network may be adjusted to define the TE properties of the film. For example, if specific polymers provide large TE power factors $\alpha^2\sigma$, these polymers may be engineered into the composite to achieve higher TE power factors $\alpha^2\sigma$ by providing an increase in the thermopower $\alpha$ at high electrical conductivity $\sigma$. Similarly, if specific s-SWCNT densities of states provide large TE power factors $\alpha^2\sigma$, these s-SWCNT densities may be engineered into the composite to achieve higher TE power factors $\alpha^2\sigma$ by providing an increase in the thermopower $\alpha$ at high electrical conductivity $\sigma$.

In addition, highly pure single-chirality s-SWCNTs may be incorporated into otherwise polydisperse s-SWCNT composites. This may provide advantageously high thermopowers $\alpha$ at very high electrical conductivities. Further, films may be fabricated with tailored isotopic (or atomic) compositions to rationally incorporate phonon scattering centers. This may provide advantageously low thermal conductivities while maintaining the high thermopowers $\alpha$ and high electrical conductivities.

Exemplary embodiments of the present invention may maintain a very high thermopower $\alpha$ in an SWCNT while simultaneously realizing high electrical conductivity $\sigma$. These two properties define the TE power factor $\alpha^2\sigma$ within the TE figure-of-merit zT, and are very hard to optimize simultaneously because they typically vary inversely with respect to each other. At low carrier densities, the thermopower $\alpha$ is typically high, while the electrical conductivity $\sigma$ is low. As the carrier density rises, the thermopower $\alpha$ falls and the electrical conductivity $\sigma$ rises. Exemplary embodiments of the present invention may utilize s-SWCNTs surrounded by a fluorene-based polymer or co-polymer host as a material that can be optimized by tuning the Fermi energy. This type of tunability may not be possible in films containing both s-SWCNTs and m-SWCNTs, because m-SWCNTs have a finite density of states (DOS) at all energies, resulting in a low intrinsic thermopower $\alpha$, and are very hard to tune via molecular doping. Further, exemplary embodiments of the present invention utilize the extreme sensitivity of fluorene-based polymers or co-polymers for extracting high yields of s-SWCNTs. These polymers enable highly selective dispersion of particular distributions of SWCNTs, and these distributions can be sensitively tuned by choosing the appropriate polymer and SWCNT synthesis conditions, as discussed in further detail below.

Exemplary embodiments of the invention provide methods for fabricating and doping TE materials based on enriched s-SWCNTs. Experimental data has verified theoretical predictions that suggest that the thermopower $\alpha$ for s-SWCNTs can greatly exceed those experimentally obtained in related art studies (500 µV K$^-$) at low doping densities. By controlling the doping conditions, thermopower $\alpha$ values can be maintained well over 100 µV K$^{-1}$ even at very high carrier densities and electrical conductivity $\sigma$ values, providing an optimum TE power factor $\alpha^2\sigma$ of approximately 340 µW m$^{-1}$ K$^{-2}$ for s-SWCNTs with an electronic band gap of approximately 1.0 eV to 1.2 eV. The doping method according to exemplary embodiments of the invention significantly hinders the vibron/phonon contribution that dominates the thermal conductivity $\kappa$ in undoped carbon nanotube networks.

First-principles density functional theory (DFT) calculations of the DOS and thermopower for representative m- and s-SWCNTs have been performed. In the diffusive transport regime, the thermopower can be expressed with the Mott formula:

$$\alpha(E) = -\frac{1}{eT}\left[\frac{\int \sigma(E)(E-E_r)\left(-\frac{\partial f}{\partial E}\right)dE}{\int \sigma(E)\left(-\frac{\partial f}{\partial E}\right)dE}\right] \quad (1)$$

The energy-dependent electrical conductivity is given by $\sigma(E)=e^2 N_e(E)D(E)$, a product of the DOS and diffusion constant, which both depend on energy. In the low-temperature approximation, the thermpower value can be expressed as a log term:

$$\alpha(E) = -\frac{\pi^2}{3}\frac{k_B^2 T}{e}\left[\frac{\partial \ln[\sigma(E,\vec{r})]}{\partial E}\right]_{E=E_r} \quad (2)$$

and the thermopower approximately equates to the addition of a ballistic term and a diffusive term, $\alpha \approx \alpha_{ball} + \alpha_{diff}$. Thus the total thermopower can be written as:

$$\alpha(E) = \quad (3)$$
$$-\frac{1}{eT}\left[\frac{\int N_e(E)(E-E_f)\left(-\frac{\partial f}{\partial E}\right)dE}{\int N_e(E)\left(-\frac{\partial f}{\partial E}\right)dE} + \frac{\int D(E)(E-E_f)\left(-\frac{\partial f}{\partial E}\right)dE}{\int D(E)\left(-\frac{\partial f}{\partial E}\right)dE}\right]_{E=E_f}$$

where the first term describes the ballistic contribution, due to the shape of the DOS, and the second term describes the diffusive contribution. In this example, only the ballistic contribution to the thermopower was calculated. Initial work suggests that the diffusive term is a simple constant with the same sign as the ballistic term, meaning that the total achievable thermopower may be slightly larger than is estimated here.

In the low-temperature approximation, the thermopower value can be expressed as a log term:

$$\alpha(E_f) = -\frac{\pi^2}{3}\frac{k_B^2 T}{e}\left[\frac{\partial \ln[N(E)]}{\partial E} + \frac{\partial \ln[D(E)]}{\partial E}\right]_{E=E_f} \quad (4)$$

where E is the energy, $E_f$ is the energy of the Fermi level, the first term inside the square brackets is the ballistic (or intrinsic) contribution to the thermopower due to the shape of the DOS N(E), the second term is the diffusive (or extrinsic) contribution, due to the energy-dependence of the diffusion coefficient D(E), $k_B$ is the Boltzmann constant, T is the absolute temperature, and e is elementary charge. In this example, only the ballistic contribution to the thermopower was calculated based on Equation (4), but the contribution from the diffusive component could also be determined as discussed above.

In this example, Projected-Augmented Wave (PAW) and Perdew-Burke-Ernzerhof (PBE) exchange-correlation functional were employed as implemented in Vienna Ab Initio Simulation Package (VASP). A plane wave basis set with a kinetic energy cutoff of 400 eV was used, and all atomic positions were relaxed until forces are less than 0.025 eV/Å.

For the calculations of the electronic DOS, the (500×1×1), (40×1×1) and (20×1×1) Γ-centered k-points samplings were used for (9,9), (7,5) and (10,8) SWCNT, respectively, and a Gaussian broadening of 0.02 eV was applied.

Figure 2A:
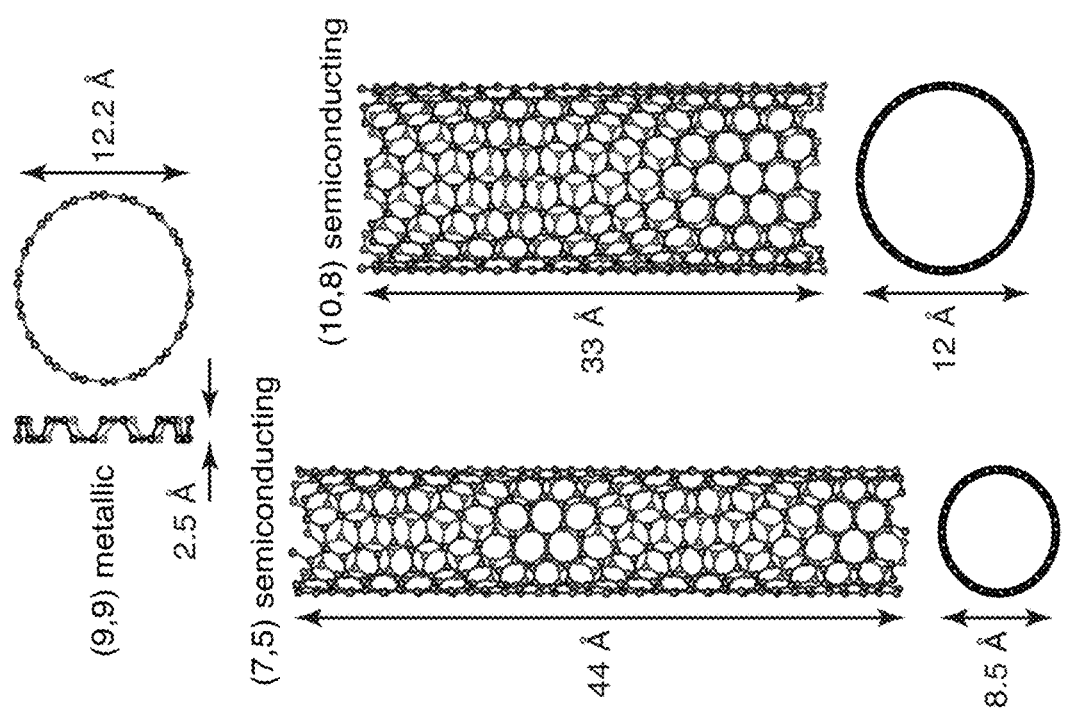
Figure 2B:
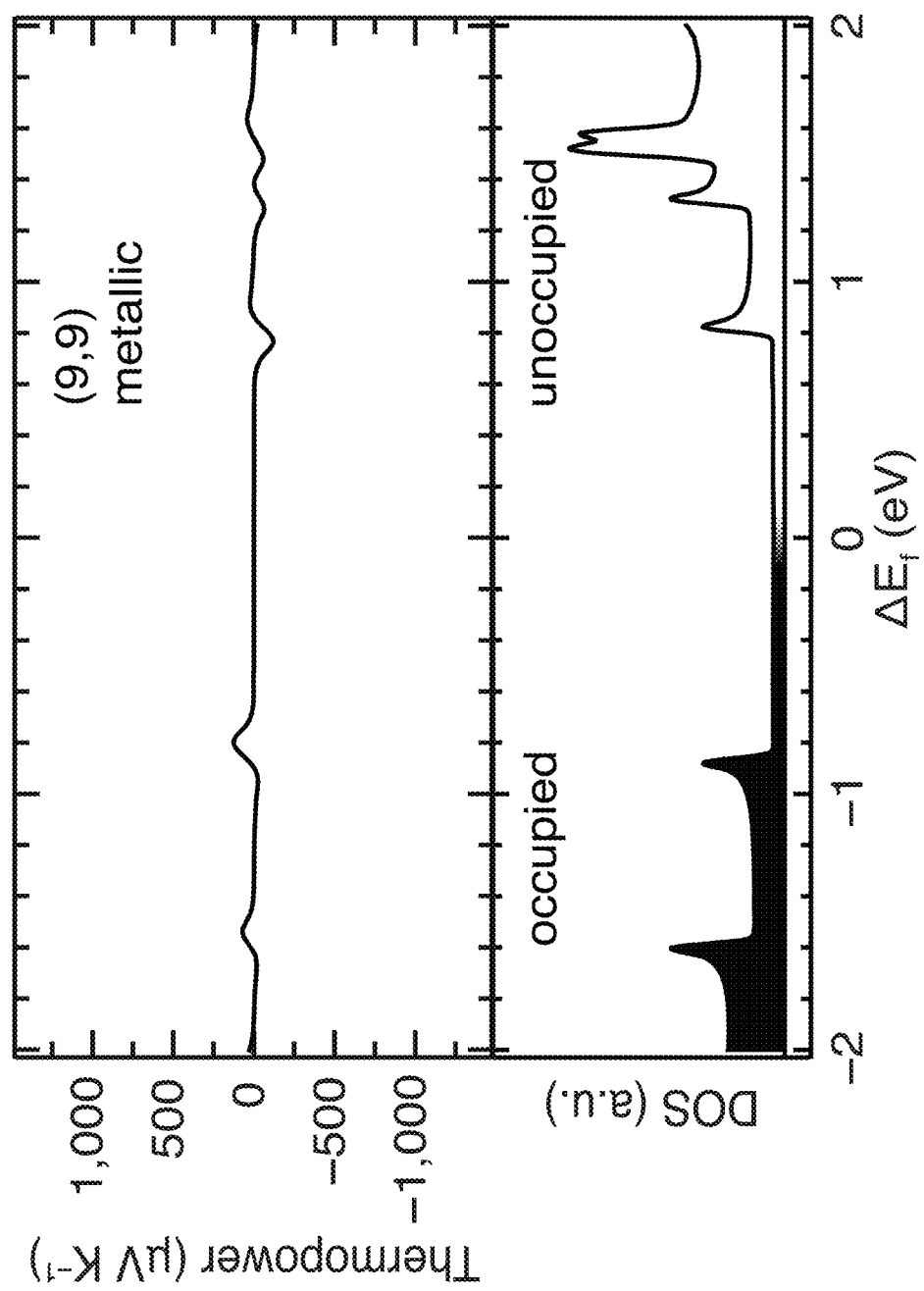
Figure 2C:
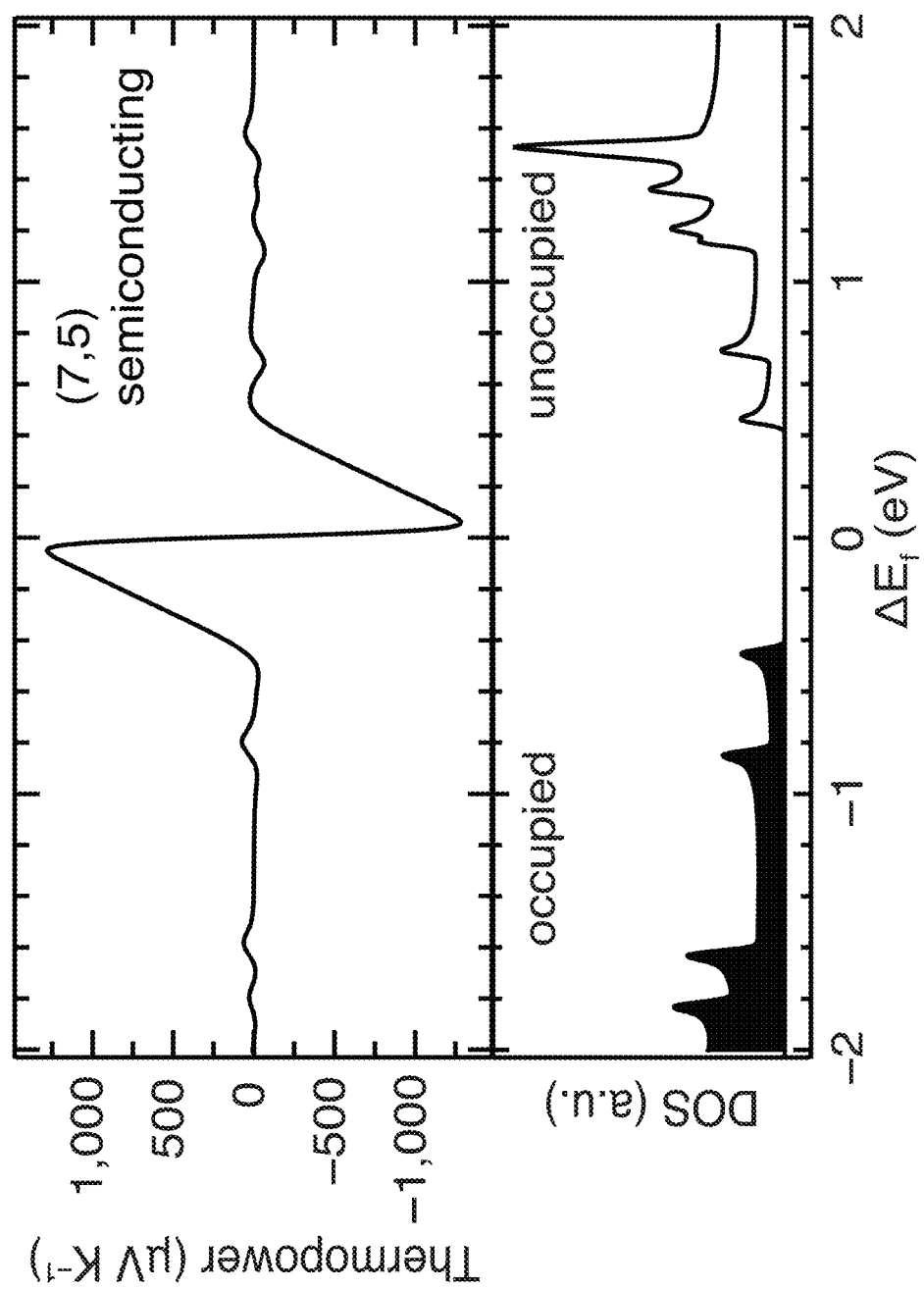
Figure 2E:
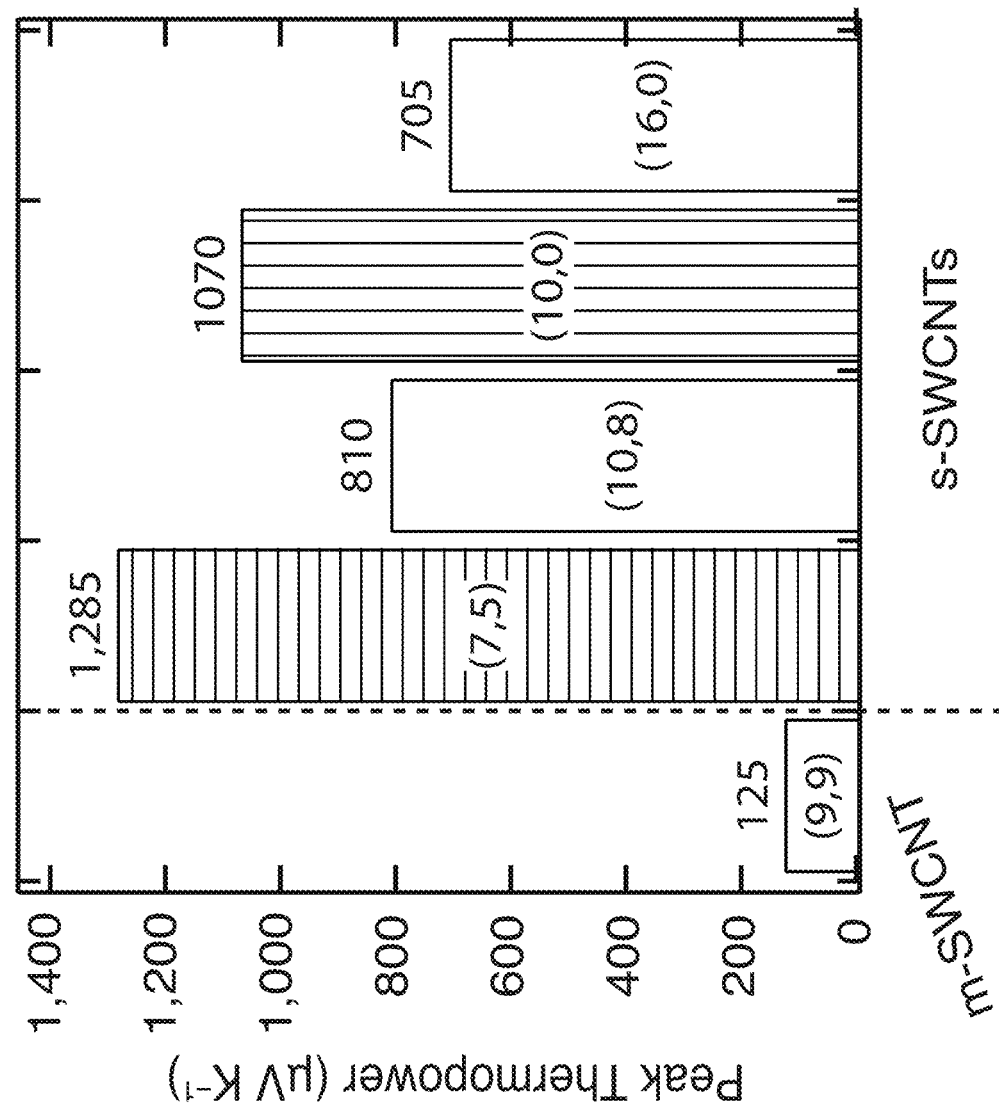

FIGS. 2(a)-2(e) show DFT calculations of thermopower α for m-SWCNTs and s-SWCNTs. FIG. 2(a) shows the unit cells for three of the five SWCNTs calculated: the (7,5) and (10,8) s-SWCNTs are representative of the small-diameter carbon monoxide disproportionation (CoMoCAT®) and large-diameter laser vaporization (LV) samples, respectively, whereas the (9,9) is representative of large-diameter m-SWCNTs. FIGS. 2(b)-1(d) show the thermopower α (top panels) as a function of Fermi energy position within the electronic DOS (bottom panels) for the same three SWCNTs, where the zero energy was fixed to the Fermi energy position of undoped SWCNTs. FIG. 2(e) shows a comparison of the DFT-calculated peak thermopower α for all five SWCNT species.

Figure 3:
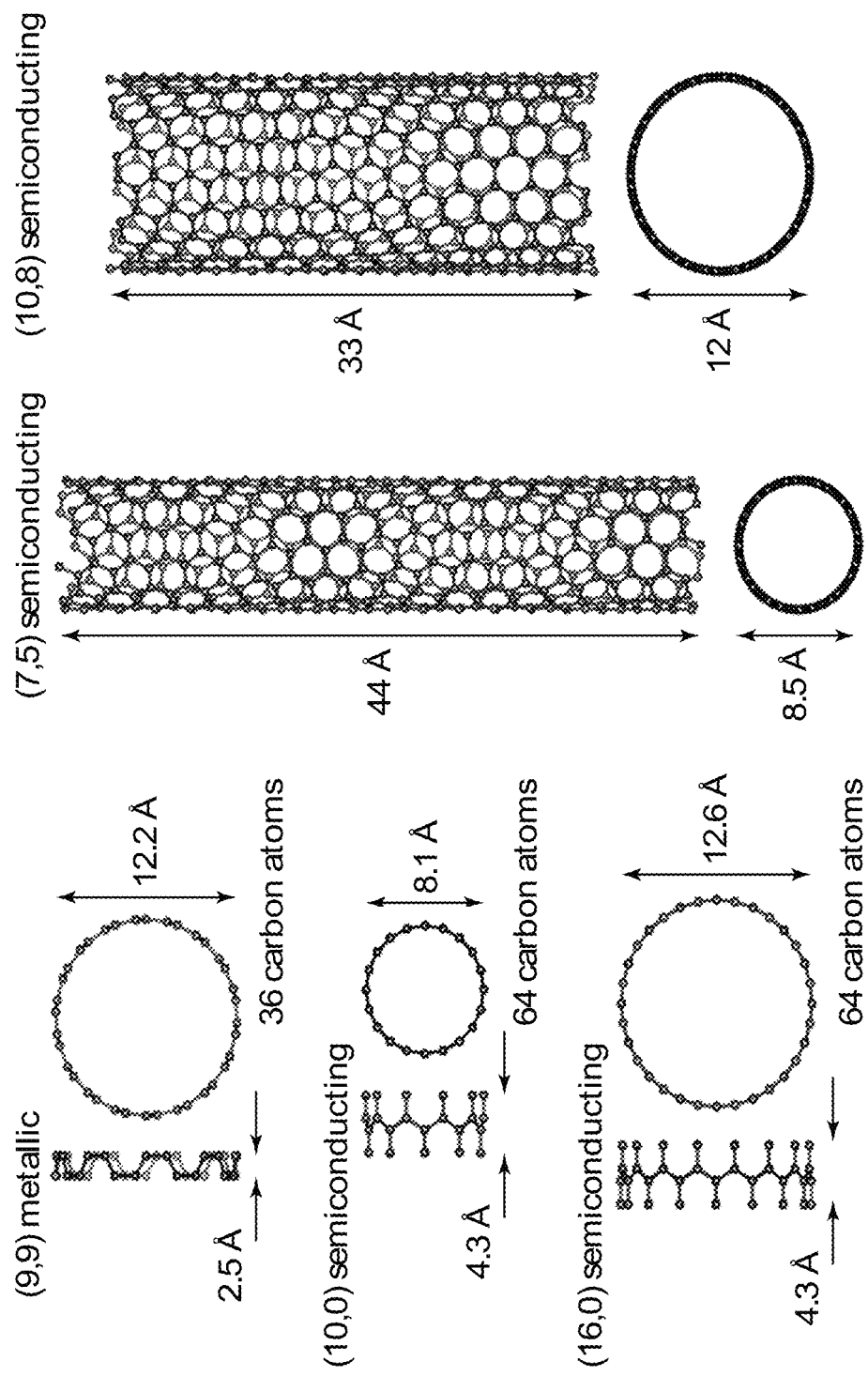
FIG. 3 shows unit cells of SWCNTs.

As discussed above, the primary representative semiconducting species studied by DFT were the (7,5) and (10,8) s-SWCNTs, whereas the primary metallic species was the (9,9) m-SWCNT. For the calculations of the electronic DOS, the (500×1×1), (40×1×1) and (20×1×1) Γ-centered k-points samplings were used for (9,9), (7,5) and (10,8) SWCNT, respectively, and a Gaussian broadening of 0.02 eV was applied. In order to rule out possible effects due to the reduced size of the unit cell of the (9,9) m-SWCNT, calculations were also carried out on the zigzag (10,0) and (16,0) s-SWCNTs, which have similar diameters to the (7,5) and (10,9) s-SWCNTs, respectively, but much smaller unit cells, similar in size to the (9,9) m-SWCNT. FIG. 3 shows the unit cells of the five main SWCNT chiralities considered in the DFT calculations.

The DFT calculations demonstrate that the peak of the intrinsic thermopower α of two model s-SWCNTs is nearly an order of magnitude higher than that of the (9,9) m-SWCNT, qualitatively consistent with recent experimental results from the related art. However, the magnitude of the predicted thermopowers α for the s-SWCNTs is dramatically higher than values obtained in recent experiments from the related art. A small Fermi energy shift, $\Delta E_F$, of only approximately 60 meV in either direction produces the maximum thermopower α of approximately 1,300 $\mu V \ K^{-1}$ and 800 $\mu V \ K^{-1}$ for the (7,5) and (10,8) s-SWCNTs shown in FIG. 2(b), respectively, nearly an order of magnitude higher than the highest values previously observed experimentally (approximately 160 $\mu V \ K^{-1}$). While the thermopower α decays monotonically with increasing $\Delta E_F$, the calculations suggest that the thermopower α within controllably doped s-SWCNTs can remain well above 100 $\mu V \ K^{-1}$ for sizable shifts in the Fermi energy; for example, α for the (7,5) s-SWCNT is 200 $\mu V \ K^{-1}$ for $\Delta E_F \approx 0.4$ eV. FIG. 2(c) summarizes the peak DFT-calculated thermopowers α for five different SWCNTs, demonstrating that the DFT-calculated maximum thermopower α for all four s-SWCNTs was dramatically higher than the (9,9) m-SWCNT. Thermopowers α of this magnitude, paired with the already well-documented high electrical conductivities of doped s-SWCNTs, promises significant technological potential for these materials in TE devices.

Figure 4A:
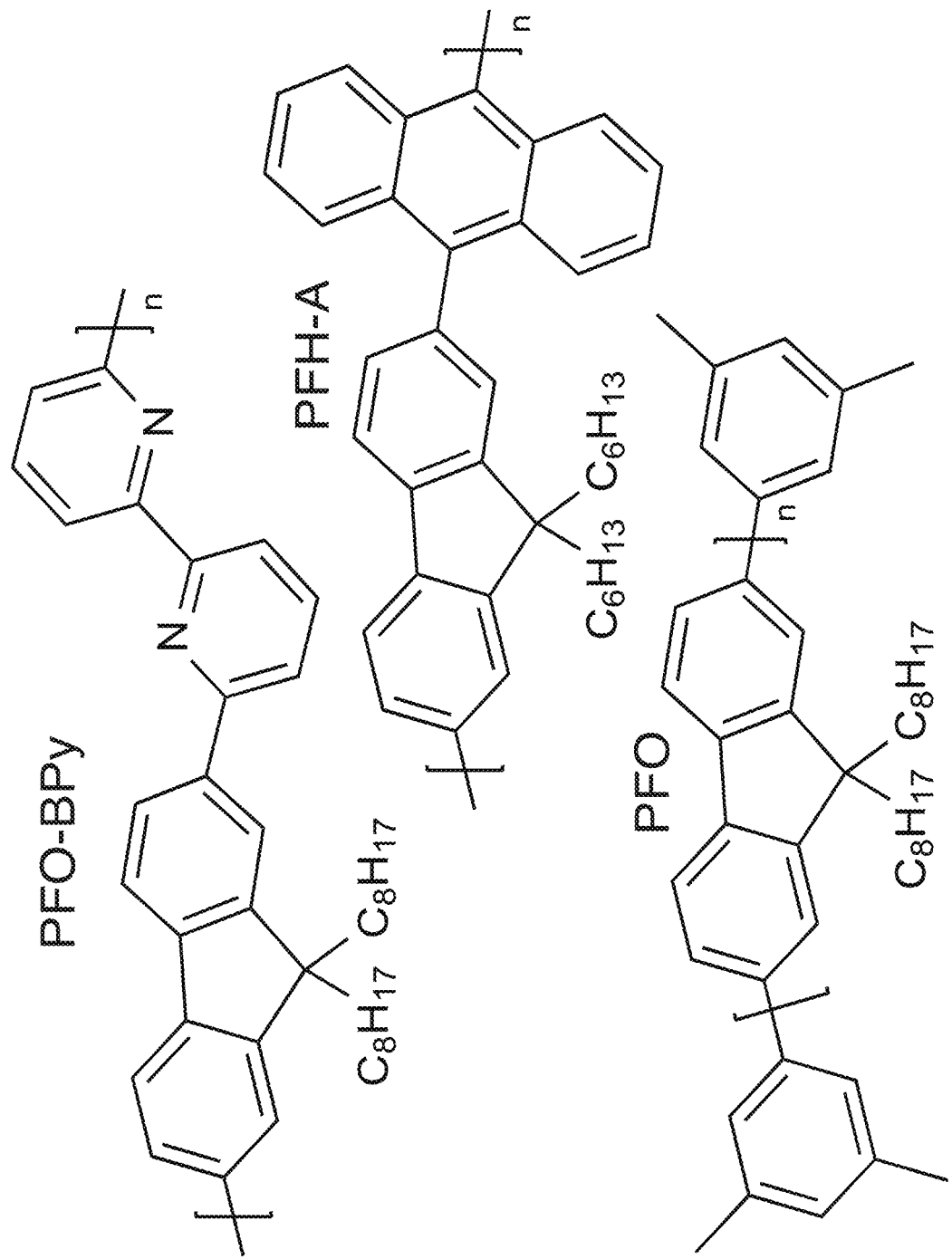
FIGS. 4(a)-4(d) show dispersions of enriched s-SWCNTs and deposition of well-coupled s-SWCNT thin films.
Figure 4B:
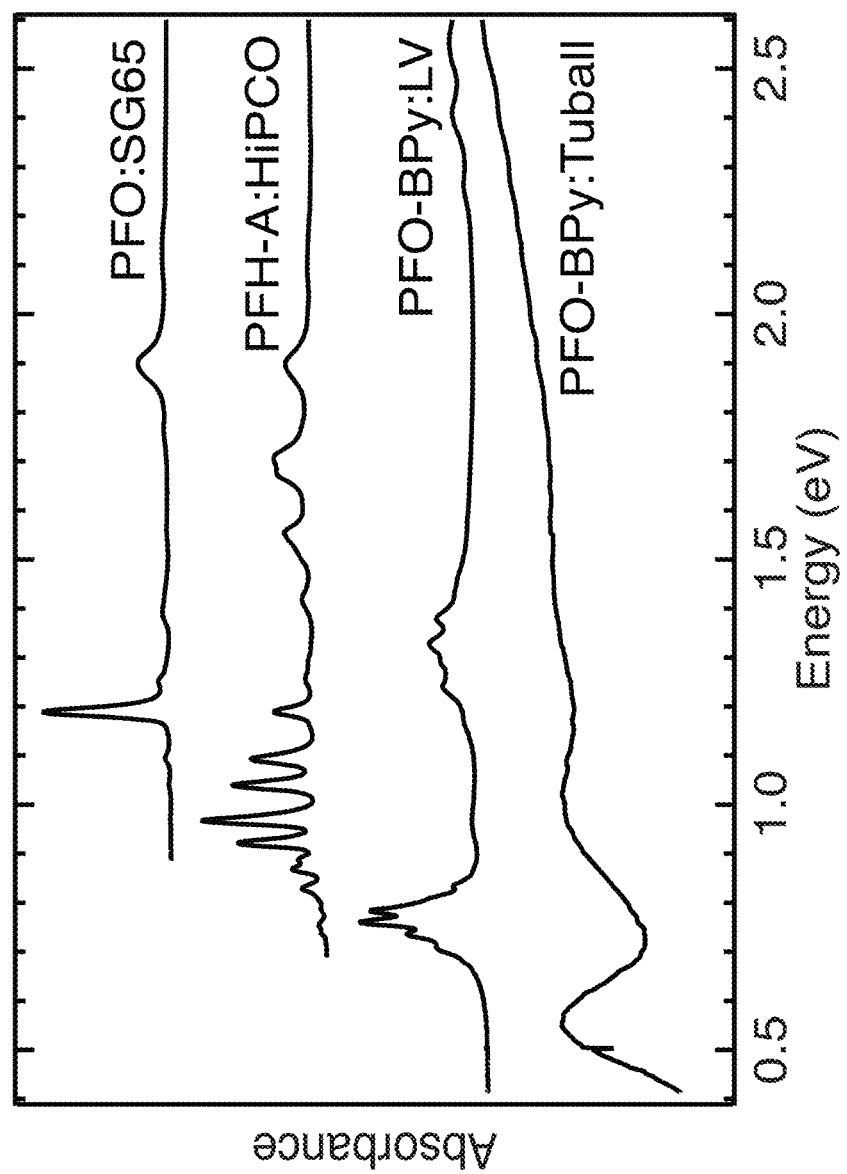
Figure 4C:
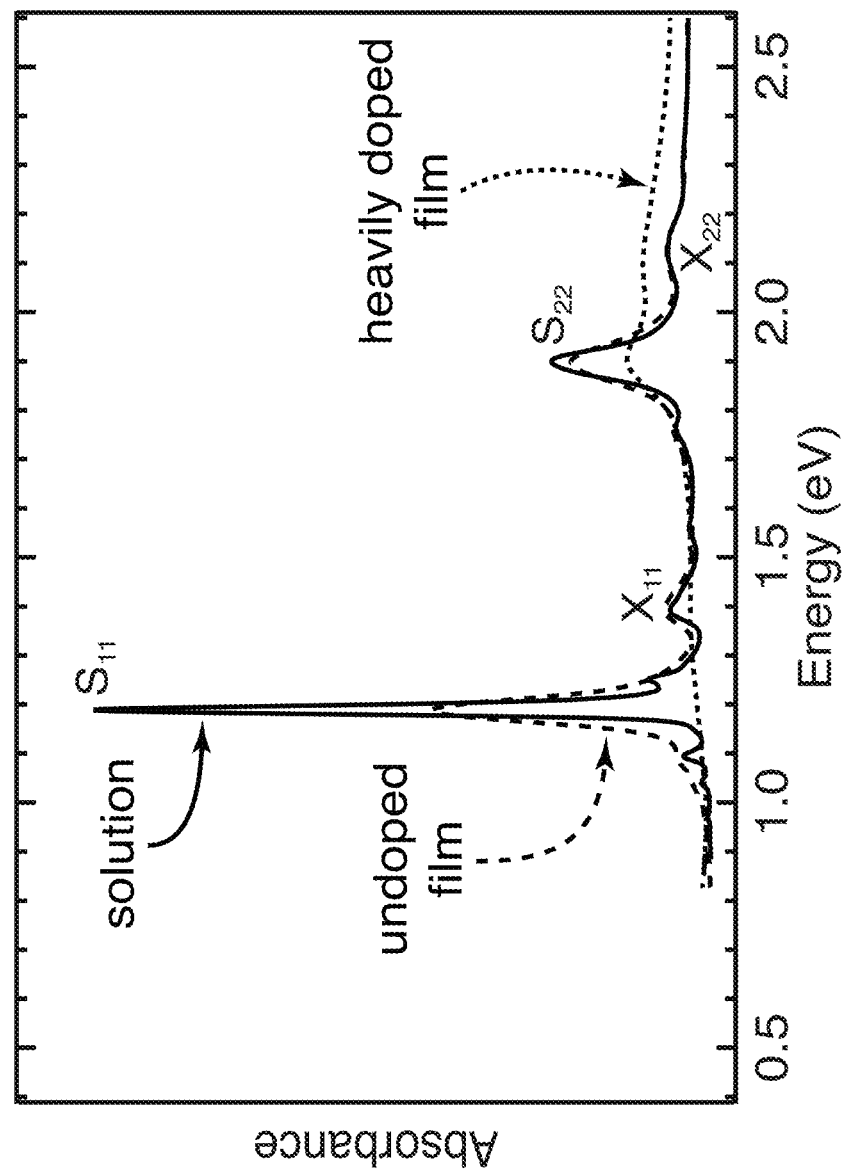
Figure 4D:
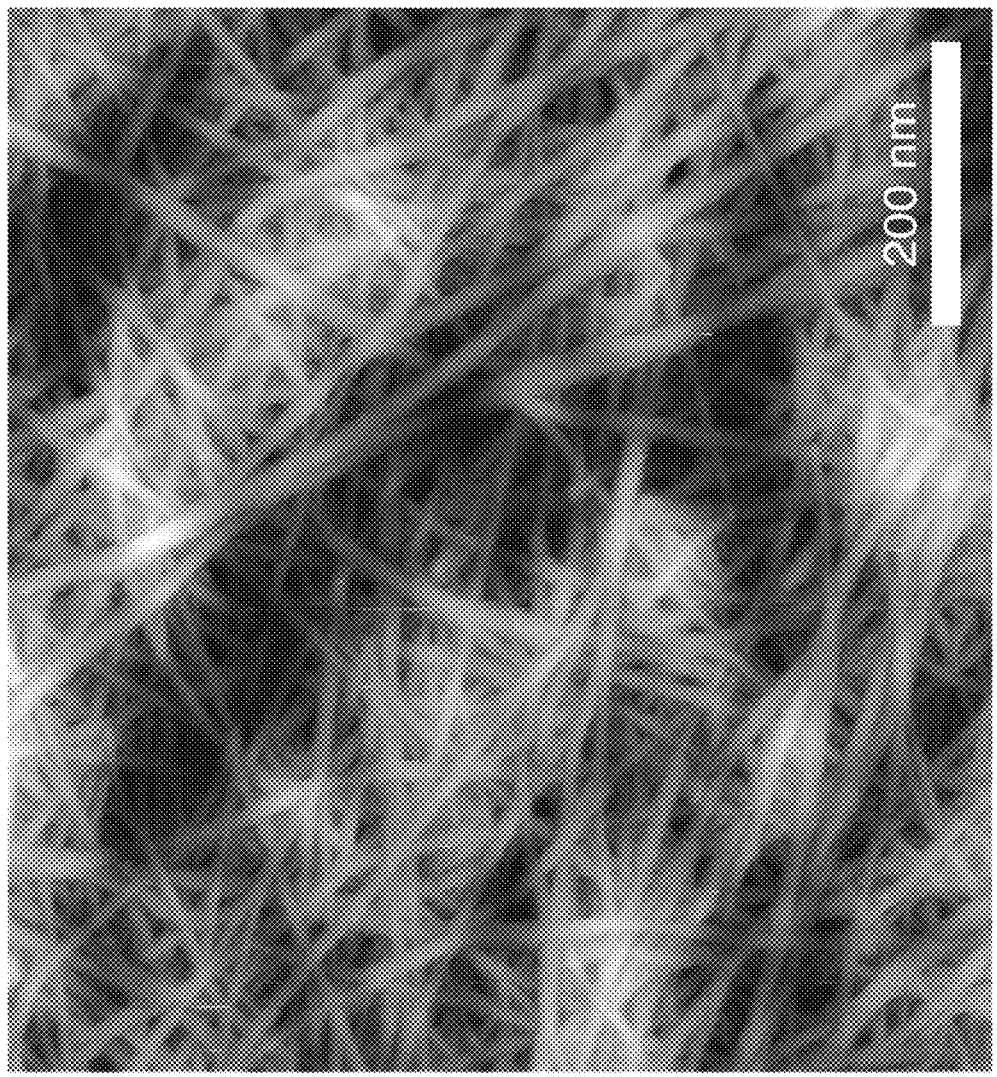

Exemplary embodiments of the invention provide highly tailored s-SWCNT thin films with finely controlled SWCNT chirality distribution and carrier density. FIGS. 4(a)-4(d) show dispersions of enriched s-SWCNTs and deposition of well-coupled s-SWCNT thin films. FIG. 4(a) shows chemical structures of three examples of fluorene-based polymers or co-polymers that may be used to disperse enriched s-SWCNTs. FIG. 4(b) shows representative absorbance spectra for PFO/SG65 (7,5), PFH-A:HiPCO, PFO-BPy:LV, and PFO-BPy:Tuball s-SWCNT dispersions, with average SWCNT diameters (electronic band gaps) of 0.8 nm (1.5 eV), 1.1 nm (1.1 eV), 1.3 nm (0.95 eV), and 1.8 nm (0.7 eV), respectively. FIG. 4(c) shows absorbance spectra of solution-phase and thin film samples of PFO/SG65 (7,5) s-SWCNT. The dotted line shows the absorbance spectrum of the thin film after heavy p-type doping by OA. FIG. 4(d) shows a representative topographic atomic force micrograph of a PFO-BPy/LV thin film. These absorbance measurements were performed on a Cary 500 spectrophotometer, with a step size of 2 nm and scan speed of 600 nm/min (equivalent to an integration time of 0.2 seconds per point). In the case of solution-phase measurements, a cuvette with blank solvent was used as the baseline. For film measurements, a blank glass slide was used as a baseline.

To generate enriched semiconducting samples, s-SWCNTs may be selectively extracted from polydisperse SWCNT soot using fluorene-based polymers or co-polymers, such as those shown in FIG. 4(a). Fluorene-based polymers and co-polymers have shown very high selectivity for s-SWCNTs, at equally impressive yield and throughput over a large range of diameters, with recent field effect transistor (FET) studies suggesting m-SWCNT impurity of levels of ≤0.02%. All samples shown in FIG. 4(b) exhibit m-SWCNT impurities that are essentially undetectable by absorbance and Raman spectroscopy, although these techniques do not allow for a quantitative estimate for the s-SWCNT purity level beyond approximately 99%.

For example, to prepare polymer:s-SWCNT dispersions, four different SWCNT source materials may be used: (1) SWCNTs synthesized by LV at a furnace temperature of approximately 1125° C.; (2) commercially obtained "SG65i" material synthesized from cobalt molybdenum catalysis of CoMoCAT®; (3) commercially obtained raw HiPCO® material synthesized by high-pressure disproportionation of CO; and (4) commercially obtained raw Tuball™ SWCNTs. The raw LV SWCNTs, HiPCO® SWCNTs, and Tuball™ SWCNTs are all presumed to contain metallic and semiconducting tubes in a roughly 1:3 ratio, whereas the CoMoCAT® material is enriched in s-SWCNTs and the (6,5) s-SWCNT in particular. The SWCNTs may be dispersed in a fluorene-based polymer or co-polymer solution generated by dissolving polymer in toluene at a concentration between 0.4-2 mg/mL. The polymers used may include poly[(9,9-dioctylfluorenyl-2,7-diyl)-alt-co-(6,6'-{2,2'-bipyridine})] (PFO-BPy), poly[(9,9-dihexylfluorenyl-2,7-diyl)-co-(9,10-anthracene)] (PFH-A), and/or poly(9,9-dioctylfluorenyl-2,7-diyl) (PFO). These fluorene-based polymers selectively wrap s-SWCNTs, allowing for a SWCNT dispersion with a less than 1% m-SWCNT impurity level. Although these three fluorene-based polymers select only semiconducting tubes, each polymer selects a different population of s-SWCNTs. PFO-BPy selects large diameter tubes with no preference for particular chiralities, PFH-A selects near-armchair s-SWCNTs and disperses a much narrower chirality distribution, and PFO selects only (7,5) tubes from the SG65i material even though the precursor material is predominantly composed of (6,5) s-SWCNTs. For further detail concerning the technique for generating high-yield dispersions of s-SWCNTs using a fluorene-based semiconducting polymer that selectively wraps semiconducting nanotubes with a range of large diameters, see Guillot, S. L. et al. Precision printing and optical modeling of ultrathin SWCNT/$C_{60}$ heterojunction solar cells. *Nanoscale* 7, 6556-6566 (2015) and Mistry, K. S., Larsen, B.

A. & Blackburn, J. L. High-Yield Dispersions of Large-Diameter Semiconducting Single-Walled Carbon Nanotubes with Tunable Narrow Chirality Distributions. *ACS Nano* 7, 2231-2239 (2013), the entire disclosures of which are incorporated by reference herein.

The diameter (or band gap) is determined by the synthetic conditions used to make the s-SWCNT networks. For example, polymers such as PFO, PFH-A, PFO-BPy, SMP, PF-PD, or similar fluorene-based polymers or co-polymers may be used to control which specific s-SWCNTs are selected from the raw starting material. The band gap may be controlled to have any suitable value. For example, for reasons discussed in further detail below, the band gap may be controlled to have a value between approximately 1.0 eV and approximately 1.2 eV. For example, the polymer PFH-A and the HiPCO® material may be used to achieve this band gap. The HiPCO® material contains a distribution of s-SWCNTs whose band gaps lie close to this range, and the chemical interactions between PFH-A and a specific subset of s-SWCNTs results in a sample enriched in s-SWCNTs with a band gap of approximately 1.1 eV. The subset of s-SWCNTs is determined by the choice of starting SWCNT material and the conjugated polymer. This combination may be determined by any suitable method, such as the method disclosed in Mistry, K. S., Larsen, B. A. & Blackburn, J. L. High-Yield Dispersions of Large-Diameter Semiconducting Single-Walled Carbon Nanotubes with Tunable Narrow Chirality Distributions. *ACS Nano* 7, 2231-2239 (2013), the entire disclosure of which is incorporated herein by reference.

Once the s-SWCNTs are dispersed in the polymer, the majority of the excess polymer may be removed during consecutive 20-hour ultracentrifuge runs until the solution reaches a mass ratio between 1:1 and 2:1 polymer:s-SWCNTs, which is determined after each centrifuge run from the absorption spectra of the solution using the Beer-Lambert Law A=εcl, where A is the absorbance, ε is the decadic molar extinction coefficient, c is the concentration, and l is the path length.

The high quality s-SWCNT networks shown in FIGS. 4(c) and 4(d) may be prepared by a suitable ultrasonic spray deposition technique, such as those described in Guillot, S. L. et al. Precision printing and optical modeling of ultrathin SWCNT/$C_{60}$ heterojunction solar cells. *Nanoscale* 7, 6556-6566 (2015) and Dowgiallo, A.-M., Mistry, K. S., Johnson, J. C. & Blackburn, J. L. Ultrafast Spectroscopic Signature of Charge Transfer between Single-Walled Carbon Nanotubes and $C_{60}$. *ACS Nano* 8, 8573-8581 (2014), the entire disclosures of which are incorporated by reference herein. In one example, the ultrasonic sprayer utilized a Sonotek 120 kHz Impact nozzle. Room temperature SWCNT ink was sprayed at 300 µl/min under nitrogen flowing at 7 std L/min with 0.8 Watt ultrasonic spray head power. The substrate was heated to 130±10° C. while spraying. The sprayed s-SWCNT films were soaked in toluene for 10-20 minutes at 78° C. to remove excess fluorene-based polymer or co-polymer. Film thickness was controlled by the concentration of the s-SWCNT ink and the number of sprayer passes, and was measured directly by atomic force microscopy (AFM) for the toluene-soaked films.

Figure 5A:
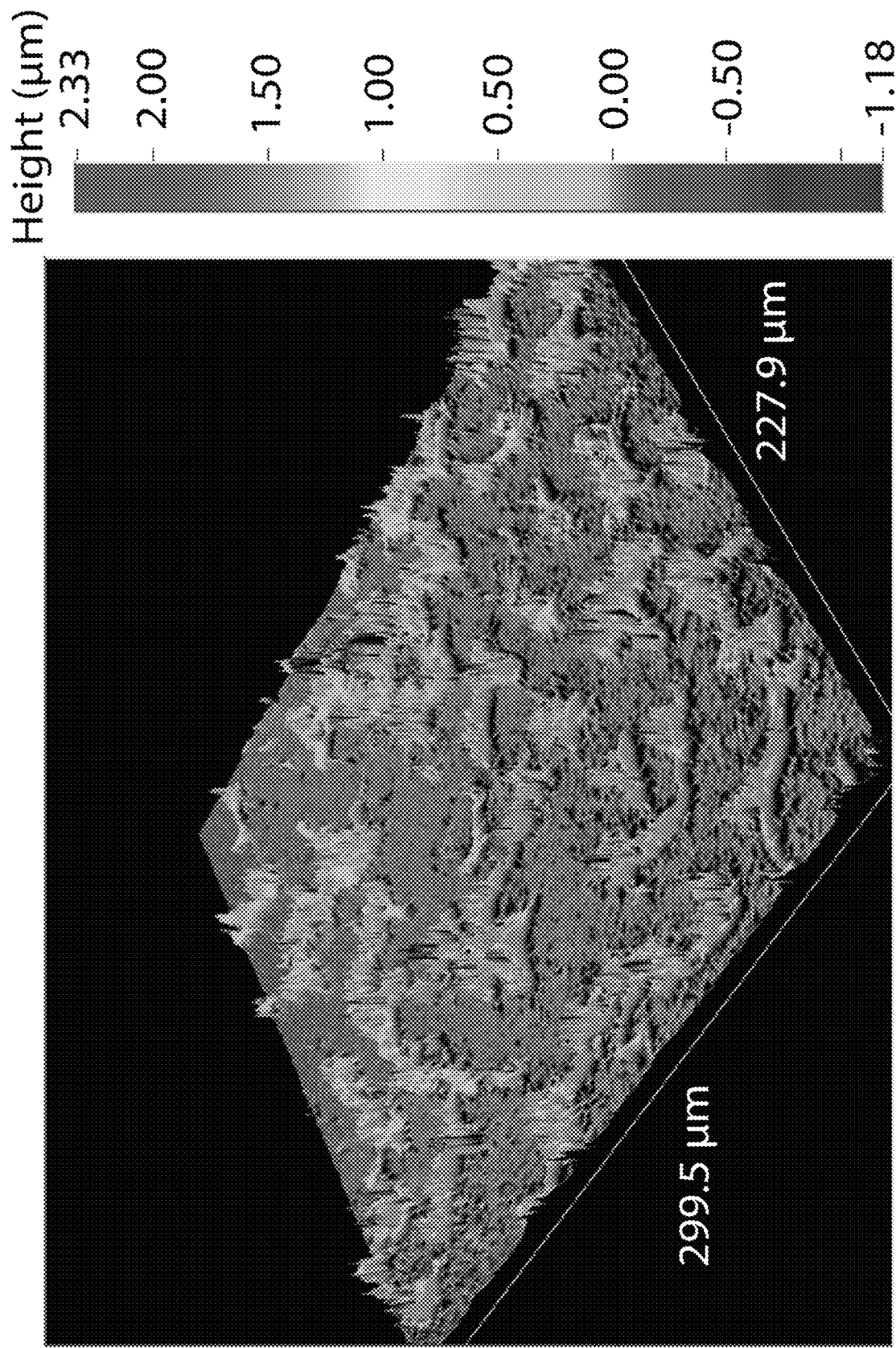
FIGS. 5(a)-5(d) show the surface topography of a typical laser vaporization (LV) film prepared by ultrasonic spraying from a PFH-A dispersion.
Figure 5B:
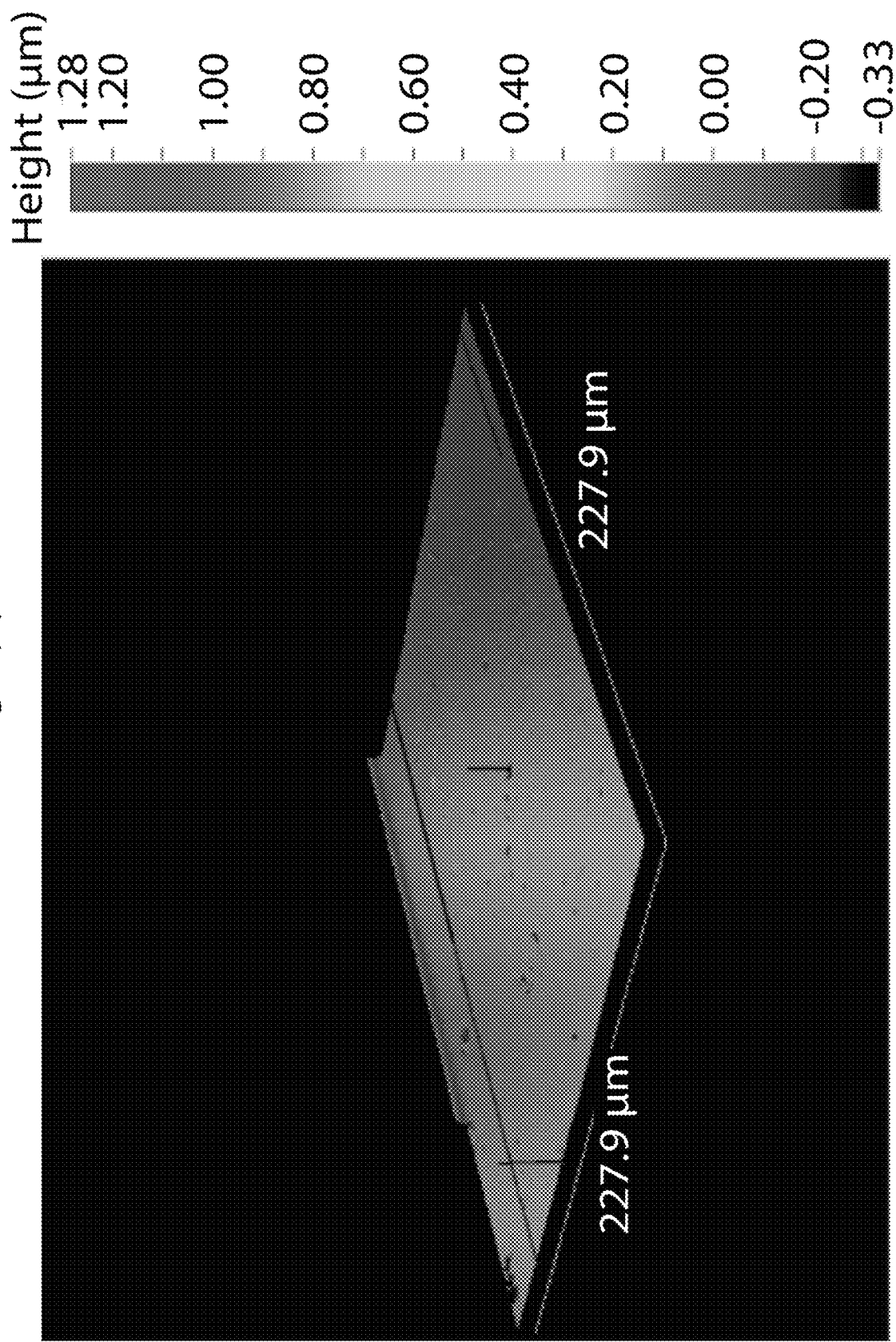
Figure 5C:
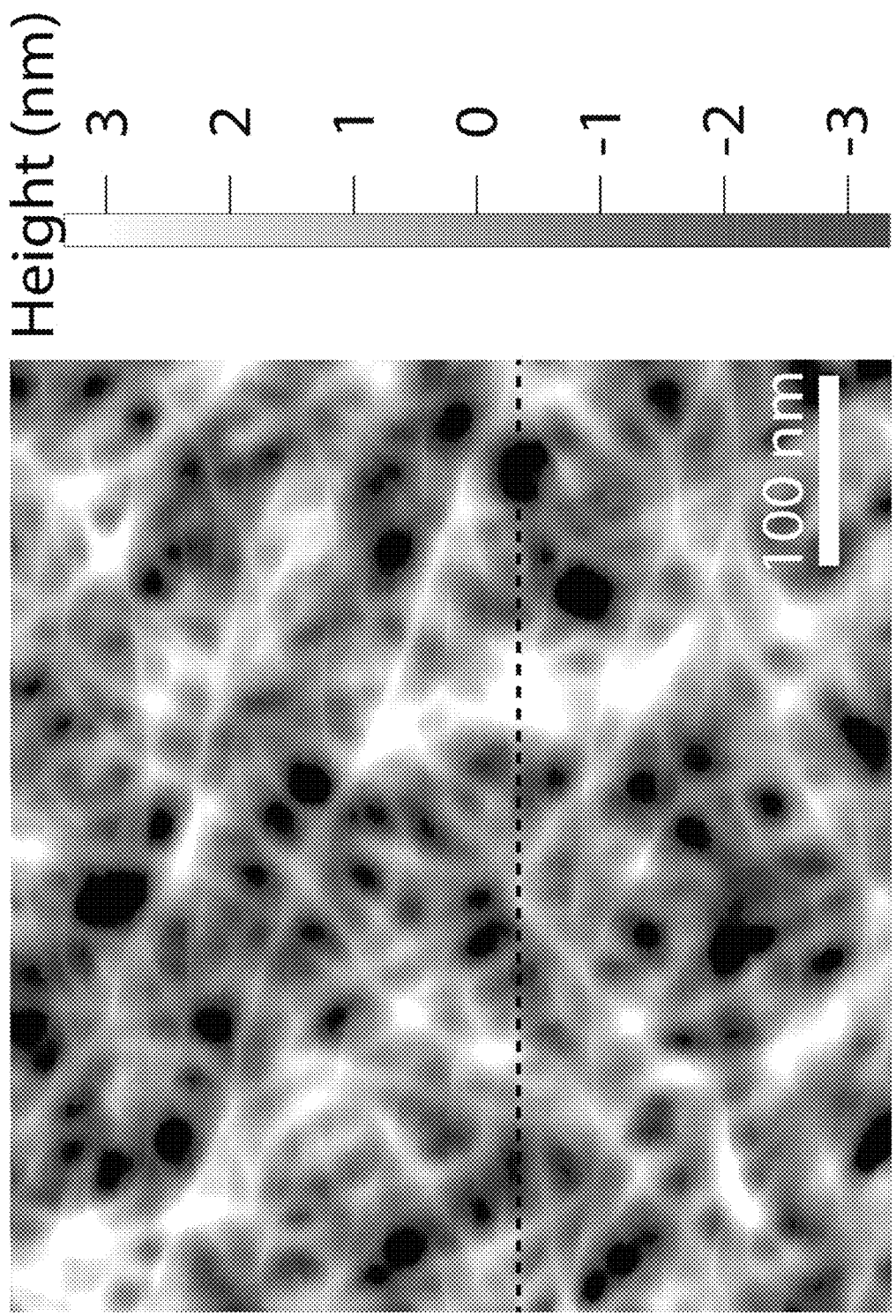
Figure 5D:
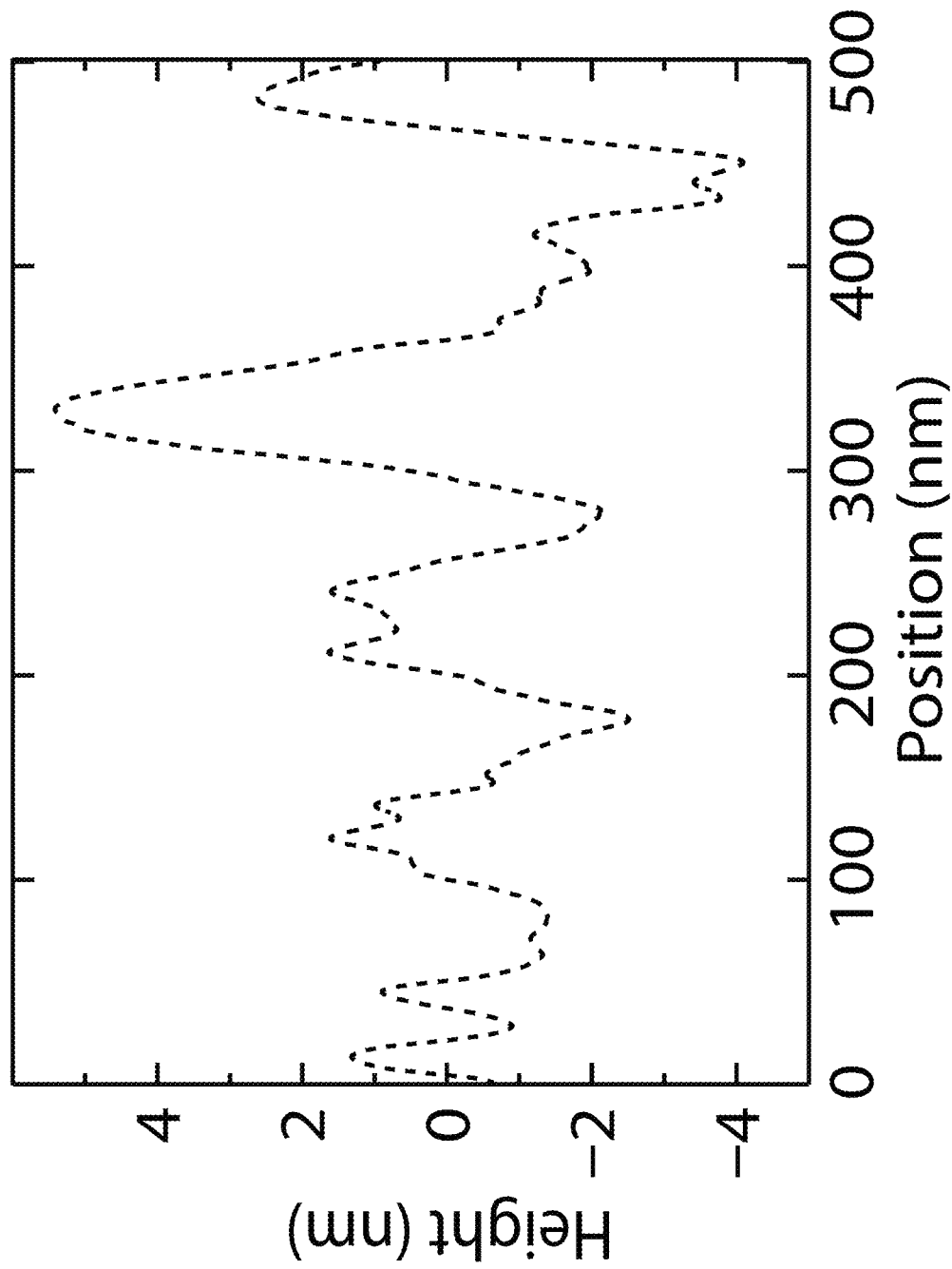

FIGS. 5(a)-5(d) show profilometry and AFM measurements of representative s-SWCNT films, and demonstrate that the films are uniform over large areas with low surface roughness. FIGS. 5(a) and 5(b) show optical micrographs before and after a toluene soak treatment, respectively. The as-deposited film in FIG. 5(a) exhibits severe surface roughness due to the accumulation of excess polymer, which can be removed by a hot toluene soak, leaving the very smooth film shown in FIG. 5(b). FIG. 5(c) shows an AFM micrograph of the surface of a s-SWCNT network after the toluene soak treatment. FIG. 5(d) shows a height profile determined for the dashed line shown in FIG. 5(c), indicating that the toluene treatment results in a smooth s-SWCNT network (root-mean-square surface roughness $R_q$<8 nm).

In the example discussed above, after the initial film deposition, a toluene soak removed excess fluorene-based polymer or co-polymer, leaving polymer wrapped s-SWCNTs in a mass ratio of approximately 1:1 polymer:s-SWCNTs, and enabling close physical contact and efficient electronic coupling between s-SWCNTs, as indicated by broadened exciton transitions such as those shown in FIG. 4(c). The films were subsequently fully doped by immersing in a solution of OA, which is a strong one-electron oxidant. In this example, to achieve full doping, the films were submerged in a concentrated solution of OA in DCE at 78° C. for a minimum of approximately 1 minute in a bath of greater than 1 mg/mL OA solution in DCE. However, any other suitable conditions, solution, and/or solvent may be used. Here, "full doping" is defined as the doping level at which further increases in the concentration and/or immersing time do not produce additional changes to the absorption spectrum or film conductivity.

The large density of holes (approximately $1 \times 10^{20}$ cm$^{-3}$ for a fully doped film) injected by adsorbed OA molecules strongly bleaches the exciton transitions of the s-SWCNTs, as shown by the dashed line labeled "heavily doped film" in FIG. 4(c), and dramatically increases the electrical conductivity σ of the film. The bleach, or reduction in the intensity, of the $S_{11}$ absorption band provides a qualitative indication of the carrier doping of the carbon nanotubes, where the magnitude of the bleach is dependent on the carrier doping density (i.e., larger carrier densities result in more pronounced bleaching). The relative bleach of the $S_{11}$ absorption band, $\Delta A/A_0$ ($S_{11}$), is given by:

$$\frac{\Delta A}{A_o}(S_{11}) = \frac{\text{Area}_{S_{11}}^{undoped} - \text{Area}_{S_{11}}^{doped}}{\text{Area}_{S_{11}}^{undoped}} \quad (5)$$

where $\text{Area}_{S_{11}}^{undoped}$ and $\text{Area}_{S_{11}}^{doped}$ are the areas under the $S_{11}$ absorption peak for the undoped and doped samples, respectively. Exemplary embodiments of the invention may correlate the shift in energy of the C1s peak, as measured by x-ray photoelectron spectroscopy, with a shift in the Fermi level, $\Delta E_f$, of the samples as a function of doping. This enables the correlation of $\Delta A/A_0$ ($S_{11}$) with $\Delta E_f$ (see FIG. 9(g) discussed below), and subsequent comparison of the experimentally measured Seebeck values with those predicted by DFT calculations discussed above as a function of a shift in the Fermi level (see FIG. 12(e) discussed below).

In this example, the thermopower (Seebeck) measurements were performed on a system that uses copper (Cu) blocks for temperature control and making electrical contact to the film. Indium pads were first pressed onto the s-SWCNT films to ensure good Ohmic and thermal contact to the Cu blocks. The spacing between the Cu blocks was 4 mm, so the minimum possible spacing between the indium pads was approximately 6 mm. However, the typical spacing between the indium pads (for greater than 90% of the measurements) employed in this example is approximately 16-20 mm. Resistive heaters connected to each of the blocks produced the temperature gradient, which was measured by a differential thermocouple. At least four different temperature gradients (between −3 and +3 K) were measured for each sample, with the slope of the best-fit line for these points being used for the reported thermopower α, corrected for the contributions of all other components of the electrical circuit (i.e., the Seebeck voltage due to the copper/indium contacts). Based on the physical dimensions of the system, the estimated error in the thermopower α reported by the system was less than 10%.

While it is difficult to directly correlate $\Delta A/A_0(S_{11})$ with the actual carrier density within the s-SWCNT film for a broad range of injected carrier densities, the carrier density may be estimated within a fully doped film based on the approximate size of the exciton. To fully bleach the $S_{11}$ exciton, the carrier density (per unit length of SWCNT) will be such that there is approximately one hole per unit length $L_{cor}$, where $L_{cor}$ is the correlation length or exciton size. $L_{cor}$ has been determined to be in the range of approximately 2 nm, so full $S_{11}$ bleaching occurs for hole densities in the range of approximately 0.5 $nm^{-1}$. The absorbance cross section of (7,5) SWCNTs has been estimated experimentally to be in the range of approximately $1.6 \times 10^{17}$ $cm^2/C$ atom, and the number of atoms per nanometer of SWCNT can be determined geometrically to be $[119.7 \times d_{(n,m)}]$, where $d_{(n,m)}$ is the diameter of the carbon nanotube with an (n,m) chiral index. Using the absorbance coefficient of the films and a full-packed SWCNT density (for (7,5) SWCNTs) of approximately 1.12 $g/cm^3$, the films can be estimated to have a density of approximately 0.42 $g/cm^3$ (approximately 40% filling fraction). Since (7,5) SWCNTs have approximately 99 C atoms/nm, this density translates to a carrier density of approximately $1 \times 10^{20}$ holes/$cm^3$ for a fully doped s-SWCNT thin film.

Multiple control experiments demonstrate that the remaining fluorene-based polymer or co-polymer in the s-SWCNT networks does not contribute to the measured electrical conductivity σ. A comparison was performed of the basic charge transport properties of polymer-wrapped LV s-SWCNT films with the transport properties of LV SWCNT films prepared without fluorene-based polymers or co-polymers. To prepare SWCNT films according to exemplary embodiments of the invention, SWCNTs that are dispersed with carboxymethyl cellulose (CMC) in aqueous suspension may first be spray-coat mixed (⅓ metallic, ⅔ semiconducting). The CMC may then be digested from the film with nitric acid, leaving a well-connected network of heavily p-type SWCNTs devoid of residual polymer. The typically reported figures of merit are plotted for these transparent SWCNT films, the optical transmittance at 550 nm (T550) and sheet resistance ($R_{sh}$ in Ω/sq.) in FIG. 6. In this example, the sheet resistance of the polymer:s-SWCNT networks was measured using a four-point probe (1 mm probe spacing). The accuracy of the measurement was determined using a calibrated indium-doped tin oxide sample with a sheet resistance of approximately 14 Ω/sq. The sheet resistance was converted to electrical conductivity σ (in S $m^{-1}$) by utilizing the film thickness as measured by AFM.

Figure 6:
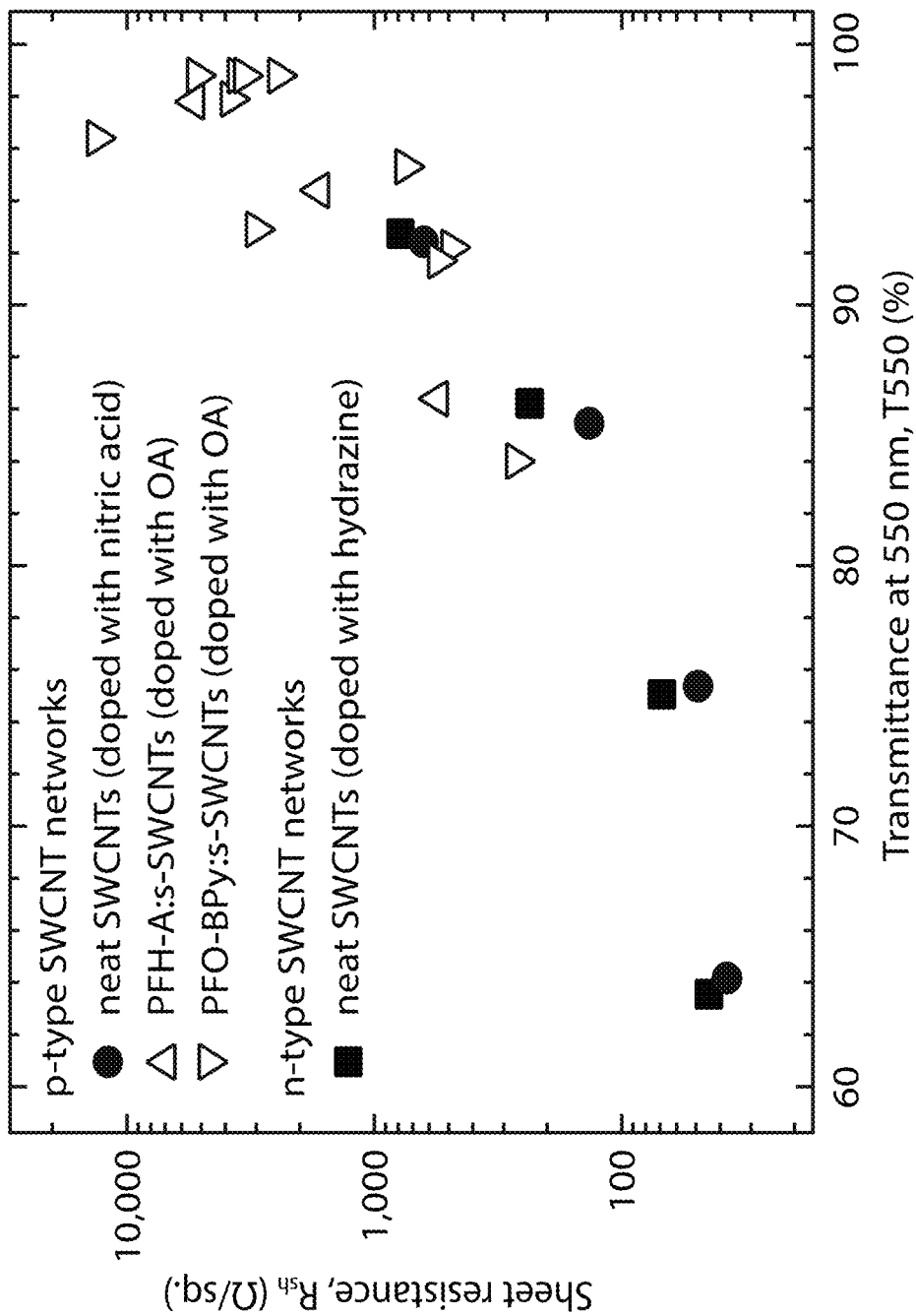
FIG. 6 shows a comparison of the optoelectronic properties of doped polymer:LV s-SWCNT networks with doped pristine SWCNT networks.

FIG. 6 shows a comparison of the optoelectronic properties of doped polymer:LV s-SWCNT networks with doped pristine SWCNT networks. The sheet resistance versus transmittance (measured at λ=550 nm) for a variety of doped SWCNT films is provided. The circles and squares represent films sprayed from aqueous dispersions utilizing carboxymethyl cellulose (CMC) as a dispersant. Following deposition, the CMC may be completely digested by nitric acid. Black circles are measurements on p-type doped films taken immediately after this nitric acid soak and grey squares are for films that are subsequently doped n-type with hydrazine. Upright and inverted triangles are for films prepared from either PFH-A or PFO-BPy dispersions, respectively. Following ultrasonic spray deposition, the films may be soaked in toluene to remove excess polymer and then doped strongly p-type by immersing the films in greater than 2 mg/ml OA in dichloroethane (DCE) at 78° C.

The $T550/R_{sh}$ values for heavily doped LV s-SWCNT networks employing both PFH-A and PFO-BPy polymers follow the same trend as the p-type films prepared according to the CMC process. This correlation suggests that the fluorene-based polymer or co-polymer does not enhance hole transport within the p-type s-SWCNT films. The temperature-dependent resistance of heavily doped polymer-wrapped LV s-SWCNT films was also compared to that of SWCNT films prepared without fluorene-based polymer or co-polymer (not shown). In all cases, the resistance decreases with increasing temperature, indicating a thermally activated conduction mechanism that was previously ascribed to barriers associated with tube-tube junctions. Taken together, these experiments help to confirm that the electrical properties measured in FIGS. 12(a)-12(f) (discussed below) are not appreciably enhanced by the fluorene-based polymer or co-polymer, and instead result from the intrinsic properties of the s-SWCNTs in the film, namely the SWCNT electronic structure, dopant-controlled Fermi level, and inter-tube potential barriers.

Figure 7D:
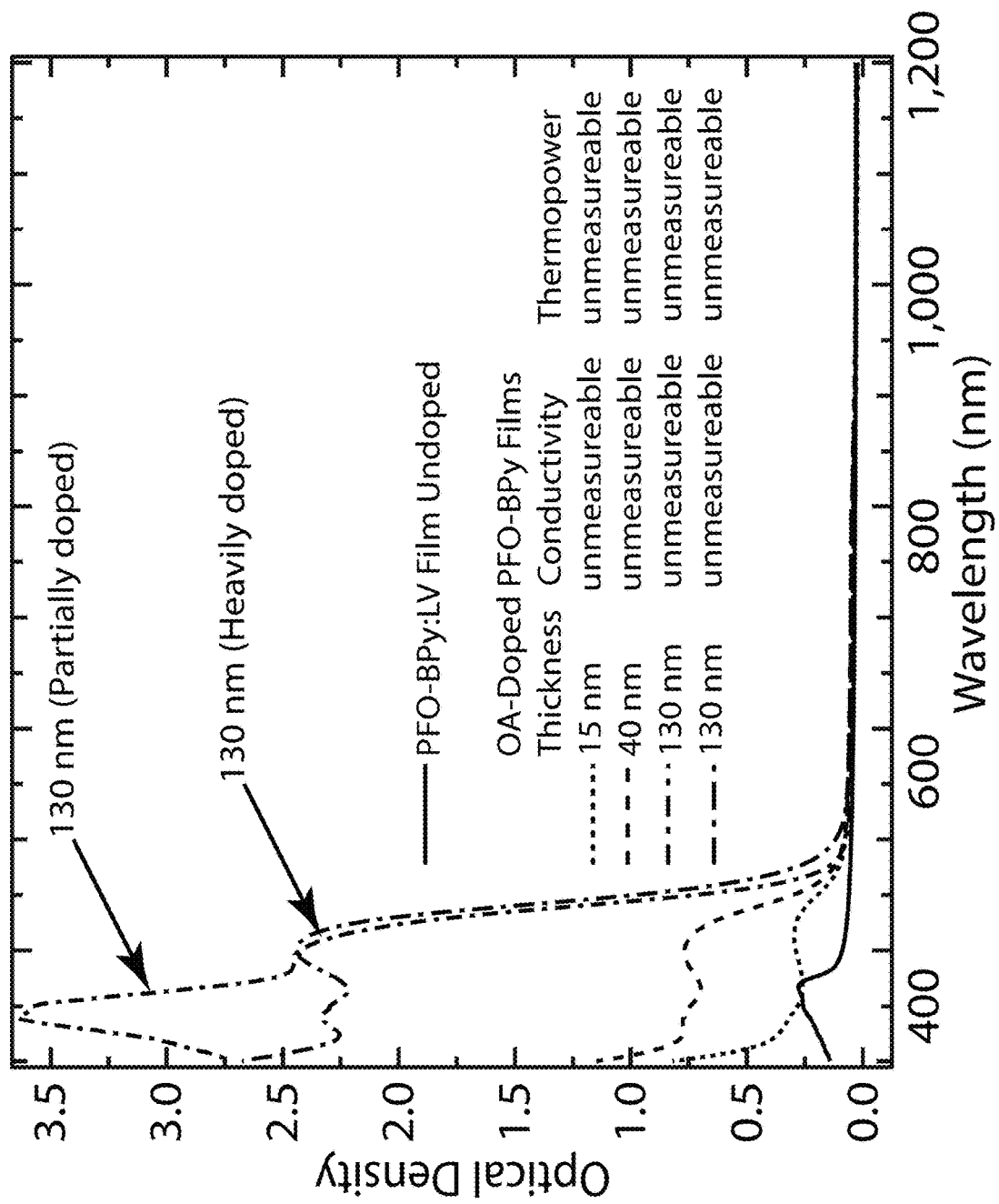
FIGS. 7(a)-7(c) show a comparison of absorbance spectra for undoped and heavily doped polymer:LV networks and polymers in dichloroethane (DCE) solution.

At very high doping densities of the polymer:s-SWCNT networks there is also a decrease in the intensity of the lowest energy absorption band attributed to the polymer, and the appearance of a red-shifted shoulder in the absorption spectrum. FIGS. 7(a)-7(d) show that these observations can be attributed to p-type doping of the polymer, since co-dissolving the OA dopant into a DCE solution of the polymer (both for PFH-A and PFO-BPy) gives rise to the same spectral features. FIGS. 7(a)-7(d) show a comparison of absorbance spectra for undoped and heavily doped polymer:LV networks and polymers in DCE solution. FIG. 7(a) shows PFH-A in DCE and PFH-A:LV films, while FIG. 7(b) shows PFO-BPy in DCE and PFO-BPy:LV films. Both the polymer:LV films and the solution-phase polymer are doped heavily by OA. The arrows point to the dominant PFH-A polaron peak that can be seen in the region of the $S_{33}$ SWCNT transitions in the doped s-SWCNT film. FIG. 7(c) shows a comparison of undoped and doped PFO-BPy films. FIG. 7(d) shows the absorbance of doped PFO-BPy films of varying thickness. The legend indicates that the transport properties for all samples are unmeasureable.

These control experiments were carried out in the solution phase to avoid complications arising from spectral features due to interchain interactions in the solid state. FIG. 7(c) shows that similar results are observed for heavily doped neat PFO-BPy films when the polymer forms a predominantly amorphous solid-state structure. FIG. 7(d) indicates that the observed spectral features for heavily doped films are independent of the PFO-BPy film thickness, spanning thicknesses similar to the polymer:s-SWCNT networks. However, the neat PFO-BPy films have significantly more polymer than the polymer:s-SWCNT networks (e.g., 10-20 times for the 130 nm thick PFO-BPy film), since the polymer chains are densely packed. All attempts to measure the electrical conductivity σ of these doped PFO-BPy films were unsuccessful, even for the thickest film that would be expected to have the lowest sheet resistance.

To rationalize the doping behavior of the fluorene-based polymers or co-polymers, the valence level offsets between a model system are considered: PFO and the (7,5) s-SW-CNT. Schuettfort, T., Nish, A. & Nicholas, R. J. Observation of a Type II Heterojunction in a Highly Ordered Polymer-Carbon Nanotube Nanohybrid Structure. Nano Lett. 9, 3871-3876 (2009) estimated the valence level offset to be approximately 500 meV for the (7,5) SWCNT. From Bindl, D. J. et al. Free Carrier Generation and Recombination in Polymer-Wrapped Semiconducting Carbon Nanotube Films and Heterojunctions. J. Phys. Chem. Lett. 4, 3550-3559 (2013), the (9,7) ionization potential has been estimated to be in the range of 5.18 eV. Taking into account the difference in electronic band gaps of the (9,7) and (7,5) SWCNTs, this places the ionization potential of the (7,5) SWCNT in the range of approximately 5.36 eV. Janietz, S. et al. Electrochemical determination of the ionization potential and electron affinity of poly(9,9-dioctylfluorene). Appl. Phys. Lett. 73, 2453-2455 (1998) finds an ionization potential of approximately 5.8 eV for PFO. This translates to an estimated offset of approximately 440 meV between the (7,5) SWCNTs and PFO. This offset would grow to approximately 600 meV for the LV SWCNTs in this example.

This implies that the polymer is not significantly doped (i.e., exhibits negligible absorption features due to polaron formation) until fairly large shifts occur in the Fermi level ($\Delta E_F$>approximately 500 meV). This doping of the polymer can be observed in two ways. Firstly, the absorbance spectra shows that the fluorene-based polymers are doped by OA at high surface concentrations of OA, i.e. the highest doping levels as shown in FIGS. 9(a) and 9(b) discussed below, and FIGS. 8(a) and 8(b) discussed below. This is evidenced by a reduction in the oscillator strength of the polymer absorption in the range of 400 nm and the growth of new features at longer wavelengths that correspond to the positive polaron absorption of the hole-doped polymers.

The doping of the polymer can also be seen by a sudden change in the FWHM in the XPS C1s peak. In one example, core-level and work function XPS measurements were performed. The XPS core-level peaks were calibrated using a cleaned gold (Au) standard, which includes measuring the Fermi level and core-levels of Au. The core-level spectra were collected with a pass energy of 11.85 eV and a step size of 0.10 eV. This gives an uncertainty in the peak position of ±0.05 eV. The work function was determined by analyzing the secondary-electron cutoff region of the spectrum. Since this is a photon-energy independent measurement, the secondary-electron spectra were calibrated using ultraviolet photoelectron spectroscopy of Au, which captures both the Fermi-edge and secondary-electron cutoff region in one calibration scan. These measurements were taken with a pass energy of 2.95 eV and a step size of 0.025 eV. This gives an uncertainty in the work function of ±0.025 eV. The XPS measurements were performed under ultra-high vacuum (UHV) conditions (10-10 Torr). The samples did not exhibit signs of X-ray damage or sample charging during the XPS measurements (each sample was under vacuum for less than 30 mins).

Figure 8A:
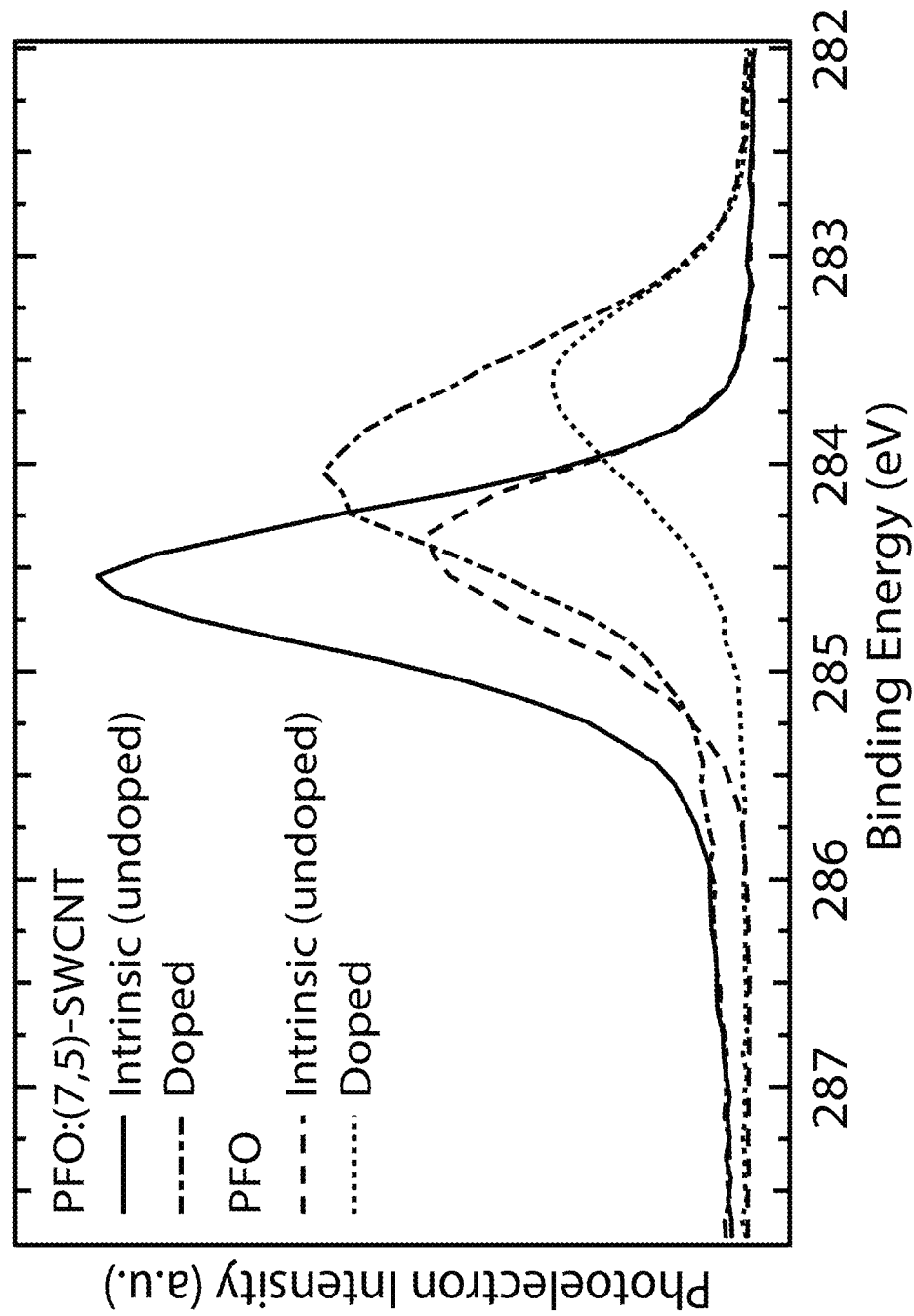
FIGS. 8(a) and 8(b) show x-ray photoelectron spectra (XPS) of undoped and heavily doped poly(9,9-dioctylfluorenyl-2,7-diyl) (PFO):(7,5) s-SWCNT networks and PFO films.
Figure 8B:
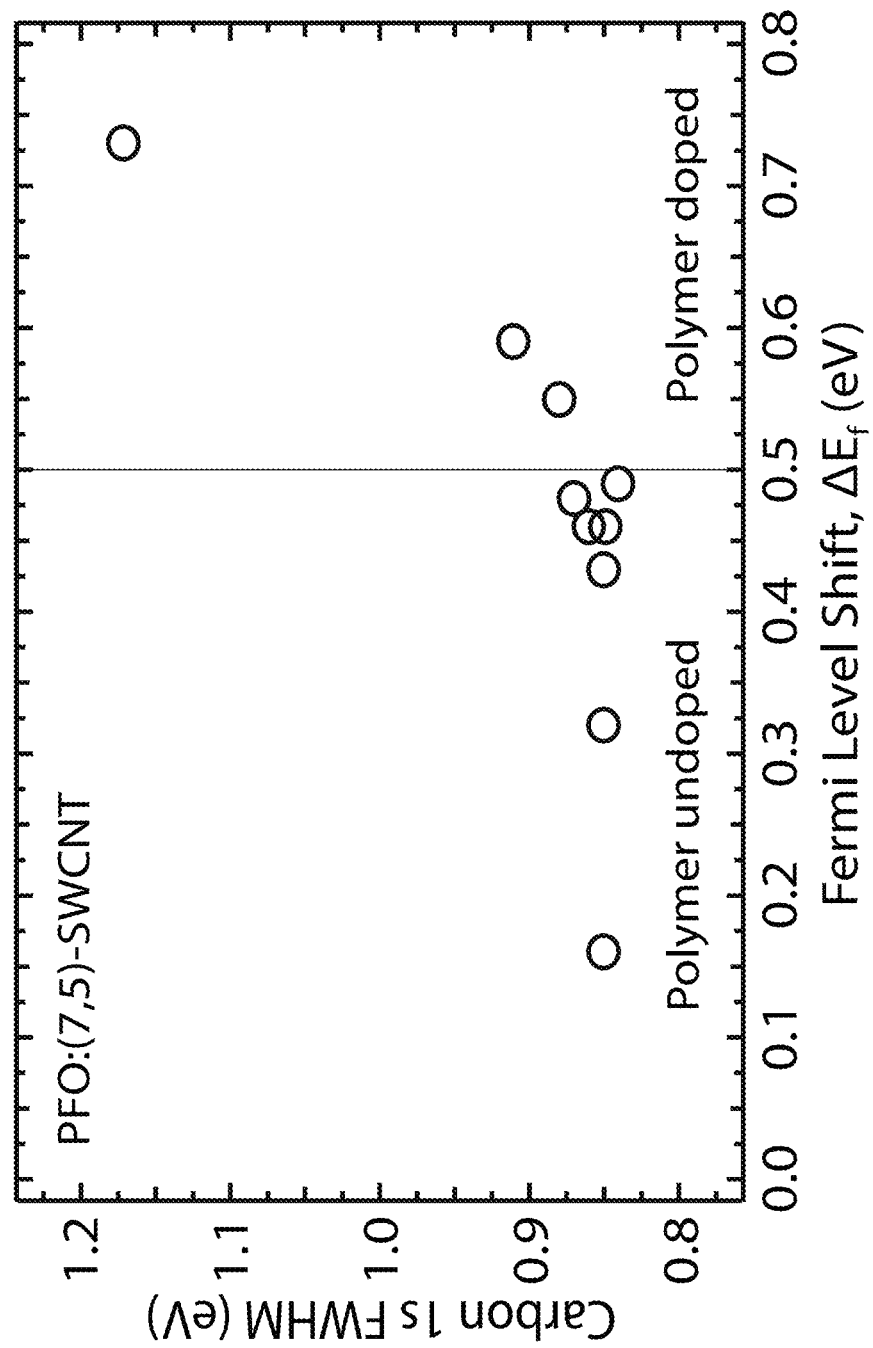
Figure 9B:
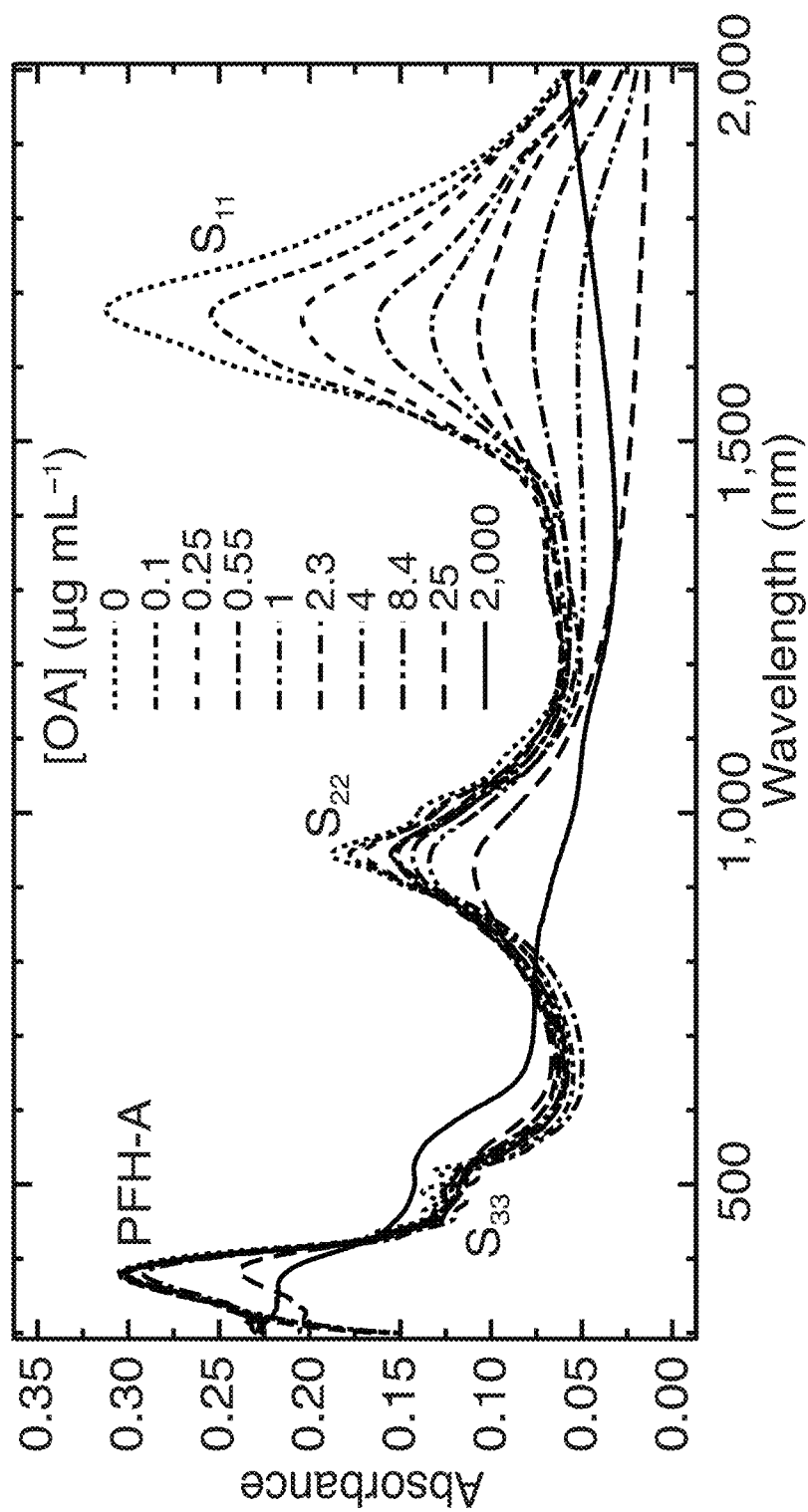

FIGS. 8(a) and 8(b) show XPS of undoped and heavily doped PFO:(7,5) s-SWCNT networks and PFO films. FIG. 8(a) shows XPS of intrinsic and heavily OA-doped PFO or PFO/(7,5). The PFO spectra demonstrate that the C1s spectrum of the PFO/(7,5) sample has a small contribution to the PFO C1s peak, and that at high doping, the PFO peak is shifted by the same amount as the SWCNT peak (approximately 0.6 eV), although the signal within the PFO/SWCNT film is dominated by the s-SWCNTs. Since core electron energies in the XPS measurement are referenced to the energy of the Fermi level (EF), this large red shift in C1s energy (EC1s) results directly from a shift of EF ($\Delta$EF) towards the valence band (p-type doping). Interestingly, a similar energetic shift is found for the Cl XPS peaks with increasing Cl:C ratio, but with an opposite sign to the shift observed for the C 1s spectrum. In contrast, no shift occurs for the Sb XPS peaks. These observations suggest that the primary charge transfer complex formed in the OA doping process involves a complex between the SWCNT sidewall and Cl atoms.

Note that the FWHM of the fully doped SWCNT/PFO film in FIG. 8(a) is broader than that of the undoped film. FIG. 8(b) shows the dependence of the C1s FWHM as a function of the shift in Fermi level. Note that the FWHM is roughly constant at approximately 0.85 eV until it abruptly increases once the Fermi level is shifted by greater than approximately 500 meV. This Fermi level shift is in line with the valence level offset of approximately 440-500 meV estimated above for the (7,5)/PFO HOMO levels.

As discussed above, exemplary embodiments of the invention control the carrier density and Fermi energy of s-SWCNT films. Exemplary embodiments of the invention may perform p-type doping of polymer:s-SWCNT networks by immersing networks in a solution of OA in DCE, modifying a procedure described in Chandra, B., Afzali, A., Khare, N., El-Ashry, M. M. & Tulevski, G. S. Stable Charge-Transfer Doping of Transparent Single-Walled Carbon Nanotube Films. Chem. Mater. 22, 5179-5183 (2010), the entire disclosure of which is incorporated by reference herein. The procedure described in Chandra attempts to achieve a maximum (or saturated) doping level. In contrast, exemplary embodiments of the present invention provide control over the doping level within the s-SWCNT network. For example, as discussed below, the desired doping level may be chosen to optimize the TE power factor $\alpha^2\sigma$ of the s-SWCNT network.

In one exemplary embodiment of the invention, the doping level of the s-SWCNT network may be controlled by first saturating the doping level of the s-SWCNT network, such that the s-SWCNT network is fully doped, and then removing charge carriers from the s-SWCNT network to reach the desired doping level. For example, the saturating may include a single step of immersing the s-SWCNT network in a concentrated OA solution at approximately 78° C. for at least approximately 1 minute. The OA solution may have a concentration greater than approximately 1 mg/mL, and the solvent may be DCE or any other appropriate solvent. Alternatively, the saturating may include a plurality of steps of immersing the s-SWCNT network in OA solutions having various immersion times, concentrations, and/or temperatures. In general, concentrations of OA above approximately 1 mg/mL lead to very heavy doping, essentially fully quenching the $S_{11}$ SWCNT optical transition, and partial to full quenching of the $S_{22}$ and polymer optical transitions, as shown in FIGS. 7(a)-7(c). After full doping has been reached, the doping level is then decreased (i.e., the s-SWCNT network is de-doped) by removing part of the OA from the s-SWCNT network. This may be accomplished by immersing the s-SWCNT network in a suitable solvent, such as acetone or DCE, and may include a single step or a plurality of steps having various immersion times, concentrations, and/or temperatures. For example, fully doped films may be incrementally de-doped by submersion in acetone from 1 second to 20 minutes at temperatures of 25° C. or 56° C. To reach very low doping levels, the acetone may be exchanged every 5 minutes during the hot acetone bath.

For example, for the Solid SPR sample discussed below, full doping is achieved by immersion in a 3 mg/mL solution of OA in DCE at 78° C. for 10 minutes, affording a TE power factor of ~150 μW m$^{-1}$ K$^{-2}$. A peak TE power factor of approximately 340-350 μW m$^{-1}$ K$^{-2}$ is then achieved by immersion of the fully doped sample in acetone at room temperature for between 1 and 3 minutes.

In another exemplary embodiment of the invention, the doping level may be controlled by adding the dopant until the desired doping level is reached. This may be performed in one or more steps. For example, the adding of the dopant may include a single step of immersing the s-SWCNT network in an OA solution until the desired doping level is reached, or a plurality of steps of immersing the s-SWCNT network in OA solutions having increasing concentrations until the desired doping level is reached. Concentrations of OA as low as approximately 1-5 ng/mL may be used to achieve very low doping levels. For example, a peak TE power factor of approximately 100 μW m$^{-1}$ K$^{-2}$ can be obtained for a PFH-A:LV s-SWCNT network by immersion of the undoped film in a solution of OA at concentrations between 1 and 8.4 μg/mL in DCE at 78° C. for 10 minutes.

After the desired doping level has been achieved, the film may be immersed for no more than approximately 3 seconds in acetone in order to remove excess OA and byproducts.

FIG. 9(a) shows absorbance spectra of PFO:SG65 (7,5) s-SWCNT) thin-film networks as a function of p-type doping with OA, and FIG. 9(b) shows absorbance spectra of PFH-A:LV s-SWCNT thin-film networks as a function of p-type doping with OA. The legends within FIGS. 9(a) and 9(b) identify the concentration of the OA solution used to achieve the observed bleaching level. An increase in hole density on the s-SWCNTs initially results in a bleach of the first exciton (S$_{11}$) absorption transition, followed by bleaching of the second exciton (S$_{22}$) absorption transition at higher carrier concentrations. The PF polymers are not appreciably doped until very high surface concentrations of OA, as shown by the bleach of the singlet absorption peaks in FIGS. 9(a) and 9(b), and new polaron absorbance features at very high OA concentrations as shown in FIGS. 3(a)-3(d).

Figure 9C:
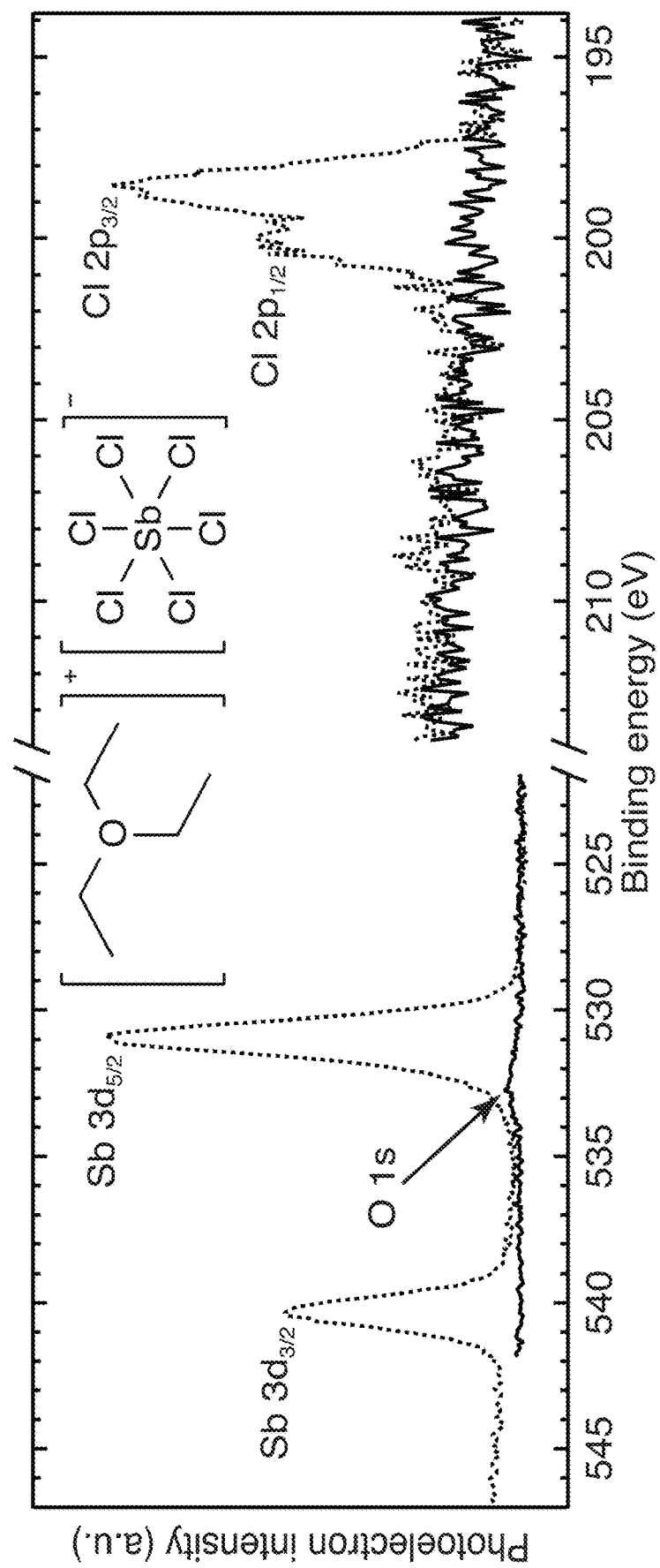
Figure 9E:
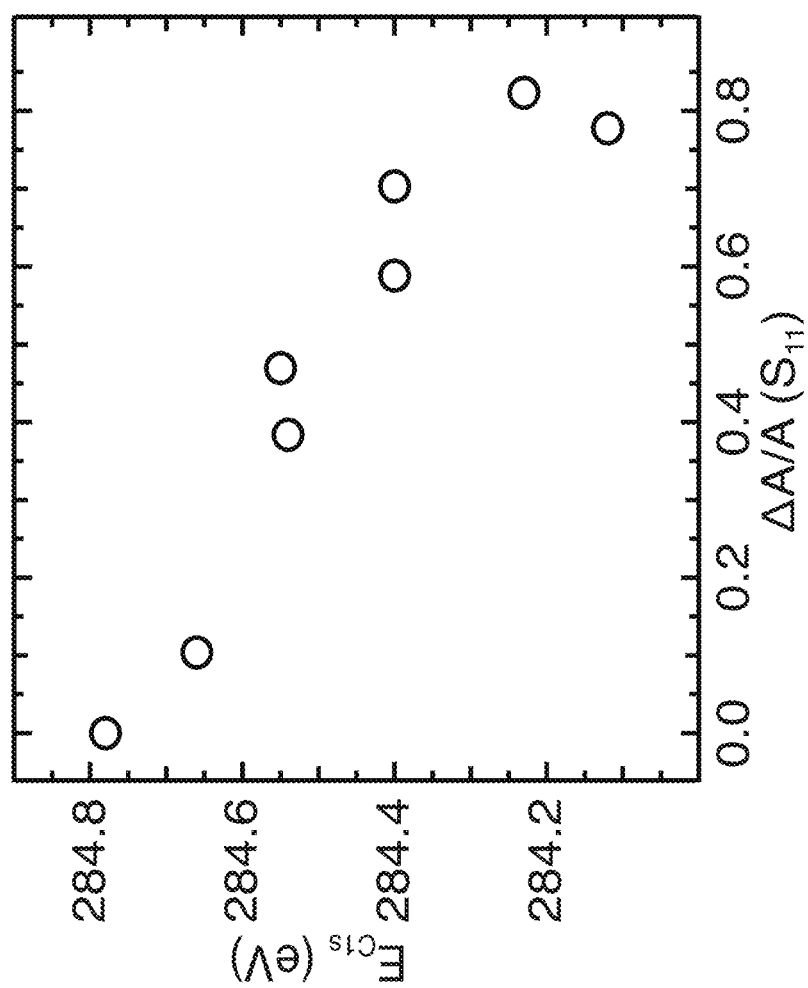
Figure 9F:
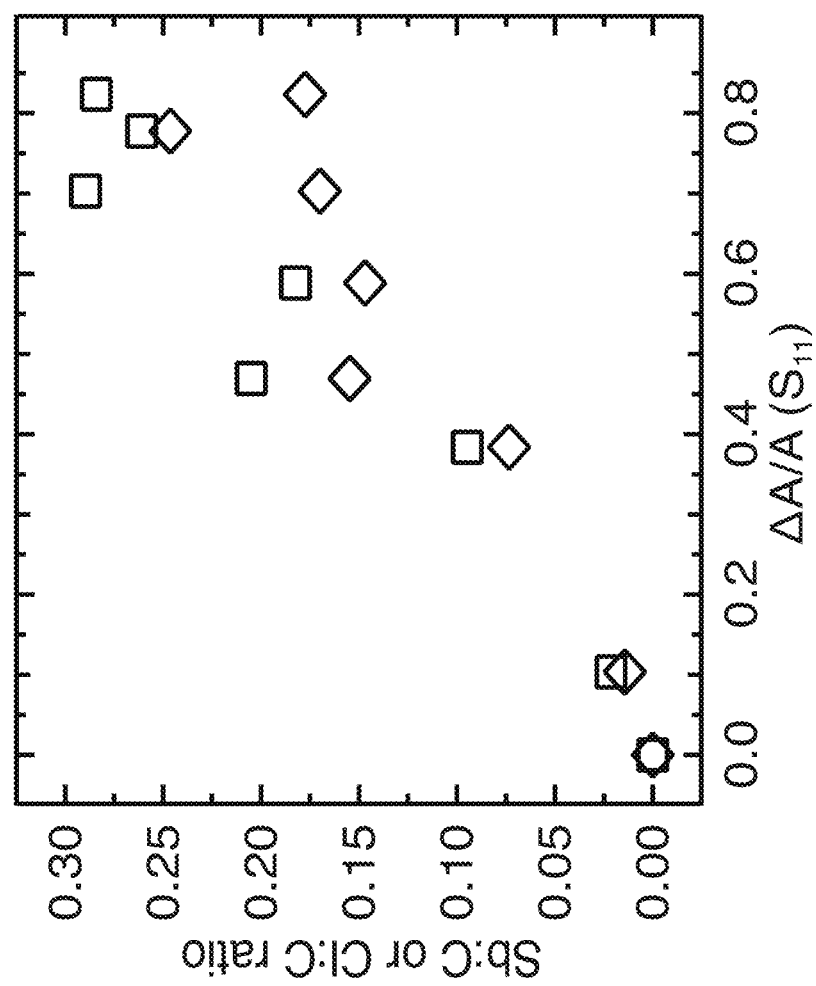
Figure 9G:
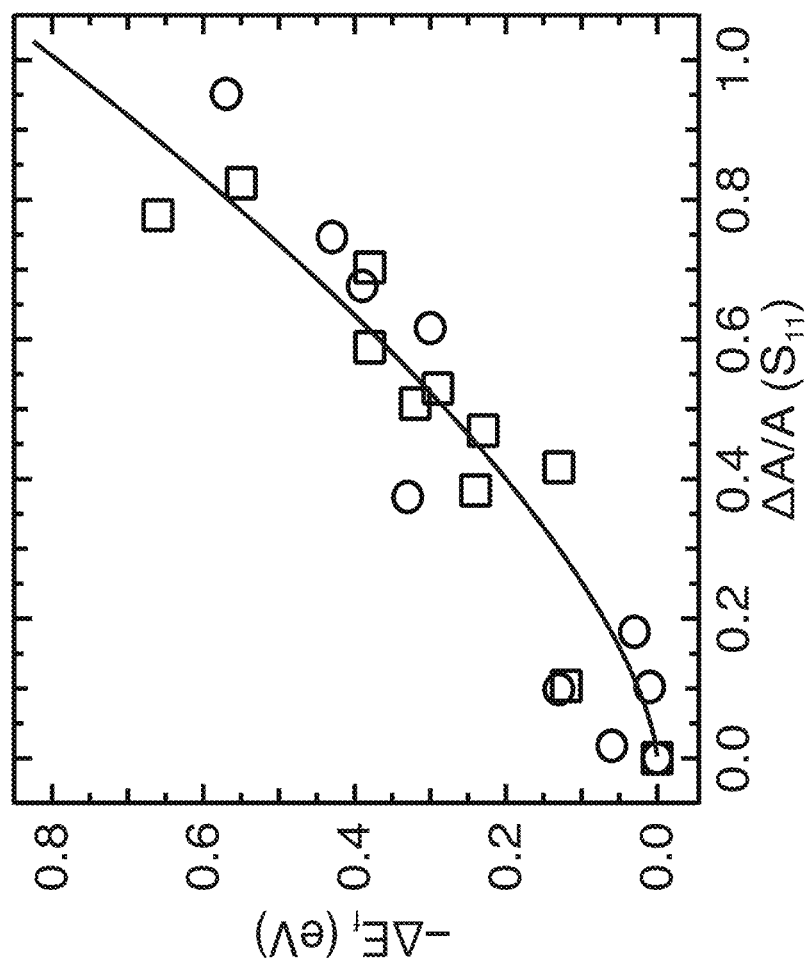

As shown in FIGS. 9(c)-9(g), x-ray photoelectron spectroscopy measurements of the systematically doped s-SWCNT networks were used to track the chemical changes associated with p-type OA doping. FIG. 9(c) shows XPS at the antimony (Sb) and chlorine (Cl) regions of an undoped (intrinsic, solid lines) and heavily p-type doped (dashed lines) PFO:SG65 (7,5) s-SWCNT networks. The inset of FIG. 9(c) shows the chemical structure of the OA dopant. FIG. 9(d) shows XPS at the carbon 1s (C1s) region for the same PFO:SG65 (7,5) s-SWCNT networks shown in FIG. 9(c). FIG. 9(e) shows the $E_{C1s}$ peak position for the same PFO:SG65 (7,5) s-SWCNT networks shown in FIG. 9(c). FIG. 9(f) shows Sb:C and Cl:C ratios measured by x-ray photoelectron spectroscopy as a function of the normalized bleach of the polymer:(7,5) s-SWCNT S$_{11}$ absorption transition. FIG. 9(g) shows the relationship between the Fermi level shift ($\Delta E_f$) and the normalized bleach of the S$_{11}$ absorption transitions for PFO:SG65 (7,5) s-SWCNT (circles) and neat LV SWCNT (squares) networks as a function of p-type doping with OA. The solid line in FIG. 9(g) is an empirical power law function used to determine the Fermi-level shift from the normalized bleach of the S$_{11}$ absorption.

Surface-bound OA produces strong Sb and Cl signals, as shown in FIG. 9(c), and the amount of surface-bound Sb and Cl increases for a film of SWCNTs progressively doped with increasing amounts of OA, as shown in FIG. 9(e). In FIG. 9(f), the Sb:C and Cl:C ratios are compared to the bleach of the S$_{11}$ exciton absorption transition, calculated based on the fractional change in area ($\Delta A/A_0$) for the S$_{11}$ transition due to doping, for example, from the data shown in FIGS. 9(a) and 9(b). The direct correlation of Sb and Cl signals with $\Delta A/A_0$ confirms that the doping level and thus ultimately the Fermi level can be controlled sensitively by the amount of adsorbed OA dopant, as discussed in further detail below.

XPS measurements can also be used to track the chemical potential of charge carriers injected by the OA dopants. FIG. 9(e) demonstrates an approximately 0.6 eV shift of the C 1s spectrum to lower energy for the heavily OA-doped (7,5) film. A control experiment measuring the C 1s spectrum of undoped and heavily doped PFO, as shown in FIGS. 8(a) and 8(b), indicates that the polymer core levels are also shifted by approximately 0.6 eV, although the signal within the PFO/SWCNT film is dominated by the s-SWCNTs. Since core electron energies in the XPS measurement are referenced to the Fermi level, this large red shift in C1s energy ($E_{C1s}$) results directly from a shift of $E_F$ ($\Delta E_F$) towards the valence band (p-type doping). FIGS. 9(e) and 9(f) demonstrate that $E_{C1s}$ is inversely correlated with the Sb:C and Cl:C ratios, showing that $E_F$ is controlled entirely by the amount of adsorbed OA.

Correlation of XPS and absorbance data for a series of controllably doped films allows calibration of the Fermi level shift ($\Delta E_F$) as a function of the relative bleach of the S$_{11}$ absorption transition. Here, $\Delta E_F$ is calculated according to the shift in $E_{C1s}$ between the undoped and doped s-SWCNT networks, i.e., $\Delta E_F = E_{C1s,undoped} - E_{C1s,doped}$, and $\Delta A/A_0$ (S$_{11}$) is calculated as described above. The data in FIG. 9(g) are best fit by a power law, which qualitatively matches the dependence obtained by integrating the DOS with respect to energy. FIG. 10 shows the integrated DOS for a semiconducting carbon nanotube. The integration (long-dashed line with open circles) of the DOS (short-dashed line with open squares) for the (10,8) s-SWCNT is in between the first and second van Hove singularities. The solid line shows a power law fit. The power law fit shown in FIG. 9(g) and FIG. 10 allows for calibration of changes in thermopower α, electrical conductivity σ, and TE power factor α$^2$σ with changes in Fermi energy through the easily measured bleach of the S$_{11}$ transition for a series of films doped with fine-tuned carrier densities via OA adsorption.

Figure 11:
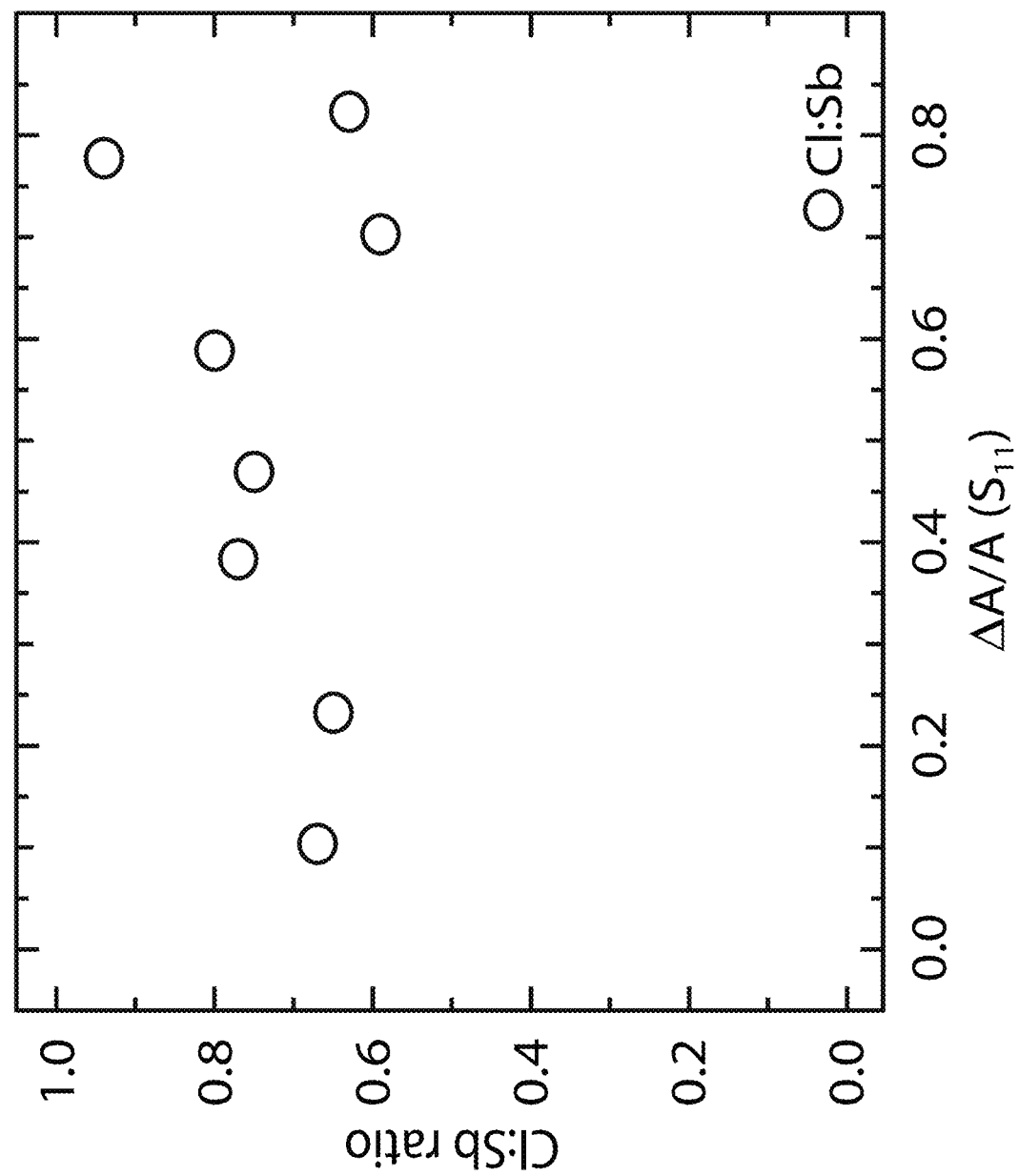
FIG. 11 shows the ratio of chlorine to antimony in doped PFO:SG65 (7,5) s-SWCNT networks.

FIG. 11 shows the ratio of chlorine to antimony (Cl:Sb) in doped PFO:SG65 (7,5) s-SWCNT networks. The Cl:Sb ratio was measured by x-ray photoelectron spectroscopy as a function of the normalized bleach of the polymer:(7,5) s-SWCNT S$_{11}$ absorption transition. As shown in FIG. 9(e), the antimony:carbon (Sb:C) and chlorine:carbon (Cl:C) ratios both exhibit the same dependence on the relative bleach of the S$_{11}$ absorption band, $\Delta A/A_0$(S$_{11}$), i.e., the extent of doping. However, FIG. 11 shows that the Cl:Sb ratio is always significantly lower than that expected for the [SbCl$_6$]$^-$ anion, and is typically in the range of approximately 0.6-0.95. This contrasts with the supposition of initial studies on OA doping of SWCNTs that suggested the formation of a charge-transfer complex between the oxidized SWCNT and the intact hexachloroantimonate [SbCl$_6$]$^-$ anion. This suggests that the [SbCl$_6$]$^-$ anion undergoes a significant amount of decomposition as a result of interacting with the SWCNT sidewall in the doping process.

Figure 12A:
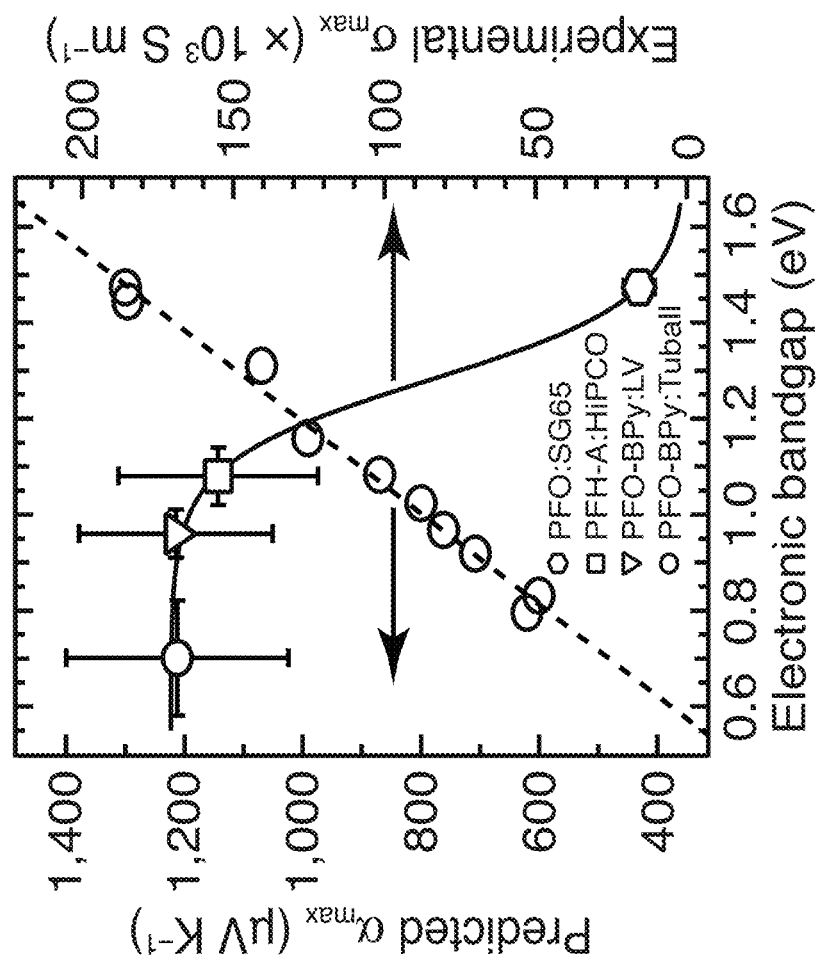

FIGS. 12(a)-12(f) show TE properties of various polyfluorene/s-SWCNT thin films prepared according to exemplary embodiments of the invention. FIG. 12(a) shows the dependence of the theoretically predicted peak thermopower α (dashed line) and maximum experimentally measured electrical conductivity σ (solid line) on the s-SWCNT electronic bandgap. The vertical error bars are derived from the standard deviation of the measured sheet resistances and film thicknesses. The horizontal error bars denote the standard deviation of the electronic band gap derived from the s-SWCNT diameter distribution. FIG. 12(b) shows a comparison of the predicted (line) and experimentally measured (symbols) maximum TE power factor $\alpha^2\sigma$ as a function of the s-SWCNT electronic bandgap. The vertical error bars are derived from the standard deviation of the measured sheet resistances, thermopowers, and film thicknesses. The horizontal error bars denote the standard deviation of the electronic band gap derived from the s-SWCNT diameter distribution.

Figure 12D:
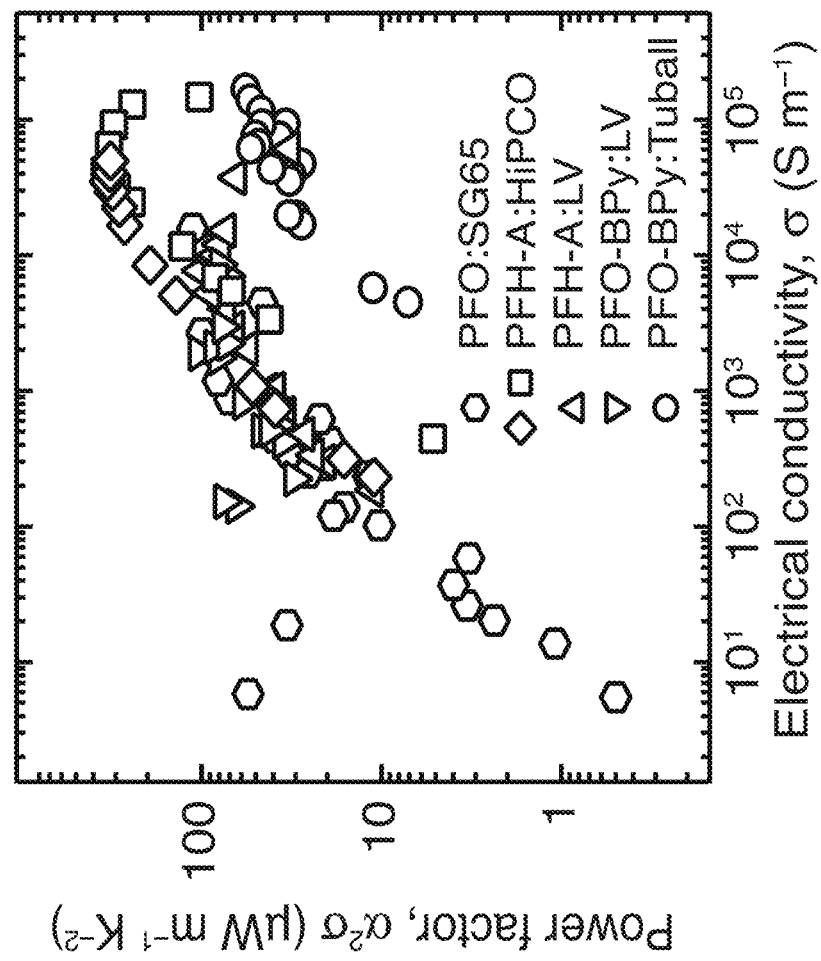

FIG. 12(c) shows the thermopower $\alpha$ as a function of the electrical conductivity $\sigma$ for PFO:SG65 (7,5) (hexagons), PFH-A:HiPCO (squares and diamonds), PFH-A:LV (upright triangles), PFO-BPy:LV (inverted triangles), and PFO-BPy:Tuball (circles). FIG. 12(d) shows the TE power factor $\alpha^2\sigma$ as a function of electrical conductivity $\sigma$ for PFO: SG65 (7,5) (hexagons), PFH-A:HiPCO (squares and diamonds), PFH-A:LV (upright triangles), PFO-BPy:LV (inverted triangles), and PFO-BPy:Tuball (circles). The legend in FIG. 12(c) also identifies the polymer:s-SWCNT networks in FIG. 12(d).

FIG. 12(e) shows a comparison of theoretical (line) and experimental (symbols) dependence of the thermopower $\alpha$ on the position of the Fermi energy for LV s-SWCNTs. The theoretically predicted electronic DOS is shown for reference.

Figure 12F:
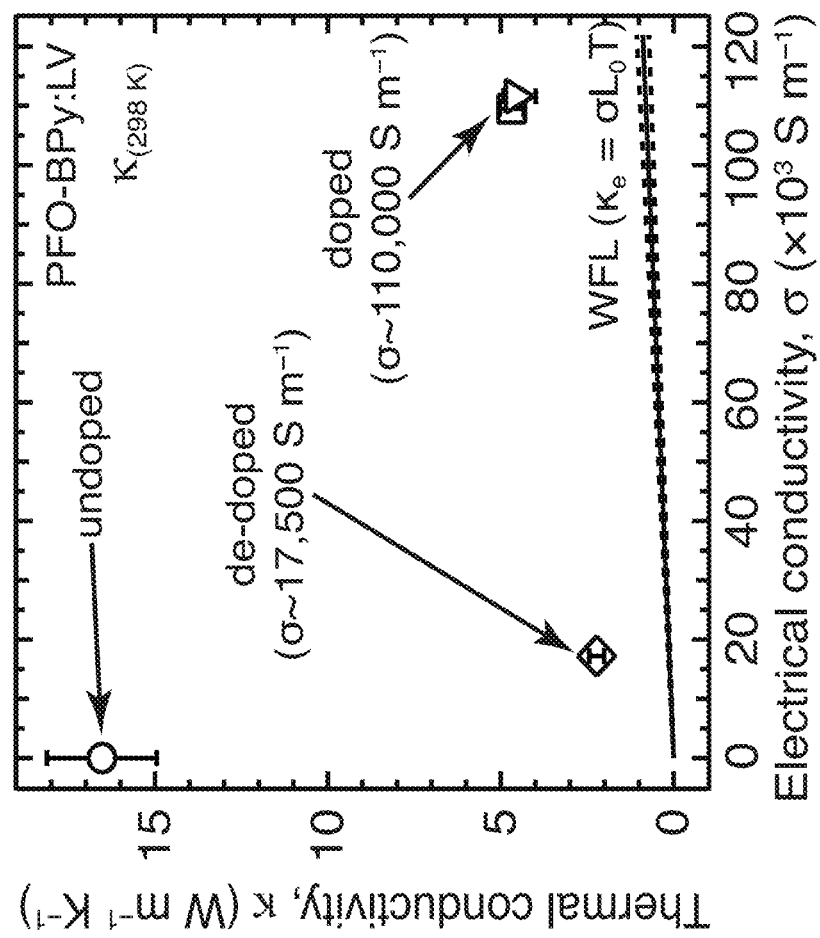

FIG. 12(f) shows the thermal conductivity $\kappa$ of an PFO-BPy:LV thin film as a function of the electrical conductivity $\sigma$ near 300 K. In this example, the doped sample was measured two separate times to demonstrate reproducibility and subsequently re-measured after de-doping under vacuum. The error bars, which in the case of the doped film are typically smaller than the symbol, arise nearly entirely from the error in the thickness determined by AFM. An estimation of the maximum electronic contribution to the thermal conductivity $\kappa$ using the empirical Wiedemann-Franz law, with the Sommerfeld value for the Lorenz number, $L_0$, is given by the solid line.

As an initial guide for TE power factor studies, FIG. 12(a) plots the band gap dependence for both the experimentally measured maximum electrical conductivity $\sigma$ (i.e. heavily doped) and the maximum calculated thermopower $\alpha$ (i.e. low doping). The electronic bandgap ($E_{g,elec}$) utilized in FIG. 12(a) is the sum of the optical bandgap ($E_{g,opt}$) and the exciton binding energy ($E_{b,\varepsilon}$), where $E_{b,\varepsilon}$ is calculated according to Capaz, R. B., Spataru, C. D., Ismail-Beigi, S. & Louie, S. G. Excitons in carbon nanotubes: Diameter and chirality trends. *Physica Status Solidi (b)* 244, 4016-4020 (2007), the entire disclosure of which is incorporated by reference herein, assuming a surrounding dielectric constant of $\varepsilon=4$.

In this example, the electronic band gap ($E_{g,elec}$) was determined by the addition of the optical band gap ($E_{g,opt}$) and the exciton binding energy ($E_b$), assuming a dielectric constant $\varepsilon=4$: i.e., $E_{g,elec}=E_{g,opt}+E_b$, $\varepsilon=4$. The binding energies of the $S_{11}$ excitons are described by the analytical function:

$$E_b = \frac{1}{d}\left(A + \frac{B}{d} + C\xi + D\xi^2\right) \quad (6)$$

where d is the SWCNT diameter in nm and $\xi=(-1)^\nu \cdot \cos(3\theta/d)$, where $\nu=(n-m) \mod 3$. Accordingly, for SWCNTs in vacuum ($\varepsilon=1.846$), A=0.6724 eV nm, B=-4.910×10$^{-2}$ eV nm$^2$, C=4.577×10$^{-2}$ eV nm$^2$, and D=-8.325×10$^{-3}$ eV nm$^3$. To re-calculate the binding energy for SWCNTs in a medium with a given dielectric constant, the scaling law ($E_b \propto \varepsilon^{-1.4}$) applies. For the calculations above, the diameter of each SWCNT is taken from Weisman, R. & Bachilo, S. Dependence of optical transition energies on structure for single-walled carbon nanotubes in aqueous suspension: An empirical Kataura plot. *Nano Lett.* 3, 1235-1238 (2003), the entire disclosure of which is incorporated by reference herein, and the optical gap may be taken either from the same document or from photoluminescence excitation maps on SWCNT dispersions.

Table 1 below shows the calculated binding energies ($E_b$) and Optical/Electronic Band Gaps ($E_g$) for various SWCNTs considered, either experimentally or theoretically.

TABLE 1

| SWCNT | d (nm) | $E_{b,\varepsilon=1.846}$ (eV) | $E_{b,\varepsilon=4}$ (eV) | $E_{g,opt}$ (eV) | $E_{g,elec}$ ($\varepsilon=4$) (eV) |
|---|---|---|---|---|---|
| (7, 5) | 0.829 | 0.78 | 0.26 | 1.21 | 1.47 |
| (10, 8) | 1.24 | 0.53 | 0.18 | 0.84 | 1.02 |
| (10, 0) | 0.794 | 0.70 | 0.24 | 1.07 | 1.31 |
| (11, 0) | 0.893 | 0.73 | 0.25 | 1.20 | 1.44 |
| (13, 0) | 1.032 | 0.55 | 0.19 | 0.90 | 1.08 |
| (14, 0) | 1.111 | 0.60 | 0.20 | 0.96 | 1.16 |
| (16, 0) | 1.27 | 0.46 | 0.15 | 0.76 | 0.92 |
| (17, 0) | 1.35 | 0.50 | 0.17 | 0.80 | 0.97 |
| (19, 0) | 1.508 | 0.39 | 0.13 | 0.66 | 0.80 |
| (20, 0) | 1.588 | 0.43 | 0.14 | 0.69 | 0.83 |
| (22, 0) | 1.747 | 0.34 | 0.11 | 0.59 | 0.70 |
| (7, 6) | 0.895 | 0.72 | 0.24 | 1.11 | 1.35 |
| (8, 6) | 0.986 | 0.63 | 0.21 | 1.06 | 1.27 |
| (8, 7) | 1.032 | 0.57 | 0.19 | 0.98 | 1.18 |
| (9, 7) | 1.103 | 0.58 | 0.20 | 0.94 | 1.14 |
| (11, 9) | 1.377 | 0.46 | 0.16 | 0.77 | 0.92 |

FIG. 12(a) demonstrates that the film electrical conductivity $\sigma$ decreases as a function of $E_{g,elec}$ (empirically fit with a sigmoid function). In contrast, the DFT-calculated thermopower $\alpha$ increases linearly with increasing $E_{g,elec}$. In FIG. 12(b), the expected band gap dependence of the TE power factor $\alpha^2\sigma$ is calculated, using the maximum $\alpha$ (calculated) and $\sigma$ (empirical) from FIG. 12(a). This empirically predictive estimation makes the assumption that the thermopower $\alpha$ at maximum TE power factor $\alpha^2\sigma$ (i.e. moderate doping) scales similarly for all s-SWCNTs as a function of electrical conductivity $\sigma$, an assumption that is tested by the careful control of the doping level, as discussed in further detail below. FIG. 12(b) suggests a distinct bandgap diameter (d) dependence for the TE power factor $\alpha^2\sigma$ of s-SWCNT films, with a maximum TE power factor $\alpha^2\sigma$ occurring for $\langle E_{g,elec}\rangle$ of approximately 1.1-1.2 eV ($\langle d \rangle$ of approximately 1-1.1 nm).

FIG. 12(c) displays the measured thermopower $\alpha$ as a function of the electrical conductivity $\sigma$ for five representative PF-wrapped s-SWCNT samples. As shown in FIG. 12(c), the thermopower $\alpha$ decreases with increasing electrical conductivity $\sigma$. However, the thermopower $\alpha$ at low doping is extraordinarily high. All samples, except for the PFO-BPy:Tuball networks, achieve a thermopower $\alpha$ of at least 200 µV K$^{-1}$ at low doping, whereas several samples have values approaching or above 1,000 µV K$^{-1}$. Furthermore, the thermopower $\alpha$ decays rather slowly with increasing electrical conductivity $\sigma$, decreasing less than an order of magnitude over three to four decades of electrical conductivity $\sigma$, similar to the trends observed for semiconducting polymers such as polythiophenes. As a result, the TE power factor $\alpha^2\sigma$ steadily rises with increasing electrical conductivity $\sigma$, reaching values above 100 µW m$^{-1}$ K$^{-2}$ at electrical conductivity $\sigma$ values above approximately 10,000 S m$^{-1}$, as shown in FIG. 4(d). The TE power factor $\alpha^2\sigma$ of the HiPCO networks reaches a value of approximately 340 µW m$^{-1}$ K$^{-2}$, which is the highest TE power factor $\alpha^2\sigma$ (by a factor of approximately 3.4) ever reported for a SWCNT network. The TE power factor $\alpha^2\sigma$ observed for the HiPCO sample is comparable to the best values obtained for high-performance Poly(3,4-ethylenedioxythiophene) (PEDOT)-based polymer TE materials. The experimental trend for the maximum TE power factor $\alpha^2\sigma$ obtained for each representative diameter (band gap) distribution, as shown by the symbols in FIG. 12(b), matches the predicted trend shown by the line in FIG. 12(b) rather well.

The measured thermopower $\alpha$ shown in FIG. 12(c) are roughly in the range predicted by the first-principles calculations for s-SWCNTs, suggesting that the large $\alpha$ values are determined, at least in part, by the electronic structure of the s-SWCNTs. Recent studies have attributed somewhat large (but significantly lower than observed here) values of the thermopower $\alpha$ primarily to the contribution of tube-tube junctions. These studies assume a low to moderate value for the inherent thermopower $\alpha$ of isolated s-SWCNTs that is enhanced by the thermal resistance of tube-tube junctions within the film. The much higher (predicted and observed) values for $\alpha$ according to exemplary embodiments of the invention suggest that it may be important to consider the inherently large thermopower $\alpha$ imparted to s-SWCNTs as a result of their intrinsic electronic structure.

To explicitly compare the experimentally obtained thermopower $\alpha$ to the first-principles calculations, the calibration curve generated in FIG. 9(g) is utilized to convert $\Delta A/A_0$ for the progressively doped s-SWCNT films to $\Delta E_F$. FIG. 12(e) compares the empirical thermopower $\alpha$ of the two LV s-SWCNT networks to that predicted for the (10,8) s-SWCNT (a representative predominant species within the LV distribution), as a function of the Fermi level position. It is first interesting to note that the magnitude of $\alpha$ for the PFO-BPy sample at low doping is commensurate with that predicted by first-principles. Additionally, although the experimentally observed thermopower $\alpha$ decays with increasing Fermi level shift, the decay is much slower than theoretically predicted. In particular, the experimental trend does not decay to zero in the range of $-0.75$ V$\leq\Delta E_F\leq-0.45$ V, but is instead in the range of approximately 70-150 µV K$^{-1}$ in this range. The slow decay may result, at least in part, from the contribution of tube-tube junctions to the thermopower $\alpha$.

In order to evaluate the TE performance beyond the TE power factor $\alpha^2\sigma$, the in-plane thermal conductance of an LV s-SWCNT:polymer network deposited onto a micromachined silicon nitride (Si—N) platform was measured. These structures, formed from patterned 500 nm thick low-stress Si—N, consisted of two islands connected by an approximately 90 micron wide, approximately 2 mm long Si—N beam that forms the sample growth stage. Note the lateral dimension (over which the temperature gradient is established) is enormous compared to the sample film thickness, ensuring the experiment is sensitive only to in-plane heat flow. Each island contains a heater, a thermistor, and electrical leads formed from patterned Cr/Pt (thickness 10 nm/40 nm). This allows accurate control and measurement of thermal gradients on the thin films.

Figure 13A:
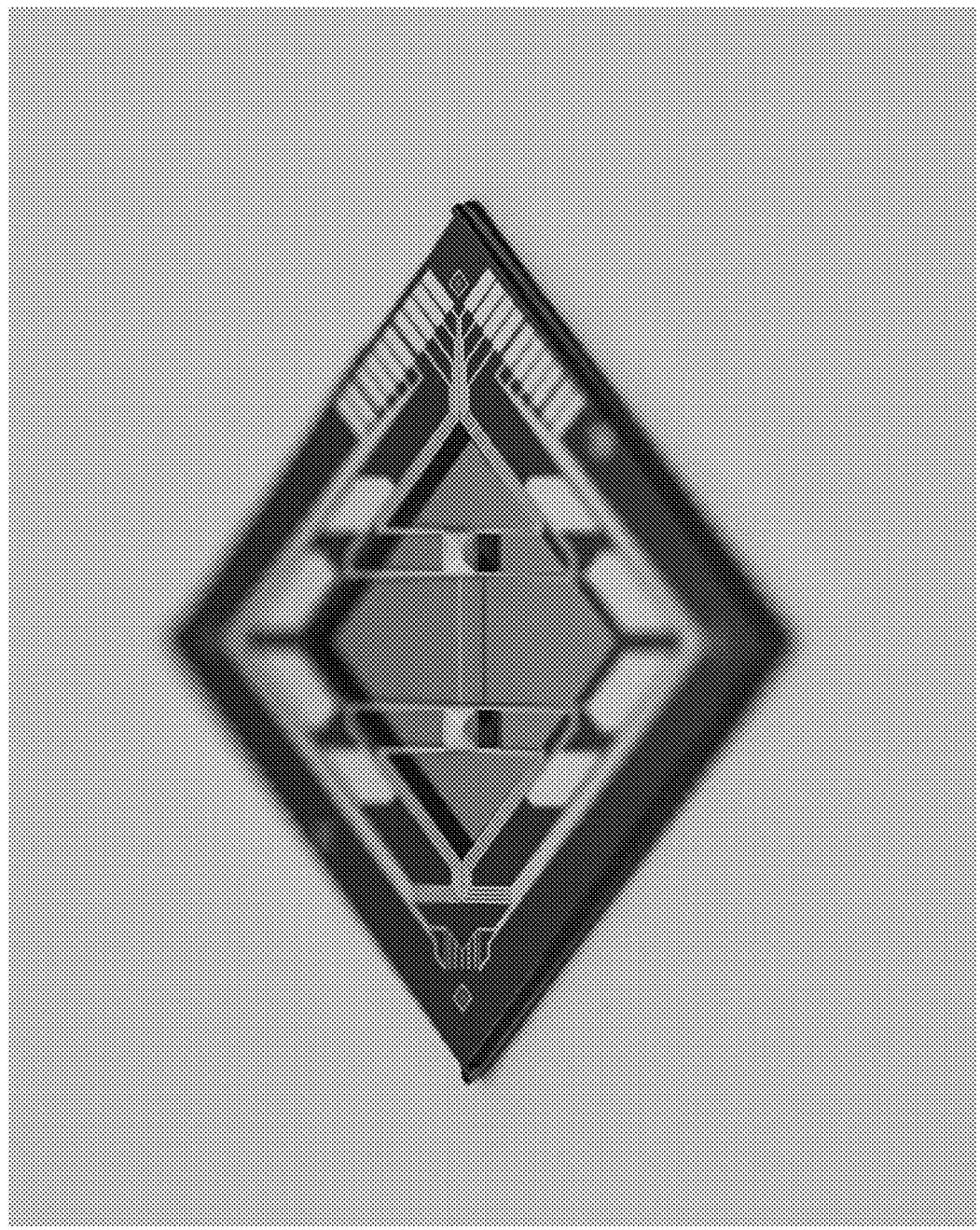
FIGS. 13(a)-13(d) show a micromachined suspended silicon-nitride (Si—N) thermal isolation platform.
Figure 13B:
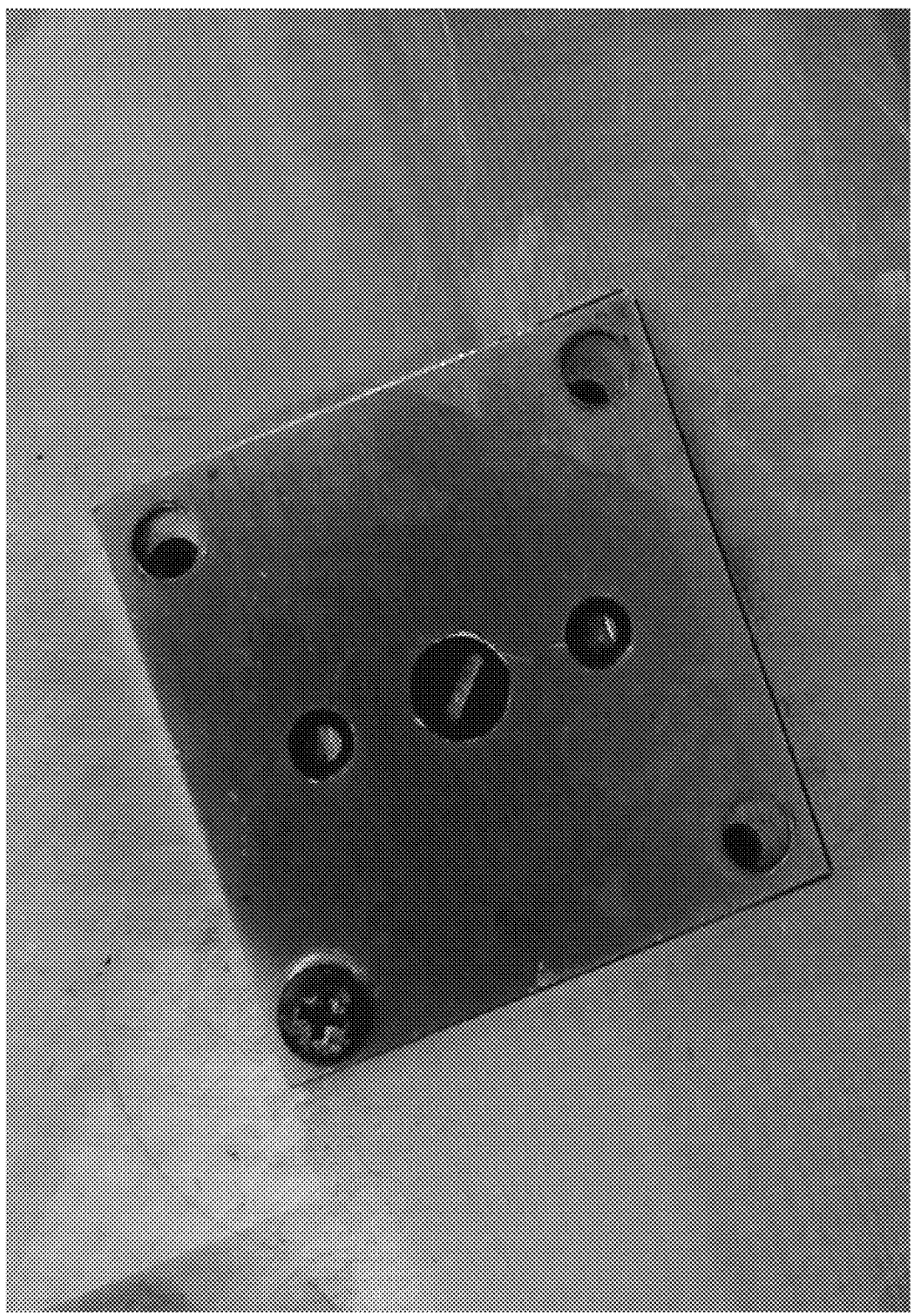
Figure 13C:
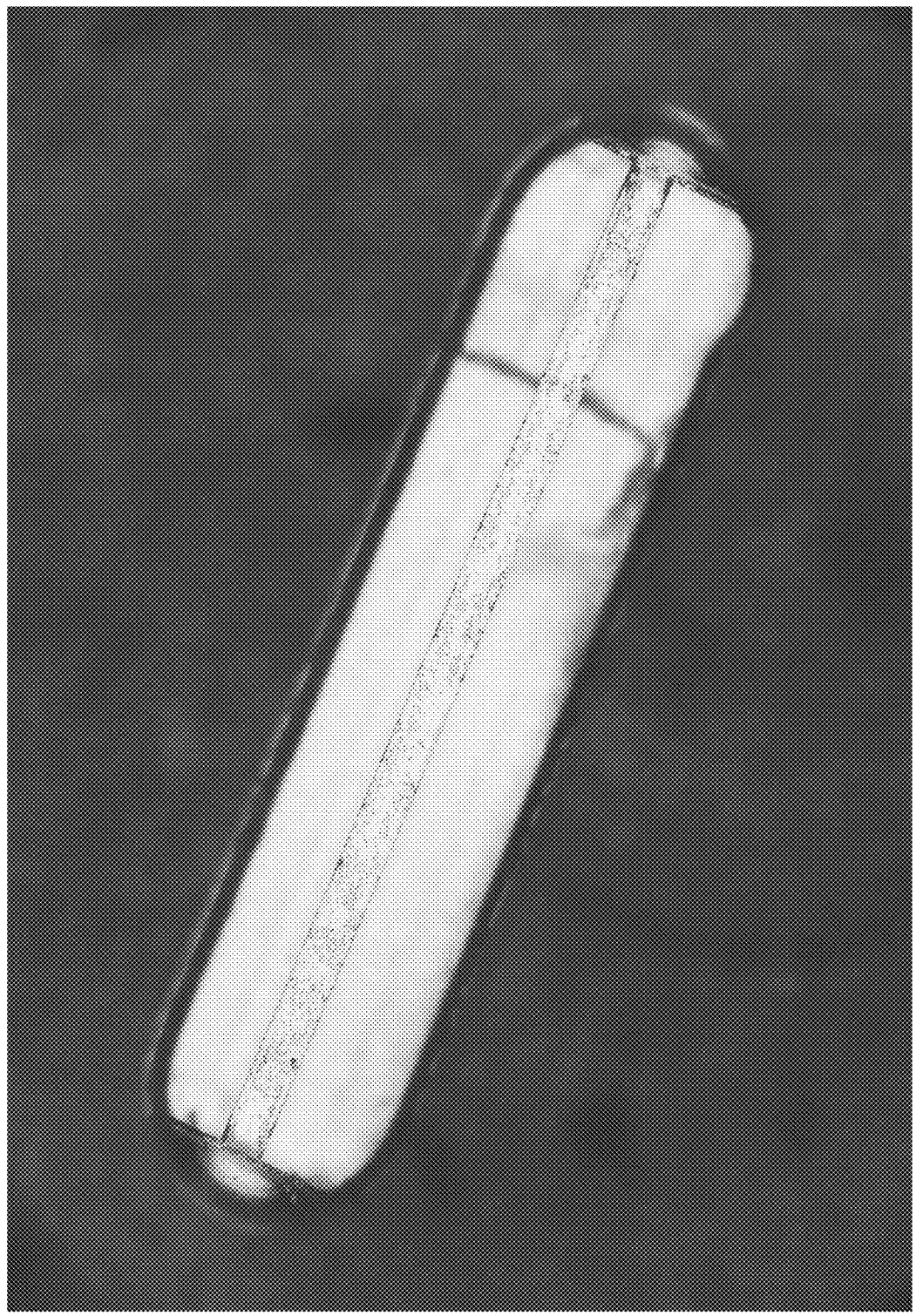
Figure 13D:
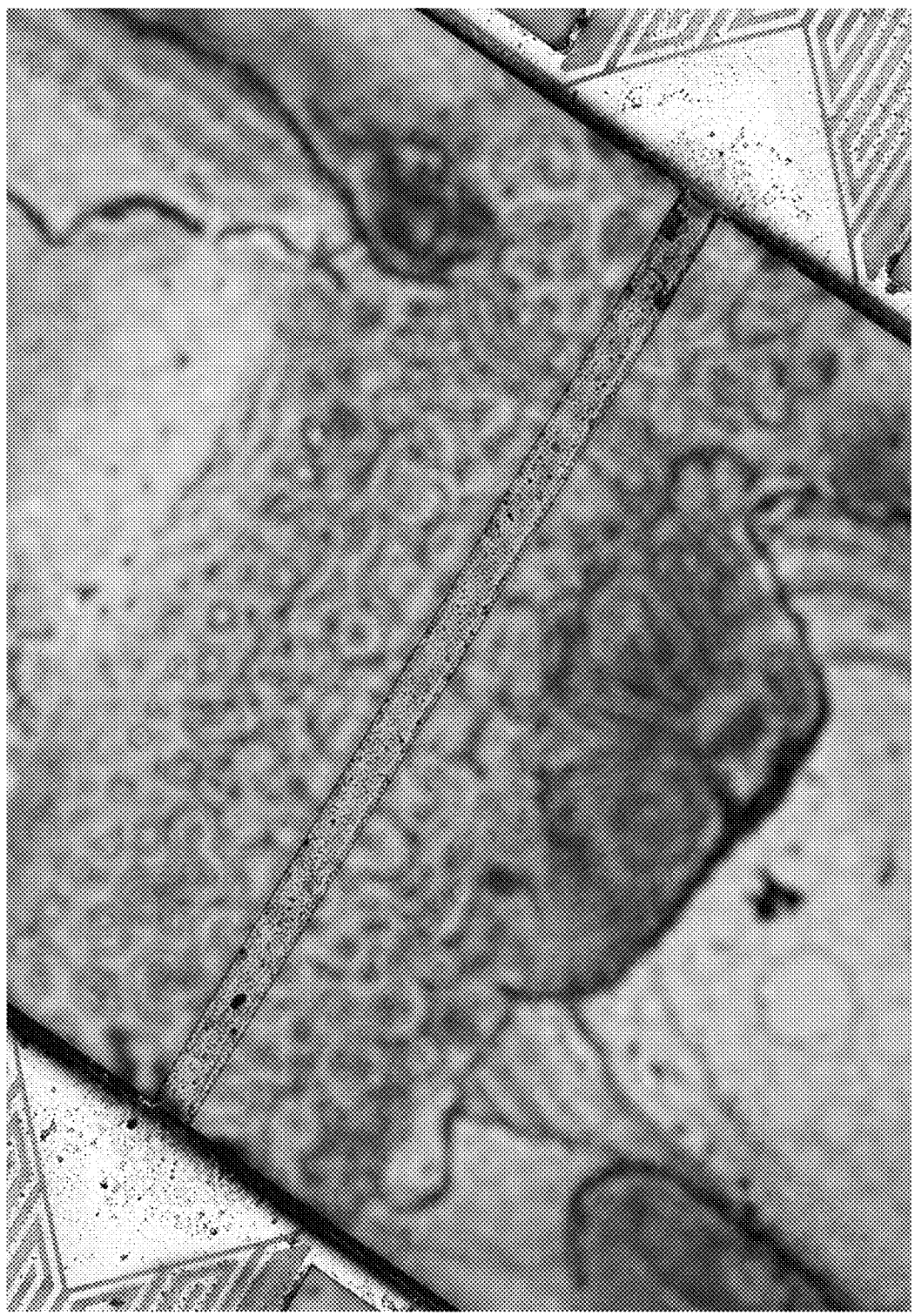
Figure 14D:
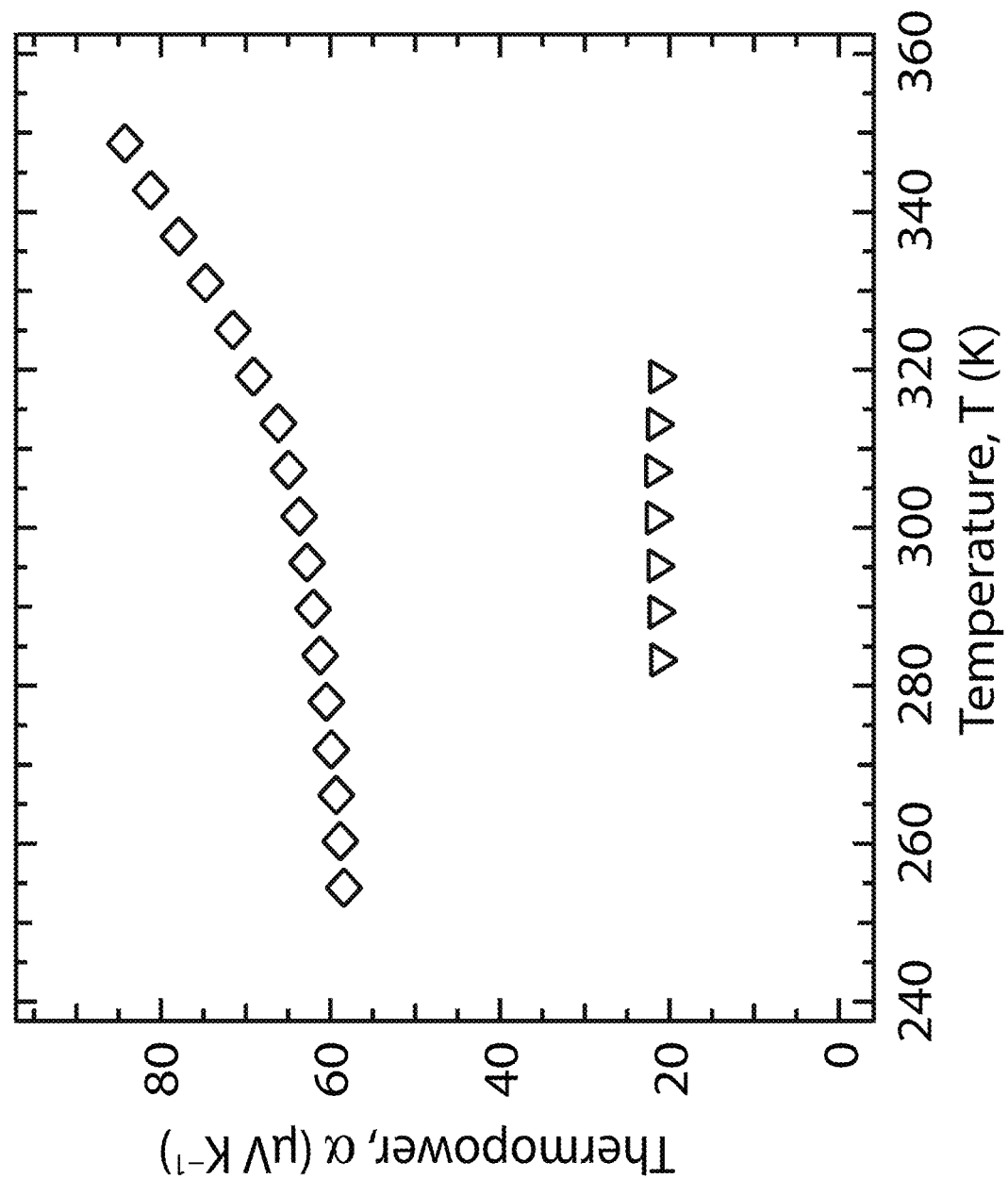

In one example, a micromachined suspended Si—N thermal isolation platform measurement technique shown in FIGS. 13(a)-13(d) was employed to measure the raw thermal conductance data shown in FIG. 14(a), which was subsequently used to calculate the thermal conductivity $\kappa$ data presented in FIG. 14(b) and FIG. 12(f). FIG. 13(a) shows an optical image of the Si—N platform. FIG. 13(b) shows an optical image of the shadow mask used to spray deposit the s-SWCNT network onto the Si—N beam between the islands on the platform. FIG. 13(c) shows an optical image of the Si—N beam, viewed through the shadow mask shown in FIG. 13(b). FIG. 13(d) shows an optical image of the s-SWCNT network after ultrasonic spray deposition through the shadow mask, showing that the network extends over the entire length of the Si—N beam and onto the triangular electrical leads on the two islands. This data measured the combined thermal conductance of the Si—N beam and s-SWCNT network, which was then corrected for the contribution of the bare Si—N beam and converted to thermal conductivity $\kappa$ using the dimensions of the deposited s-SWCNT network. The data shown in FIGS. 14(a)-14(d) indicate that the thermal conductance of the undoped PFO-BPy:LV s-SWCNT network (circles) is actually decreased upon doping (diamonds, squares, and inverted triangles).

Before sample deposition, a protective 10 nm layer of amorphous $Al_2O_3$ was deposited on the platforms through a shadow mask that leaves the sample electrical leads exposed. The platform was then exposed to OA under the same conditions as occur in the doping step. This step can leave dopant molecules attached to the Si—N, and can cause small (approximately 10 nW K$^{-1}$) reductions in the background Si—N thermal conductance due to phonon scattering. The background thermal conductance of the platform was then measured by recording the island temperatures as a function of applied power and employing a simple 2-body thermal model. After this measurement, the film was ultrasonically sprayed through another shadow mask (see FIG. 13(b)), and the platform conductance measurement was repeated. The Si—N beam can be observed through the mask in FIG. 13(c), and with a SWCNT film deposited onto it and the triangular electrical leads in FIG. 13(d). The background conductance was subtracted from this second measurement to give the thermal conductance contribution of the film. This was converted to thermal conductivity $\kappa$ via the sample geometry, including the thickness determined by AFM. The platform was then immersed in OA and the conductance measurement performed again to test the sample in the doped state followed by deliberate de-doping to achieve a s-SWCNT network with an intermediate electrical conductivity $\sigma$ (see FIGS. 14(a)-14(d)).

FIGS. 14(a)-14(d) show the temperature-dependent TE properties of undoped and doped PFO-BPy:LV s-SWCNT networks. FIGS. 14(a)-14(d) show the thermal conductance, the thermal conductivity $\kappa$, the electrical conductivity $\sigma$, and the thermopower $\alpha$, respectively, as functions of temperature T. Background measurements were carried out between 250 and 325 K for the suspended Si—N sample platform before film deposition (dashed line). Initial measurements were carried out between 285 and 315 K after deposition of the PFO-BPy:LV s-SWCNT network (circles), and after doping (two subsequent measurements, squares and inverted triangles, separated by a waiting period in vacuum that slightly de-doped the film). After an extended de-doping period the sample was re-measured over an extended temperature range of 250 to 350 K (diamonds).

The undoped network adds a large contribution to the total thermal conductance relative to the conductance of the bare Si—N beam. FIG. 12(f) shows the extracted thermal conductivity $\kappa$ data near room temperature for a PFO-BPy:LV network that is either undoped or doped. The OA dopant, while clearly adding holes to produce a large electrical conductivity σ of approximately 110,000 S m$^{-1}$, causes a significant drop in the total thermal conductance relative to the undoped network. Before doping, κ is fairly large at approximately 16.5 W m$^{-1}$ K$^{-1}$, as shown in FIG. 12(f), though certainly still a small fraction of the very large κ seen in isolated SWCNTs. Since this s-SWCNT film is intrinsic (with immeasurable electrical conductivity σ), the thermal conductivity κ is entirely due to phonons. After doping, the much lower κ (approximately 4.5 W m$^{-1}$ K$^{-1}$) is still significantly larger than the estimate of the electronic contribution from the Wiedemann-Franz law (shown as the solid black line). Furthermore, the doping dependence of κ appears to be complex, since κ decreases even further to approximately 2 W m$^{-1}$ K$^{-1}$ when the same film is intentionally de-doped to an electrical conductivity σ of approximately 17,000 S m$^{-}$.

The large drop in κ suggests that the addition of the dopant not only contributes holes to the SWCNT-polymer hybrid but also adds scattering centers for phonons. This intriguing result provides strong evidence that the thermal conductivity κ in s-SWCNT networks is dominated by phonons, with a very small electronic contribution, and can be significantly reduced by appropriate doping strategies, even at very high electrical conductivity σ (e.g. greater than 100,000 S m$^{-1}$). As discussed above, reducing the thermal conductivity κ may increase the figure of merit zT. Beyond doping strategies, network morphology and isotope composition may be controlled as rational routes towards further reducing the thermal conductivity κ (and increasing zT) by interfacial phonon scattering.

Figure 15A:
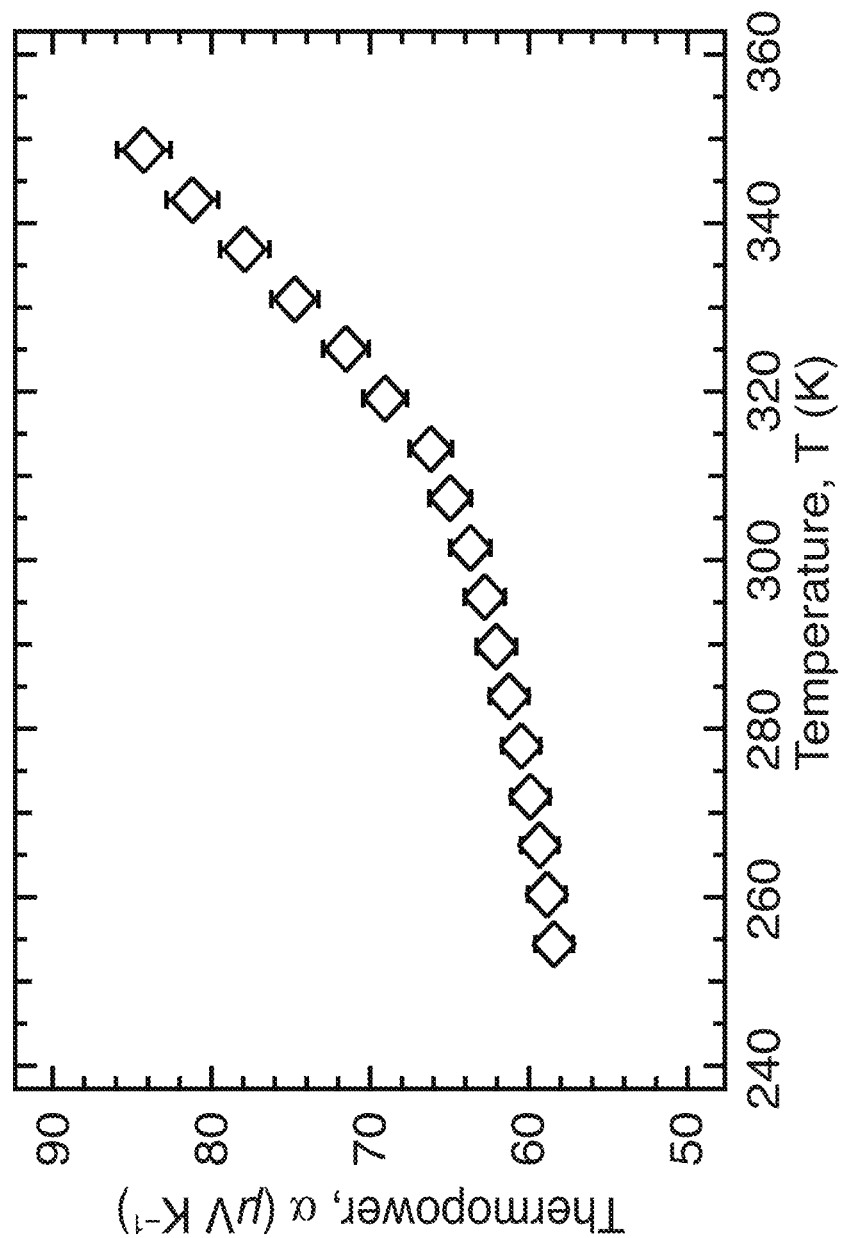
FIGS. 15(a)-15(c) show the temperature dependence of the TE properties of a moderately doped PFO-BPy:LV s-SWCNT network.
Figure 15B:
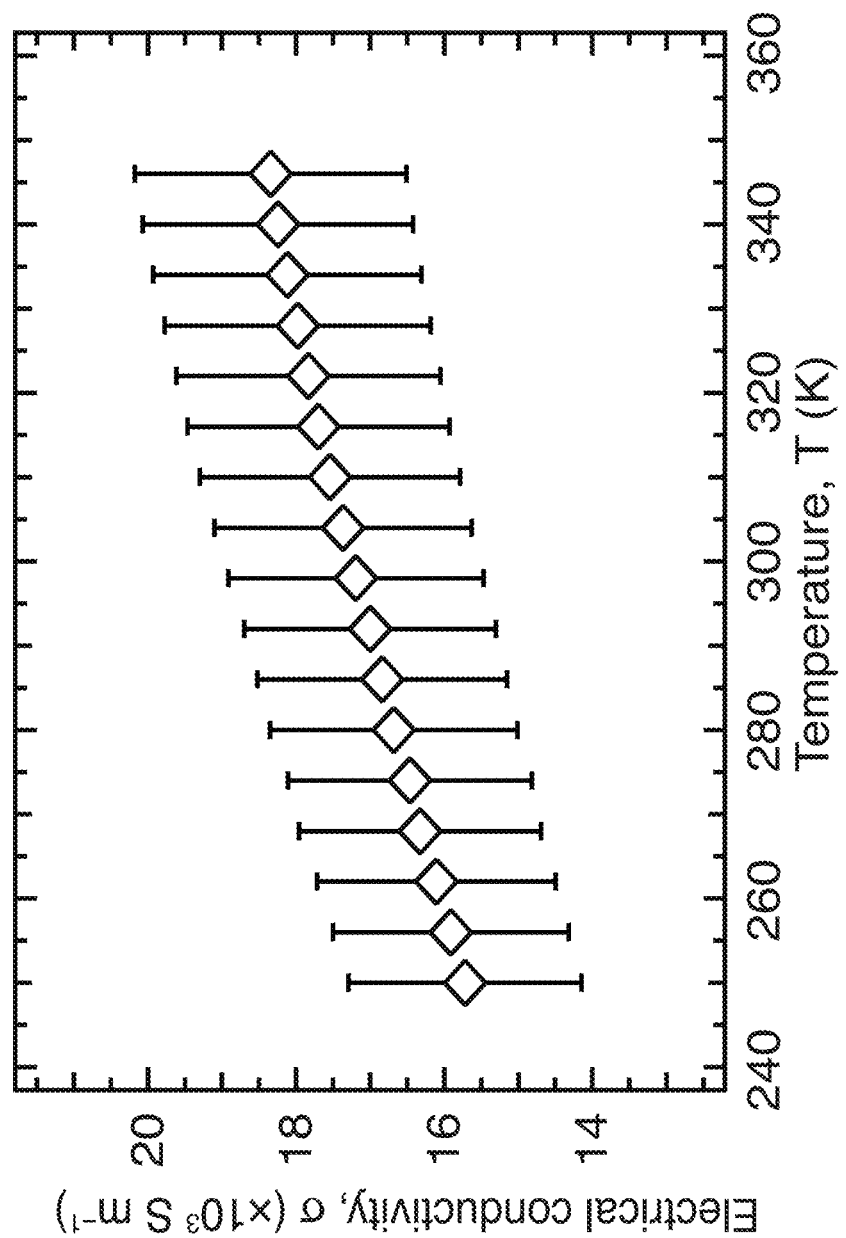
Figure 15C:
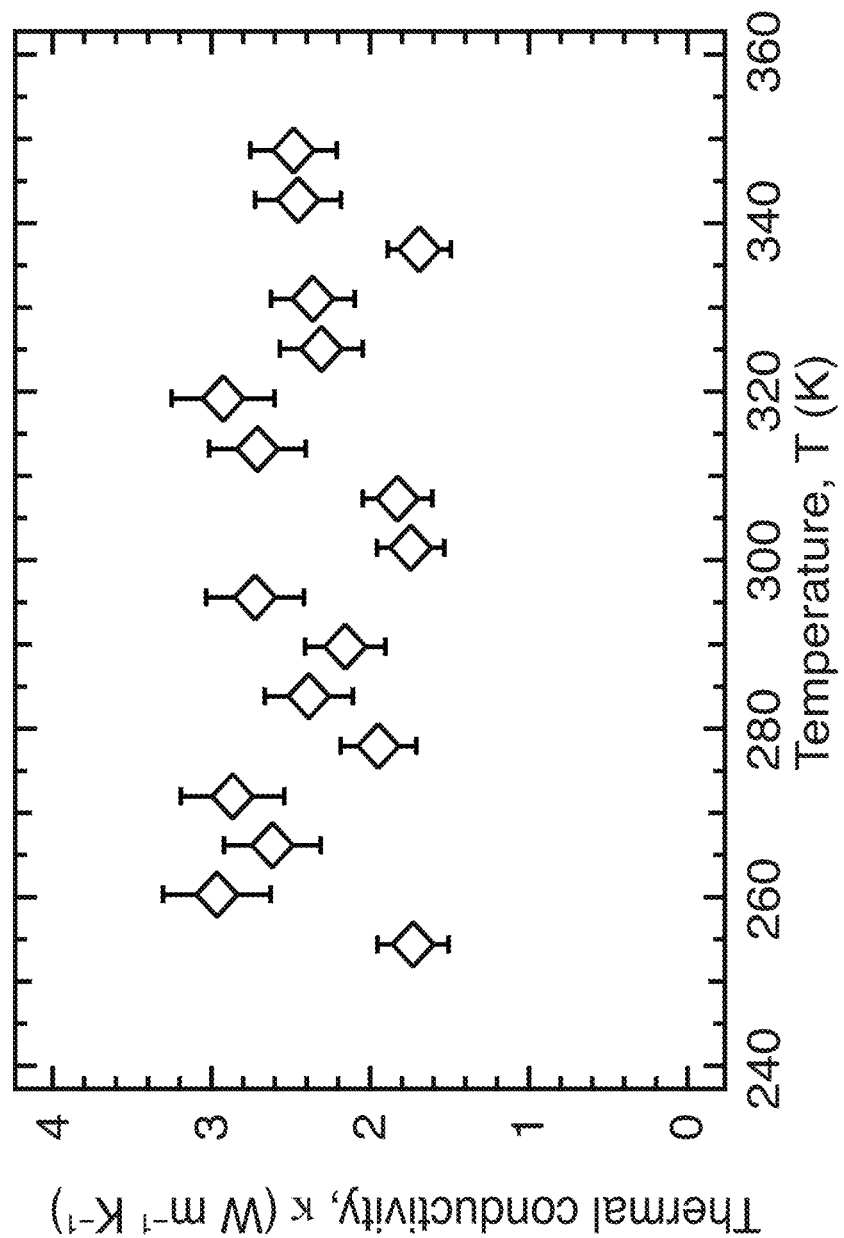

Although the zT values for neat s-SWCNT networks according to exemplary embodiments of the invention are still low (zT≈0.01-0.05), the weak correlation of both the thermopower α and the thermal conductivity κ to the electrical conductivity σ observed here provides a new framework for understanding the role of s-SWCNTs in TE applications. Additionally, zT may be further improved by optimizing the operational temperature T range, as illustrated by the temperature dependence of the TE properties shown in FIGS. 15(a)-15(c) (also see FIGS. 14(a)-14(d)). FIGS. 15(a)-15(c) show the temperature dependence of the thermopower α, electrical conductivity σ, and thermal conductivity κ, respectively, for an approximately 90 nm thick PFO-BPy:LV s-SWCNT network. These data show that while both the thermopower α and electrical conductivity σ increase with temperature T, the thermal conductivity κ stays fairly constant, resulting in an enhanced zT at elevated temperature T. The error bars for the thermopower α are determined from the uncertainties in the Seebeck voltage and applied temperature difference and are approximately 2% of the absolute thermopower α. The errors bars for the electrical conductivity σ and thermal conductivity κ take into account the uncertainty in the measured resistivity and thermal conductance, respectively, but are dominated by the approximately 10% uncertainty in the measured film thickness.

FIGS. 15(a)-15(c) indicate that zT increases as a function of temperature T, and the zT at 350 K is approximately a factor of 2.5 greater than that determined at 300 K. At 350 K, zT is still increasing, and the optimum temperature T may be above 350 K. SWCNTs are significantly more stable with respect to elevated temperatures than typical conducting polymers. Thermogravimetric analysis shows that SWCNTs (in the absence of metal catalyst nanoparticles) can withstand temperatures up to 500° C. in air, which is well above the temperatures most polymer systems can withstand. This enhanced stability, and the results in FIGS. 14(a)-14(d) suggest that s-SWCNTs may represent a novel organic TE component that is viable at elevated temperatures, either on their own or within composites.

Figure 16B:
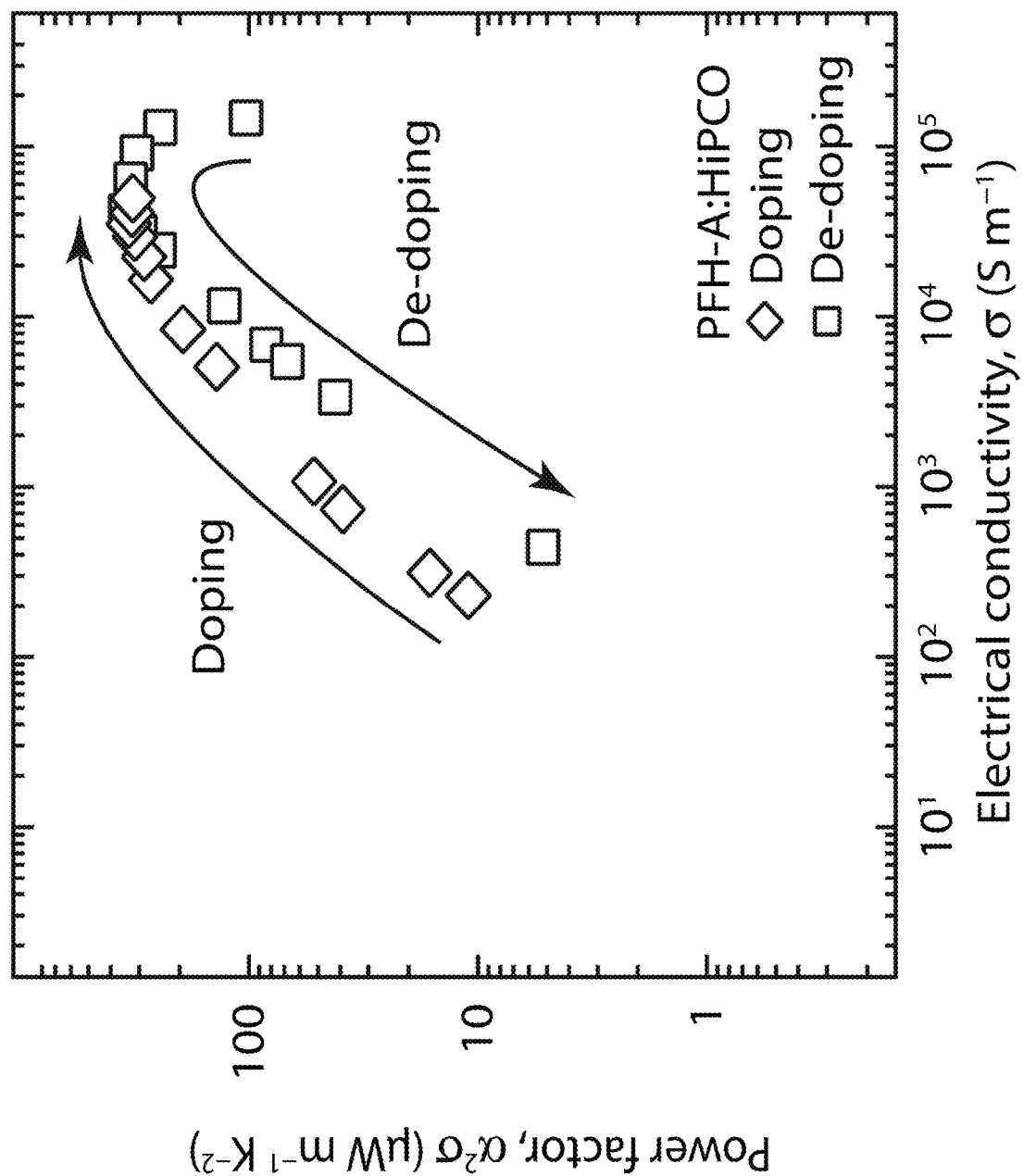

The thermopower α and TE power factor α$^2$σ as functions of the electrical conductivity σ do not always follow the same trends when a sample is doped sequentially or de-doped from its fully doped state. FIGS. 16(a) and 16(b) show this "hysteresis" for two PFH-A:HiPCO networks. FIGS. 16(a) and 16(b) show the impact of the doping protocol followed to tune the carrier density on the thermopower α and the TE power factor α$^2$σ, respectively. Interestingly, the peak TE power factor α$^2$σ that can be achieved appears to be independent of the doping protocol. Specifically, FIG. 16(b) shows that the peak TE power factor α$^2$σ is independent of the direction in which the carrier density is tuned. This has potential implications for the fabrication of TE generators composed of doped carbon nanotube networks, since it suggests that the path followed to reach the target doping density is unimportant in determining the optimal performance. Accordingly, as discussed above, the target doping density may be achieved either by adding the charge-carrier dopant to the s-SWCNT network until the target doping density is reached, or saturating the charge-carrier dopant in the s-SWCNT network and then de-doping the s-SWCNT network until the target doping density is reached.

The methods of preparing an s-SWCNT network discussed above result in a polymer being wrapped around the carbon nanotubes of the s-SWCNT network. However, the TE properties of the s-SWCNT network may be further improved by removing at least a portion of the wrapped polymer. For example, an H-bonded supramolecular polymer (SP) may be used to selectively disperse s-SWCNTs. After the s-SWCNTs are dispersed by the SP, the SP may be disassembled and removed by disrupting the H-bonds, allowing for the production of samples enriched with s-SWCNTs and containing no residual polymer. The SP may be dissolved after thin-film deposition. As discussed in further detail below, removal of the H-bonded supramolecular polymer after thin-film deposition results in (1) enhanced carrier doping and electrical conductivity σ, (2) enhanced charge carrier mobility, and (3) approximately a factor of 2 increase in the TE power factor α$^2$σ.

Three s-SWCNT network samples were prepared by LV. The first sample was "PFOBPy:LV", a control sample of LV s-SWCNTs dispersed by poly[(9,9-dioctylfluorenyl-2,7-diyl)-alt-co-(6,6'-{2,2'-bipyridine})] (PFO-BPy) in which a polymer is wrapped around the carbon nanotubes of the s-SWCNT network. The second sample was "Solid SPR," a sample of LV s-SWCNTs that were dispersed using the H-bonded SP, where the SP was removed by treatment with trifluoroacetic acid (TFA) after network deposition. The third sample was "Solution SPR", a sample of LV s-SWCNTs that were dispersed using the H-bonded SP, where the SP was removed by treatment with TFA in solution prior to network deposition.

Figure 17B:
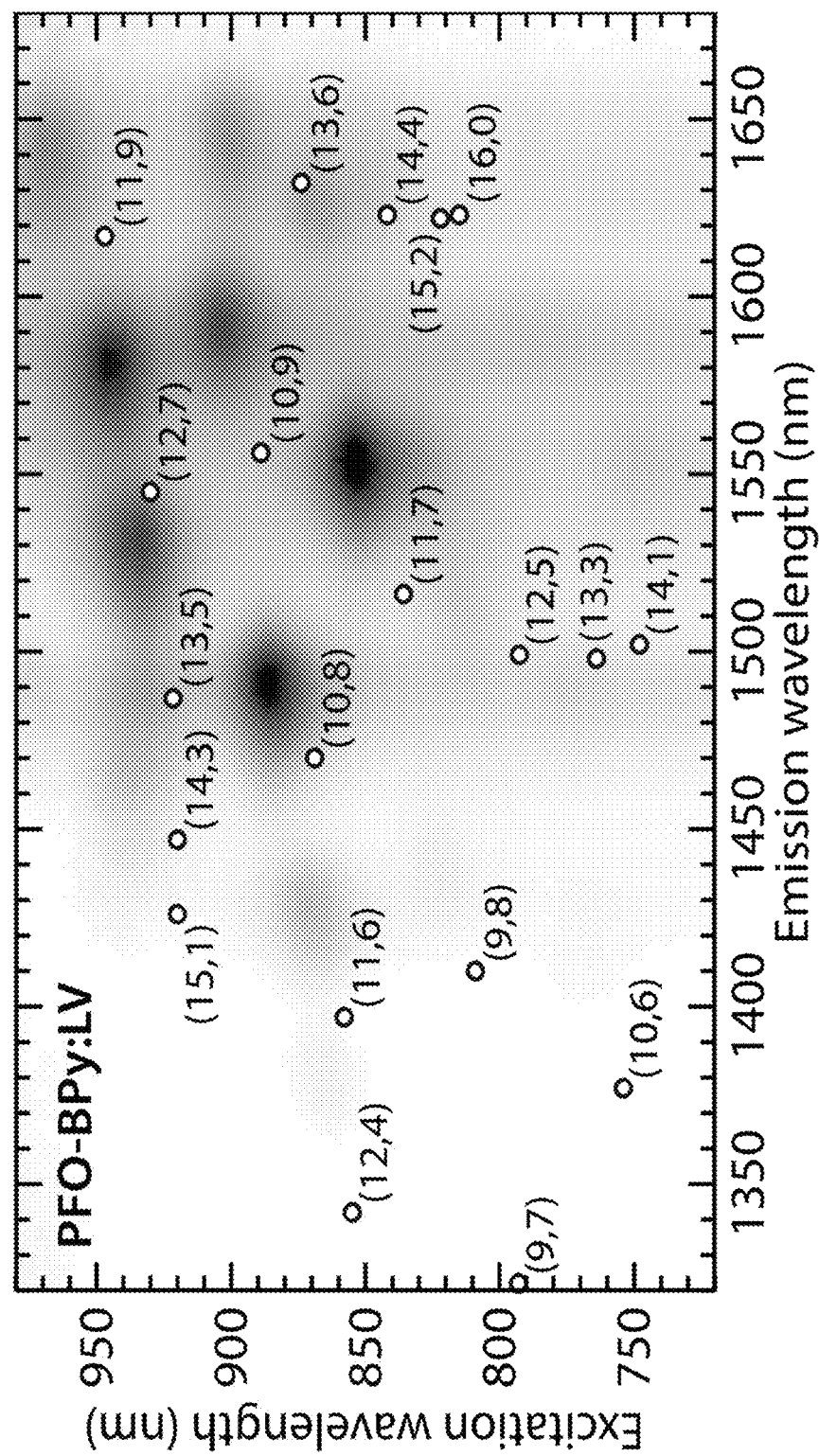
Figure 17C:
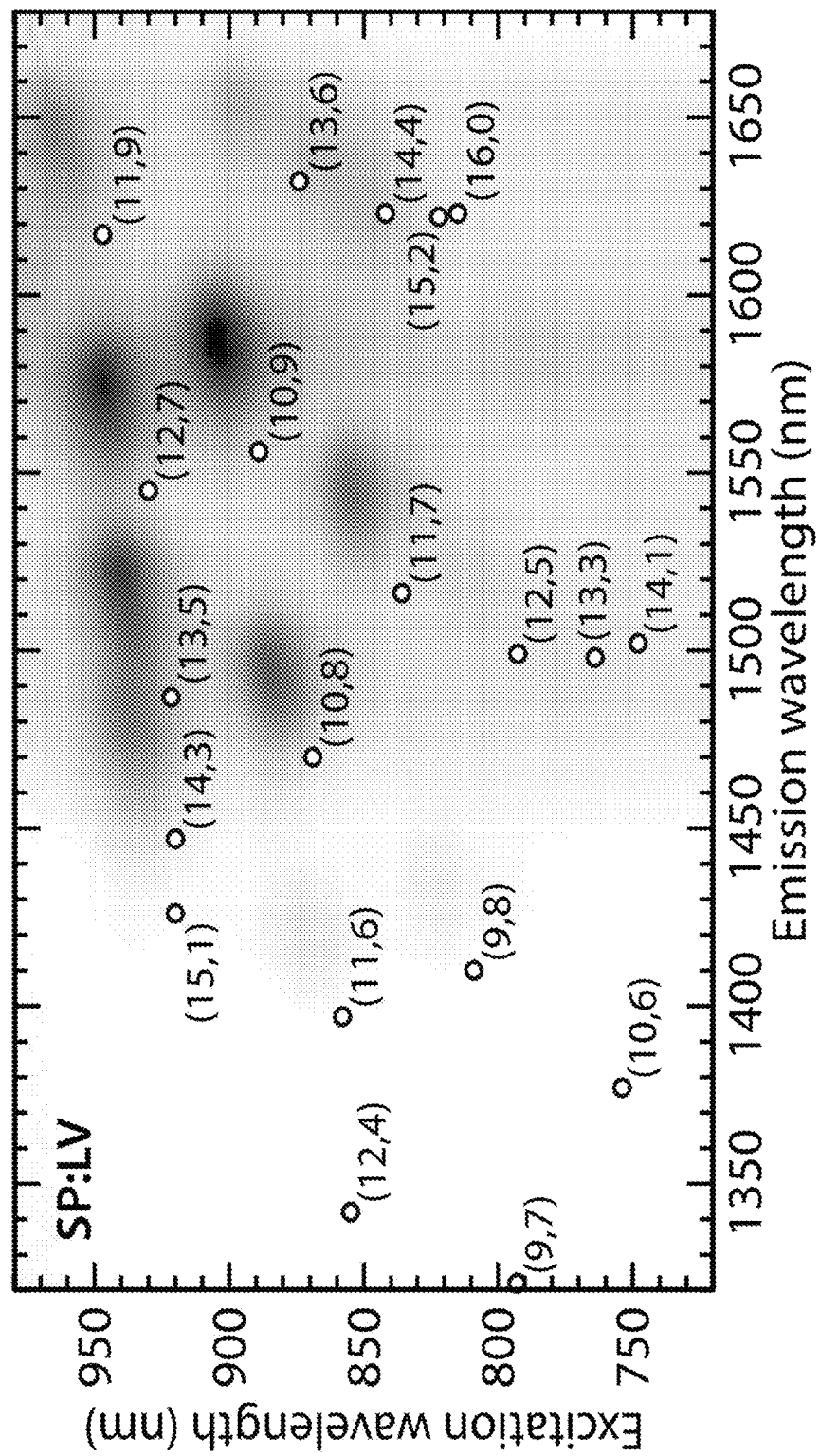

FIG. 17(a) shows the absorption spectra, normalized to the area under the second-exciton (S$_{22}$) optical transition envelope, for the three s-SWCNT inks used to prepare the s-SWCNT networks. The similarity between the peak envelopes corresponding to both the first-exciton (S$_{11}$) and S$_{22}$ optical transitions indicates that PFO-BPy and SP result in similar s-SWCNT distributions extracted from the starting LV material, with some subtle differences in the exact yield of the individual s-SWCNT species. In both cases, the lack of peaks in the 600-850 nm region, characteristic of the $M_{11}$ optical transitions, suggests that m-SWCNT contamination is below the optical detection limit (i.e., <1%). As shown in FIGS. 17(b) and 17(c), the similar species distributions are confirmed by photoluminescence excitation maps, which show emission peaks of broadly similar relative intensities, corresponding to s-SWCNTs with similar chiral indices, denoted by the (n,m) indices adjacent to the circles that identify particular emission peaks. For the sample where the H-bonded SP is removed in solution and the s-SWCNTs are subsequently re-dispersed in N-Methyl-2-pyrrolidone (NMP), there is significant broadening and a discernable bathochromic shift (~30 nm) of the $S_{11}$ optical transitions. This points toward strong van der Waals interactions between individual s-SWCNTs and suggests that nanotube bundles are present even in solution. Note that the peak at approximately 1,930 nm corresponds to imperfect background subtraction of absorption due to the NMP solvent. The s-SWCNT dispersion in NMP does not yield measureable luminescence, despite the low m-SWCNT content of <0.1%, potentially due to inter-tube interactions within bundles and/or excitonic screening effects induced by the high-dielectric solvent.

Figure 17D:
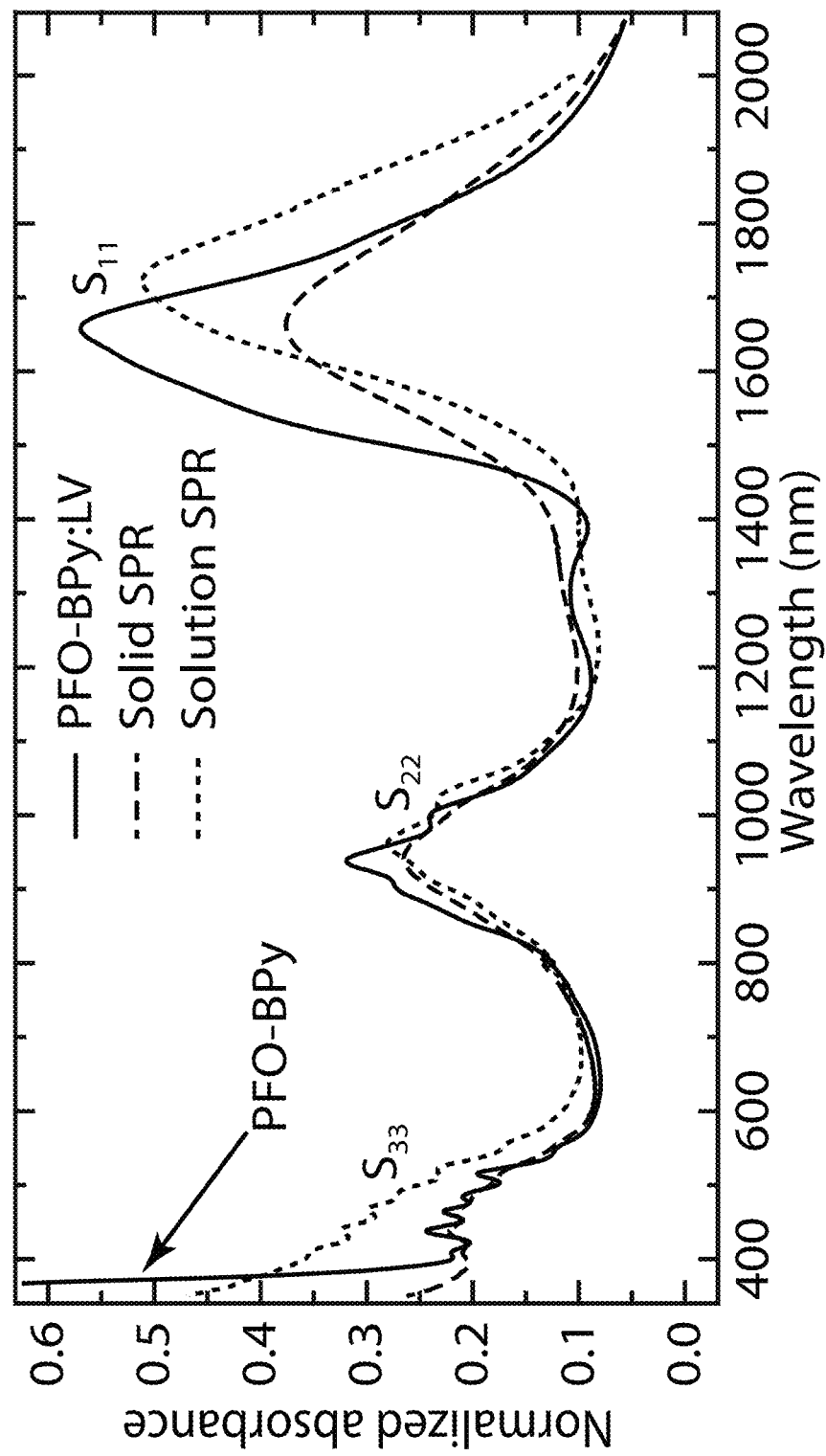

FIG. 17(d) shows the absorbance spectra, normalized to the area under the $S_{22}$ optical transition envelope, of the s-SWCNT networks prepared by ultrasonic spray deposition (and subsequent post-deposition solvent treatment to remove excess PFO-BPy or fully remove SP). In comparison to the inks, the $S_{11}$ and $S_{22}$ optical transition envelopes of the PFO-BPy:LV and Solid SPR samples are broadened, indicating stronger interactions between individual s-SW-CNTs, although only a small (~20 nm) bathochromic shift is observed. The s-SWCNT network prepared from the NMP dispersion (Solution SPR) also exhibits broadened optical transition envelopes compared to the corresponding ink, but in this case the transitions also exhibit sizeable bathochromic shifts of approximately 20 meV, suggesting that further bundling occurs during the film deposition or formation steps. FIG. 17(d) demonstrates that the polymer was successfully removed in the Solid SPR sample, as evidenced by the decrease in optical density in the polymer absorbance region (400-500 nm).

Figure 17E:
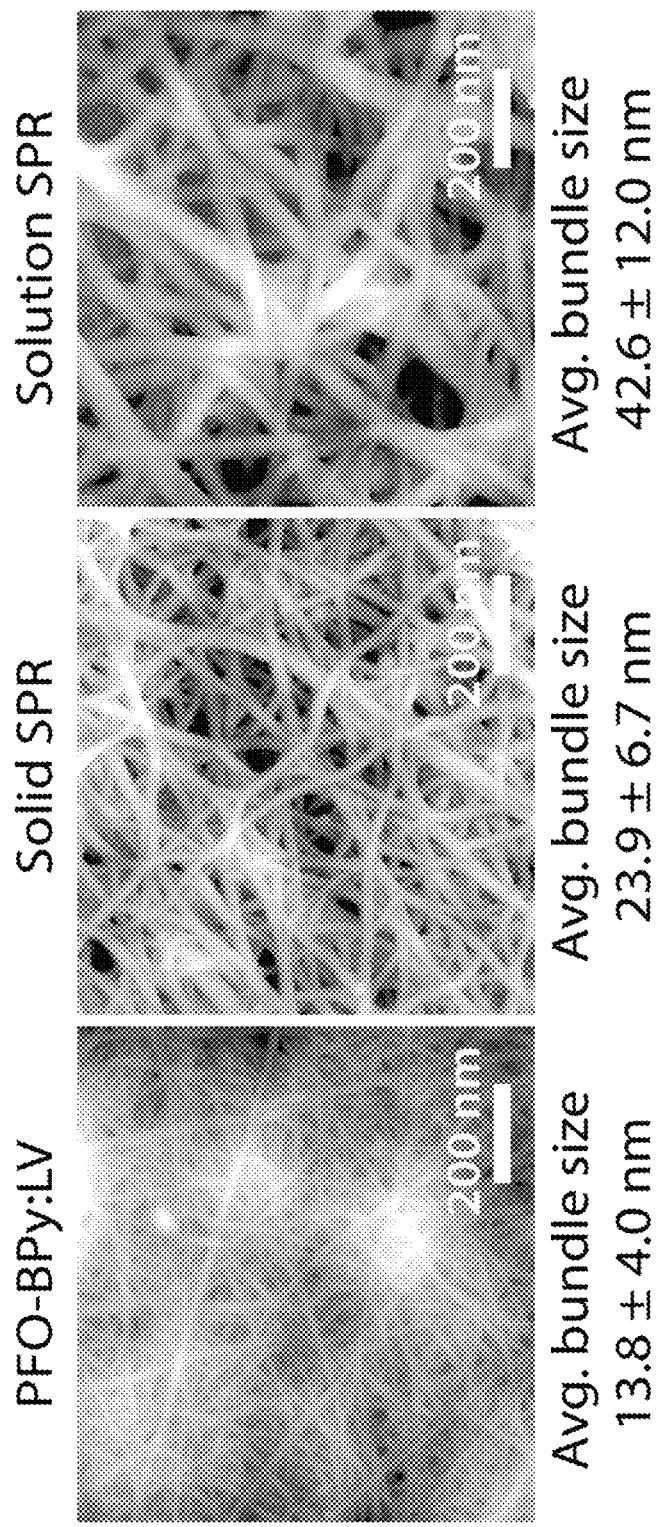
Figure 17F:
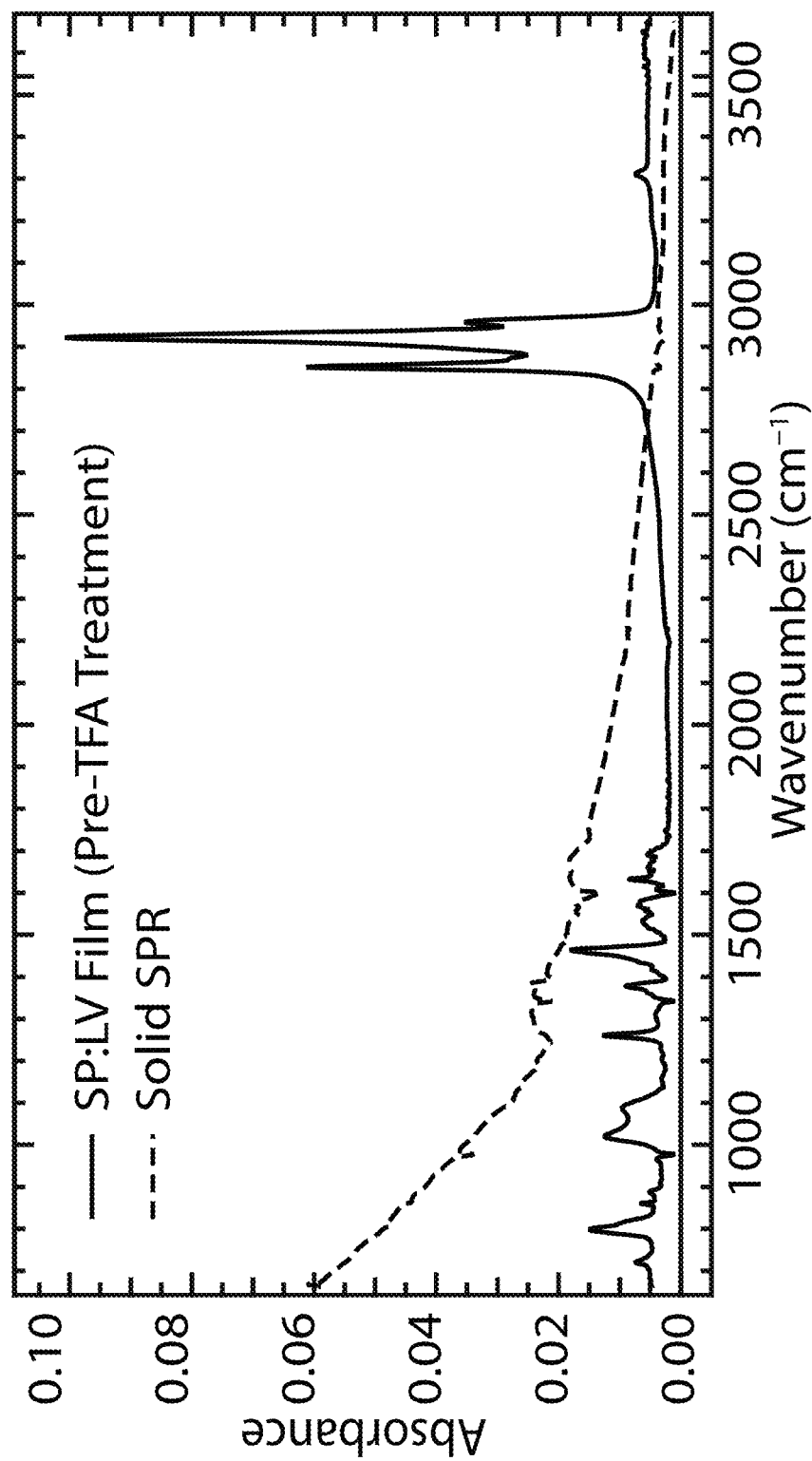
Figure 18:
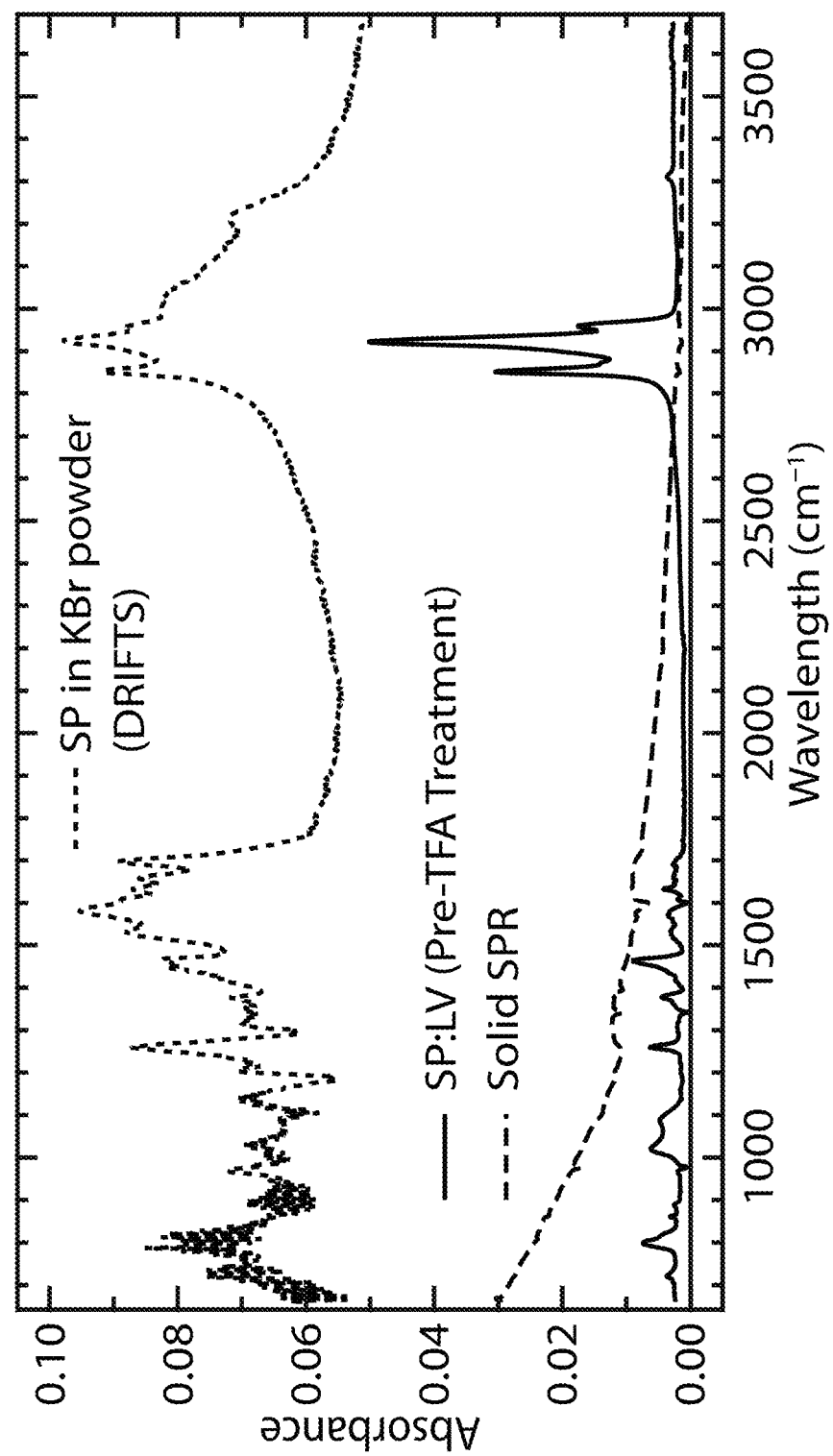
FIG. 18 shows a Fourier-transform infrared (FTIR) absorption spectrum of an s-SWCNT network.

FIG. 17(e) shows atomic force microscopy (AFM) surface topography images of the three s-SWCNT networks. FIG. 17(e) shows that the largest bundles (approximately 43 nm in diameter) are present in the Solution SPR sample, consistent with the large bathochromic shift observed upon film deposition. The AFM images of the PFO-BPy:LV and Solid SPR samples do not indicate the presence of individual s-SWCNTs (either polymer-wrapped or bare), but reveal nanotube bundles on the order of 14 nm and 24 nm in diameter, respectively. This suggests that solvent evaporation during film deposition drives s-SWCNT bundle formation. However, retaining the SP during film formation helps to limit the extent of bundling, resulting in substantially smaller bundles than found when the SP is removed prior to network deposition. As shown in FIG. 17(f), a Fourier-transform infrared (FTIR) absorption spectrum of the sample prepared from the SP:LV dispersion prior to TFA treatment exhibit absorption bands due to vibrational modes characteristic of the SP, as shown in FIG. 18). Treatment of this film with TFA appears to result in complete removal of the SP from the LV SWCNT network, since the absorption peaks are absent from the FTIR spectrum.

The three samples displayed in FIGS. 17(a)-17(f) exhibit large variations in both the extent of residual polymer within each s-SWCNT network and the resulting network morphology. To probe the effects of these changes on carrier transport and TE performance, the s-SWCNT networks were doped with OA, where the doping level was controlled by the methods discussed above. FIGS. 19(a) and 19(b) show the thermopower α and the TE power factor $\alpha^2\sigma$ versus the electrical conductivity σ, respectively. The dependence of the TE power factor $\alpha^2\sigma$ on the electrical conductivity σ shown in FIG. 19(b) indicates some effects of the polymer in transport and the effects of bundling. First, in comparing the PFO-BPy:LV sample to the Solution SPR sample, a similar trend in the TE power factor $\alpha^2\sigma$ versus the electrical conductivity σ emerges, as well as a similar peak TE power factor $\alpha^2\sigma$ (approximately 140-150 $\mu W/m \cdot K^2$). This trend holds until high doping levels, where the two datasets deviate. The Solution PR TE power factor $\alpha^2\sigma$ sharply decreases after the peak, predominantly due to the limited peak electrical conductivity σ in the s-SWCNT network. This rapid decline can be attributed to this film's inability to be doped to high levels efficiently. Second, and most dramatically, the peak TE power factor $\alpha^2\sigma$ of approximately 350 $W/m \cdot K^2$ for the Solid SPR film more than doubles that of the other two films, placing the performance of the approximately 1.3 nm diameter LV s-SWCNT networks in the same range as high-performance semiconducting polymers, such as PEDOT:PSS.

Figure 20A:
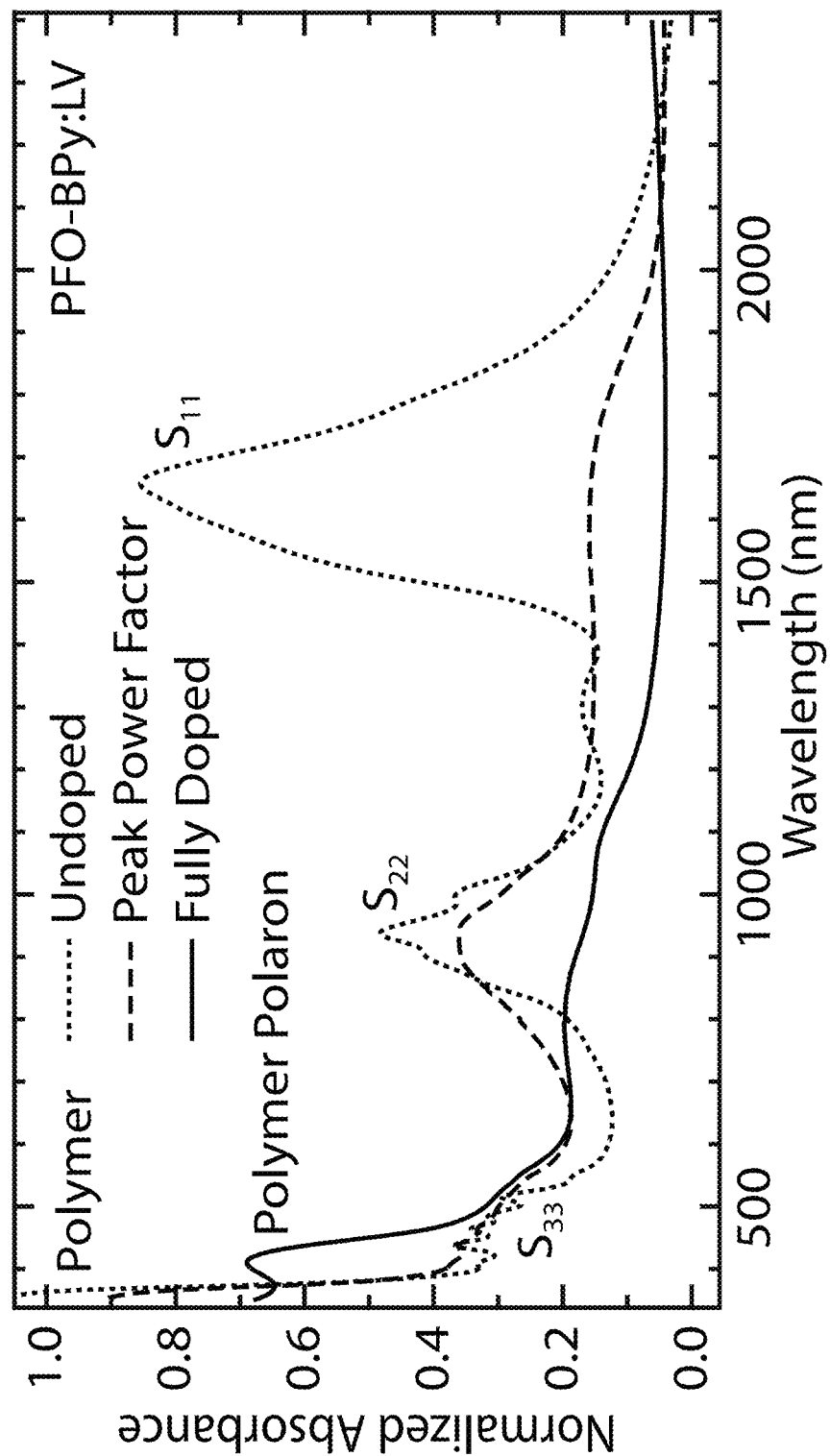

The absorption spectra of the doped s-SWCNT networks shown in FIGS. 20(a)-3(c) may be analyzed as a function of OA doping level. As discussed above, the extent to which the exciton transitions are quenched is proportional to the hole density injected into the occupied electronic states of the s-SWCNTs, as expected from the phase space filling effect for an excitonic semiconductor. This correlation allows for the extent of absorption bleaching to serve as a comparative measure of the relative carrier density within each s-SWCNT network at a given electrical conductivity σ. This relationship is useful, since a number of assumptions may be made to correlate the extent of bleaching quantitatively with s-SWCNT carrier density, especially for polydisperse samples with multiple s-SWCNT species.

Figure 20B:
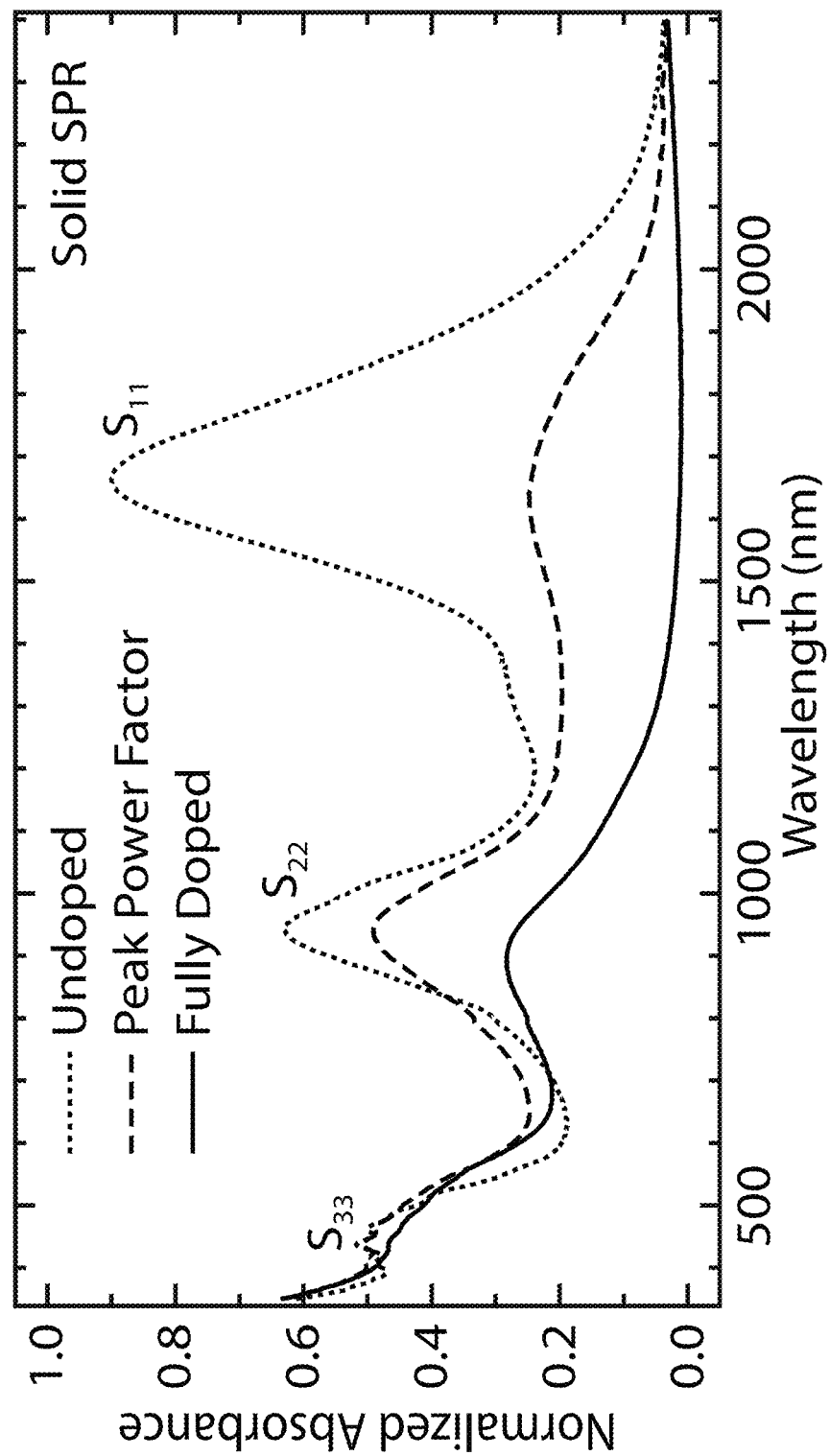
Figure 21B:
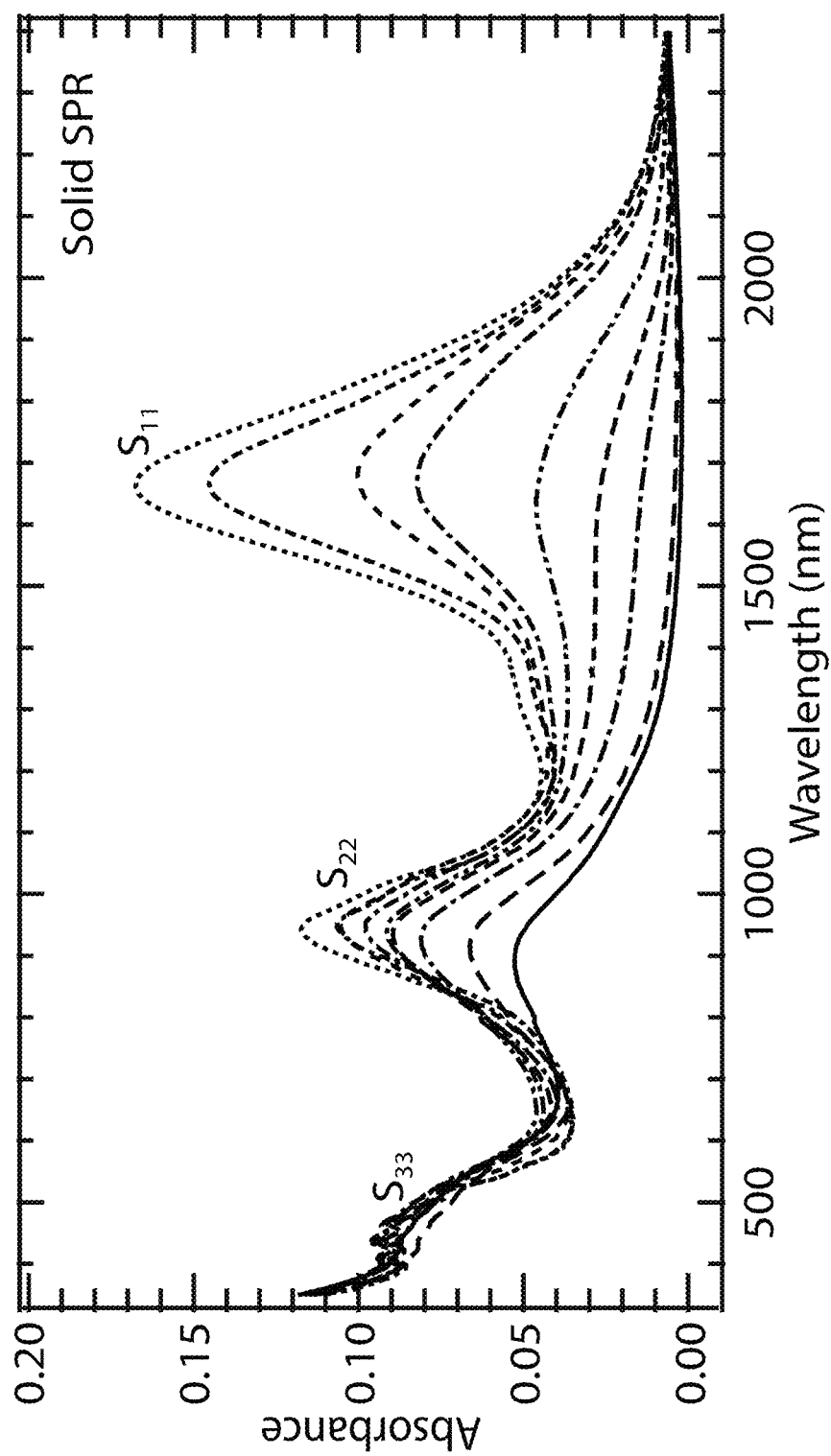
Figure 21C:
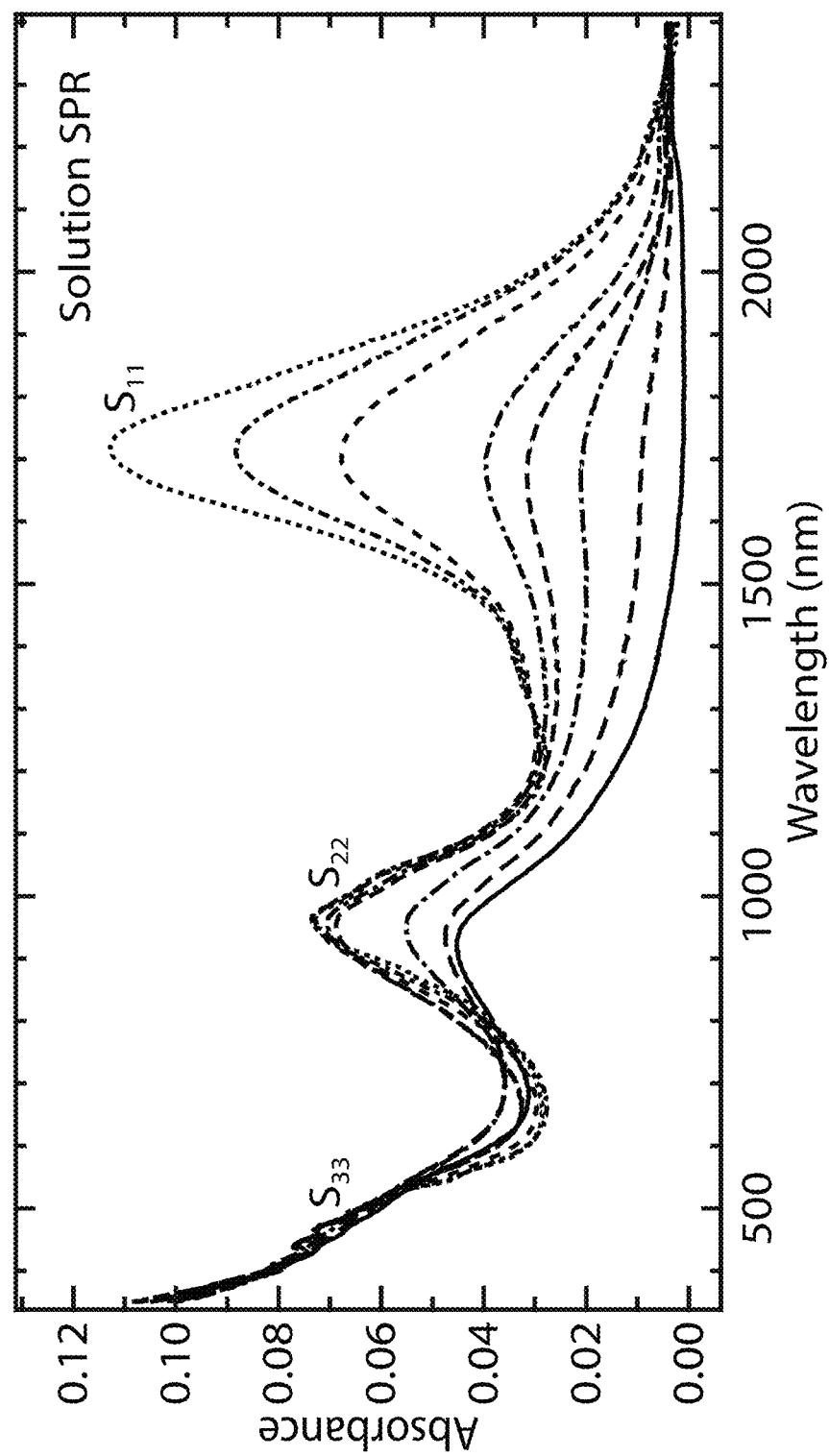

FIGS. 20(a)-20(c) show the qualitative impact of increasing carrier density on the absorbance spectra of the three samples. FIGS. 21(a)-21(c) show a more complete series of absorbance spectra, at doping levels spanning the entire range of absorption bleaching levels and corresponding to several orders of magnitude in electrical conductivity, for the three samples shown in FIGS. 20(a)-20(c). As shown in FIGS. 21(a)-21(c), in all cases, low doping levels result in bleaching of the $S_{11}$ envelope, followed by bleaching of the $S_{22}$ envelope at increasing carrier densities. When the networks are fully doped, the $S_{11}$ absorption envelope is completely bleached, and the $S_{22}$ absorption envelope is partially bleached. As shown in FIG. 20(a), for the PFO-BPy:LV sample, high doping levels result in formation of positive polarons on the PFO-BPy chains, as evidenced by the appearance of a new spectral feature at approximately 400 nm.

Figure 20D:
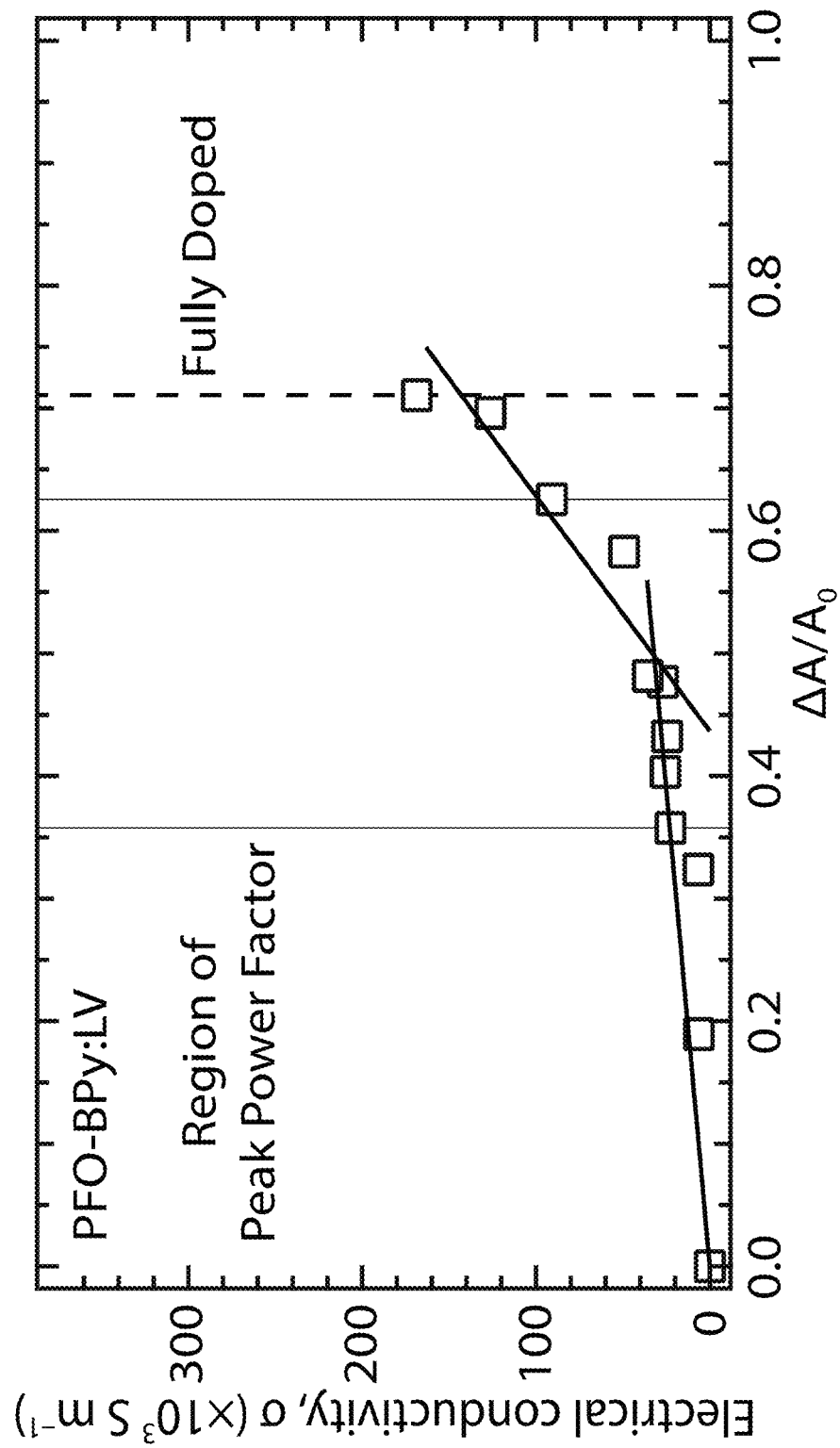
Figure 20E:
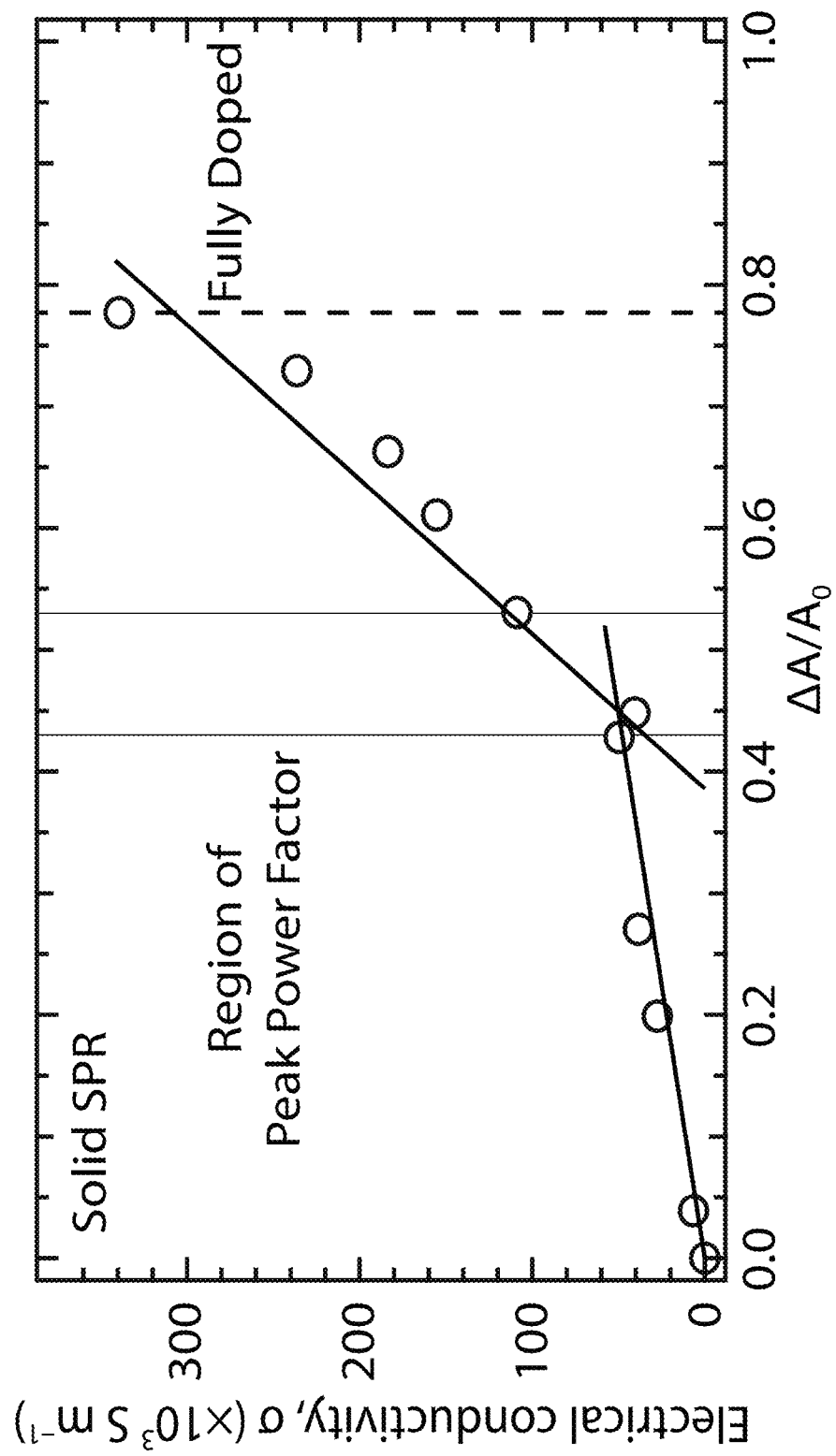
Figure 20F:
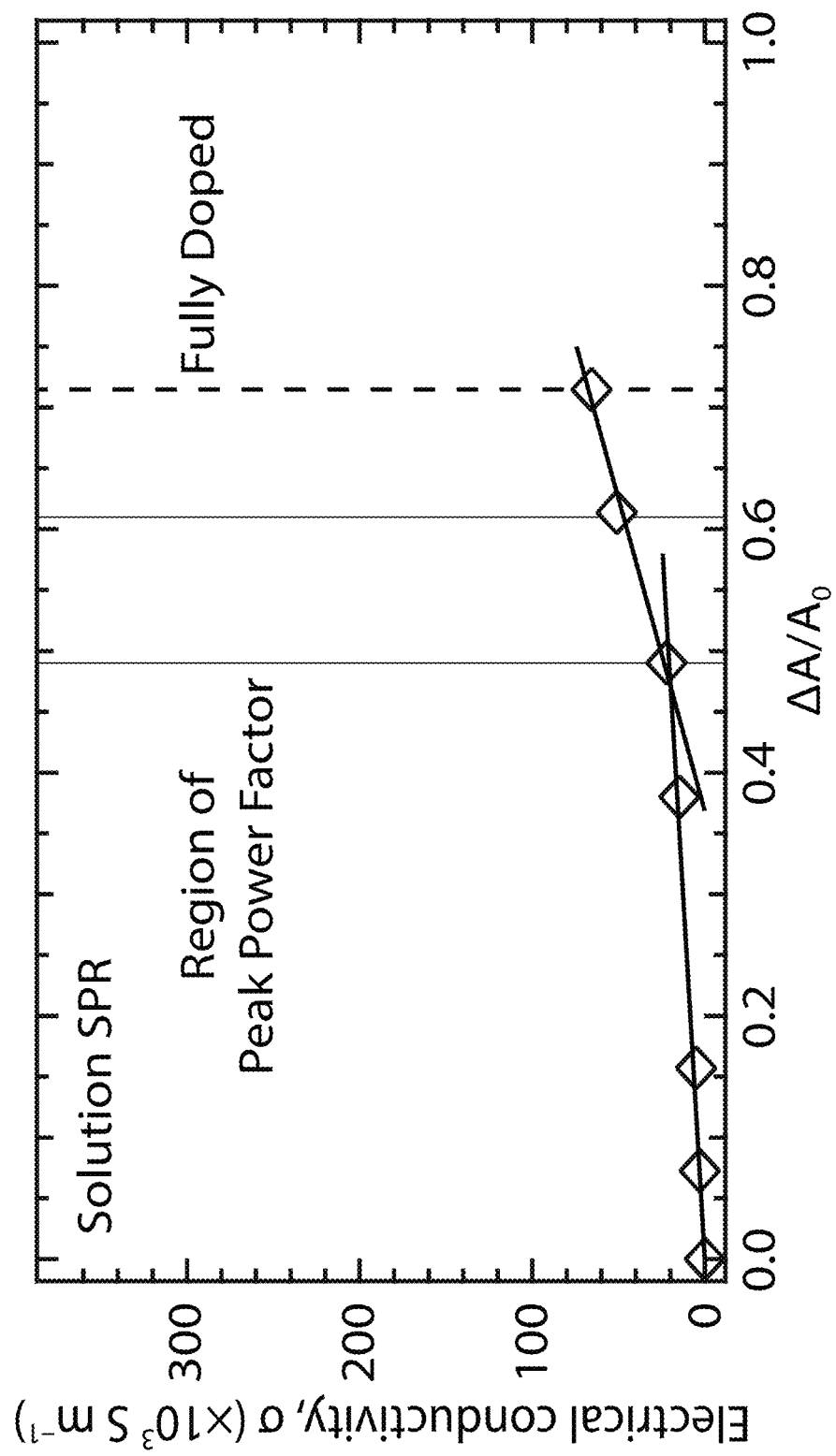

FIGS. 20(d)-20(f) show the electrical conductivity σ of the s-SWCNT networks as a function of the fractional bleach ($\Delta A/A_0$) of the $S_{11}$ and $S_{22}$ absorption envelopes. $A_0$ corresponds to the integrated area under the absorption spectra spanning both the $S_{11}$ and $S_{22}$ absorption envelopes. In this example, the spectral range was chosen to be approximately 650 nm to approximately 2400 nm. ΔA corresponds to the doping-induced change in the integrated area over the same spectral range. As shown in FIG. 20(d), for the PFO-BPy:LV network, the maximum conductivity σ (approximately 170,000 S/m) occurs when the $S_{11}$ and $S_{22}$ absorption envelopes are bleached approximately 71%. As shown in FIG. 20(e), when the SP is removed after deposition of the s-SWCNT network, the dopant is capable of inducing a larger bleach of the absorption bands (approximately 78%) and the maximum conductivity σ is doubled to approximately 340,000 S/m. In contrast, as shown in FIG. 20(f), when the SP is removed in solution prior to network deposition, the maximum conductivity σ only reaches approximately 65,000 S/m and the $S_{11}$ and $S_{22}$ absorption envelopes are bleached approximately 71%.

The differences observed in FIGS. 20(a)-20(f) may be explained by considering the correlation between $\Delta A/A_0$ and the hole density, as well as the necessity for OA molecules to interact directly with the s-SWCNT it-electron system to effectively inject this hole density. Since all of the samples reach their maximum electrical conductivity σ between 70-80% bleaching of the $S_{11}$ and $S_{22}$ absorption envelopes, this suggests that the hole densities are fairly similar when the samples are fully doped. However, the slightly larger extent of bleaching for the Solid SPR can be rationalized if one considers that the charge carrier doping occurs by interaction of the dopant molecules with the SWCNT surface. For the PFO-BPy:LV sample, the PFO-BPy polymer partially restricts access of the dopant molecules to the SWCNT surface, whereas the excessive bundling observed for the network prepared from the LV dispersion in NMP also results in a significant reduction in the available SWCNT surface area, despite the absence of a wrapping polymer. These two effects result in a slight reduction in the fractional bleaching level when the PFO-BPy:LV and Solution SPR samples reach their maximum doping level.

In all cases, the electrical conductivity data in FIGS. 20(d)-20(f) have two regimes: at low doping levels the electrical conductivity σ is weakly dependent on $\Delta A/A_0$, followed by a transition to a region where the electrical conductivity σ rapidly increases with $\Delta A/A_0$ up to the maximum electrical conductivity σ at full doping. The electrical conductivity σ is the product of the carrier density n and the mobility μ according to σ=neμ, where e is the charge on an electron. Since $\Delta A/A_0$ is proportional to the carrier density n, the slopes of these two regimes provide an indication of the charge carrier mobility in the s-SWCNT networks. This is similar to the general methodology for extracting field-effect mobilities from FET transfer curves. In that case, the gate voltage is proportional to charge carrier density and the mobility is estimated using the slope of the source-drain current versus gate voltage. The Solid SPR sample exhibits the largest slopes (for both regimes), suggesting that removing the wrapping polymer after network deposition reduces the barriers to carrier transport and results in high carrier mobility. The Solution SPR sample exhibits the smallest slopes, indicating that removal of the wrapping polymer before network deposition is not sufficient to maintain a large carrier mobility. In this case, the junction resistance between SWCNT bundles has been shown to increase with bundle size, suggesting that any potential mobility improvements attained by removing the polymer in the Solution-SPR sample are negated by the dramatically larger bundle sizes in this sample. These observations suggest that a network consisting of small bundles of SWCNTs that are free of wrapping polymer is the optimum morphology for highly-conductive SWCNT films.

The trends shown in FIGS. 20(a)-20(f) provide information regarding the differences in the TE properties shown in FIGS. 19(a) and 19(b). The enhanced performance for the Solid SPR sample arises primarily from two effects. First, the electrical conductivity measurements shown in FIGS. 20(d)-20(f) demonstrate that residual polymer within these films is essentially an inert filler, although its presence presumably blocks certain areas of tube/bundle surfaces from being directly accessible to dopant adsorption. Thus, removing this polymer generates networks comprised solely of the active s-SWCNT transport phase, and allows for better surface accessibility, and hence doping efficiency, of the OA molecules. Second, removing the polymer in the solid state (after network deposition) appears to increase the charge carrier mobility within the s-SWCNT network, relative to a control sample containing residual PFO-BPy in a roughly 1:1 mass ratio with the SWCNTs. Third, removing the SP in the solid-state, as opposed to solution-phase removal (before network deposition), enables the retention of small bundle size in the final network, similar to (but slightly larger than) the bundle size within the PFOBPy:LV network. The larger bundle size of the Solution SPR networks reduces the mobility, which in turn limits the ultimate conductivity σ of these networks. Since the carrier concentration of the fully doped Solution SPR network is only slightly smaller than that of the fully doped Solid SPR network, the dramatically lower maximum conductivity σ of the Solution SPR sample (64,000 S/m versus 340,000 S/m for the Solution SPR sample) is a direct result of this reduced mobility. Ultimately, the increased surface area associated with the small bundles of the Solid SPR network (relative to the Solution SPR network) and the better accessibility of dopant to SWCNT/bundle surfaces and higher carrier mobility (relative to the PFOBPy:LV network) accounts for the ability of the Solid SPR network to achieve extremely high electrical conductivities a that reach approximately 340,000 S/m.

Accordingly, improving the charge carrier mobility generates large improvements in the attainable TE power factor $\alpha^2\sigma$. This conclusion can be understood by considering the dependencies of the conductivity σ and thermopower α on the carrier density n. While the conductivity σ is directly proportional to carrier density n, the thermopower α is inversely proportional to the carrier density n:

$$\alpha = \frac{8\pi^2 k_B^2}{3eh^2} m^* T \left(\frac{\pi}{3n}\right)^{2/3} \quad (7)$$

where $k_B$ is the Boltzmann constant, e is the elementary charge, h is the Planck constant, m* is the charge carrier effective mass, T is the absolute temperature, and n is the charge carrier density.

A higher hole mobility implies that a given conductivity σ can be reached at a lower carrier density n. In turn, Equation (7) implies that at a given conductivity σ, the s-SWCNT thin film with the highest hole mobility will also have the highest thermopower α. FIGS. 20(a)-20(f) provide a way to visualize this effect for any series of s-SWCNT thin films, and Table 2 summarizes key metrics from this absorption analysis that can be used to screen the effects of a given change on the expected s-SWCNT TE performance. The regions between the solid vertical lines in FIGS. 20(d)-20(f) indicate the doping levels at which the maximum TE power factor $\alpha^2\sigma$ is observed for each sample. The magnitude of the maximum TE power factor $\alpha^2\sigma$ for this series of samples is inversely proportional to the $\Delta A/A_0$ at which this TE power factor $\alpha^2\sigma$ occurs, implying lower carrier density for better-performing samples. Also, as discussed above, the maximum attainable conductivity and the slope of the conductivity σ versus $\Delta A/A_0$ both correlate linearly to the maximum TE power factor $\alpha^2\sigma$. Ultimately, as demonstrated here for the Solid SPR sample, higher carrier mobility essentially shifts the thermopower $\alpha$ vs. conductivity $\sigma$ curve shown in FIG. 19(a) up and to the right, translating directly to a dramatic increase in the achievable TE power factor $\alpha^2\sigma$.

TABLE 2

Transport Properties of Doped LV s-SWCNT Thin Film Networks

| Sample | Maximum $\sigma$ [S/m] | Maximum $\Delta A/A_0$ | Transition $\Delta A/A_0$ | Slope1 [S/m] | Slope2 [S/m] | Peak $\alpha^2 \sigma$ [μW/m · K$^2$] |
|---|---|---|---|---|---|---|
| PFO-BPy:LV | 169,000 | 0.71 | 0.48-0.58 | 64,000 | 521,000 | 152 |
| Solid SPR | 339,000 | 0.78 | 0.43-0.53 | 112,000 | 787,000 | 349 |
| Solution SPR | 69,000 | 0.71 | 0.49-0.61 | 42,000 | 195,000 | 139 |

Accordingly, to achieve a highly conductive s-SWCNT network from a polymer-enriched dispersion, exemplary embodiments of the invention may limit the level of nanotube bundling in the s-SWCNT network and eliminate as much of the insulating (wrapped) polymer as possible. The use of a removable SP for s-SWCNT enrichment, and its subsequent dissolution after thin-film deposition, produce dramatic improvements in the TE performance of the s-SW-CNT networks. These advances push the performance of the approximately 1.3 nm diameter LV networks into the same range recently demonstrated for both HiPCO s-SWCNTs (<d>≈1.1 nm, with residual polyfluorene) and high-performance PEDOT-based organic thermoelectrics. These methods may also be applied to s-SWCNTs with diameters in the range of 1-1.1 nm, which can produce TE power factors $\alpha^2\sigma$ of approximately 350 μW/m·K$^2$, even at a polymer:SWCNT mass ratio of approximately 1:1.

Based on the above, exemplary embodiments of the present invention provide methods for determining desired doping conditions for an s-SWCNT network. The method may begin by spray depositing an s-SWCNT film as discussed above. The film may be treated to remove excess polymer from the film surface, and/or to remove the degradable wrapping polymer from the film. The thickness d of the film may then be measured by any suitable method, such as AFM or stylus profilometry of a scratch or masked edge of the film. In addition, an absorption spectrum of the undoped film may be measured.

A sample of the film may then be fully doped by immersing the film in a concentrated solution (greater than 1 mg/mL) of a charge-transfer dopant for at least approximately 1 minute at approximately 78° C., followed by subsequent de-doping by immersing the film in a suitable solvent at an appropriate temperature and time of immersion. Alternatively, a sample of the film may be incrementally doped by sequential immersion in solutions having increasing concentrations (such as between 1 ng/mL and 1 mg/mL) of the charge-transfer dopant in a suitable solvent. Once the sample has been doped, the absorption spectrum, sheet resistance $R_{sh}$, and thermopower $\alpha$ may be measured. The sheet resistance $R_{sh}$ may be measured by any suitable method, such as linear 4-point probe resistivity, 4-point probe resistivity in the van der Pauw geometry, or 2-point probe resistivity. The absorption spectrum and thermopower $\alpha$ may be measured by the methods discussed above.

The doping of the sample may be performed under different doping conditions, such as dopant concentration, immersion time, and/or temperature. As discussed in further detail below, this provides data at multiple doping levels that can be used to generate plots to assist in determining doping conditions that result in a desired doping level of the s-SWCNT network.

In one example, the absorption spectrum is integrated over a suitable range to determine the area $A_i$ under the absorption spectrum. The range may include the first ($S_{11}$) excitonic absorption peak envelope, or the first ($S_{11}$) and second ($S_{22}$) excitonic absorption peak envelopes. Preferably, the range does not include other spectral features that are not associated with the s-SWCNT, as including the other spectral features could result in an incorrect fractional bleach of the absorption spectrum. The fractional bleach due to charge carrier doping is then determined according to:

$$\frac{\Delta A}{A_o} = \frac{A_o - A_i}{A_o} \quad (8)$$

where $A_0$ is the area under the absorption spectrum of the undoped film, $A_i$ is the area under the absorption spectrum of the film at a specific doping level, and $\Delta A$ is the change in the area between the undoped and doped film.

The sheet resistance $R_{sh}$ may be converted to electrical conductivity $\sigma$ according to:

$$\sigma = \frac{1}{R_{sh} \times d} \quad (9)$$

The TE power factor may then be calculated as $\alpha^2\sigma$.

Figure 20H:
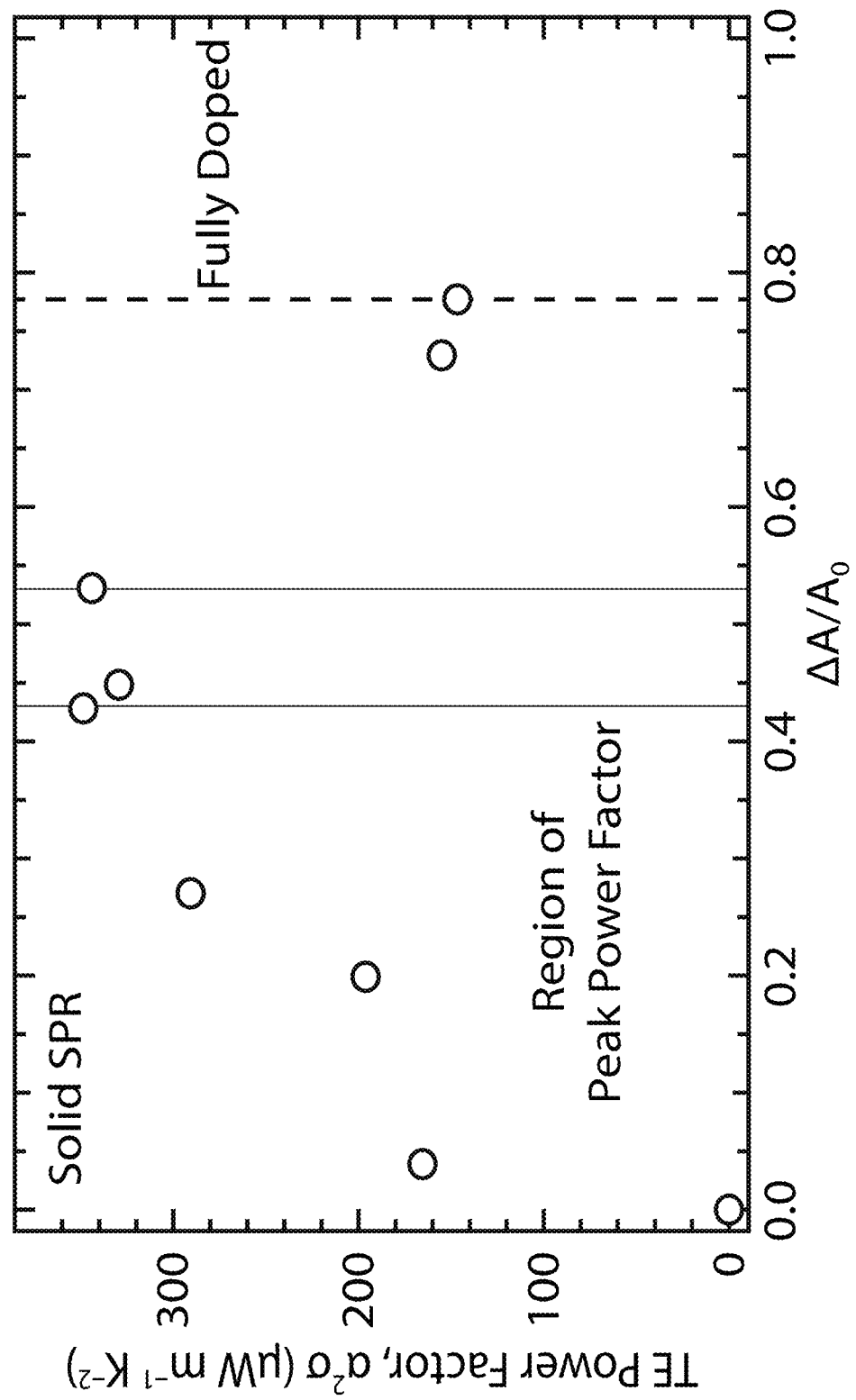
Figure 20I:
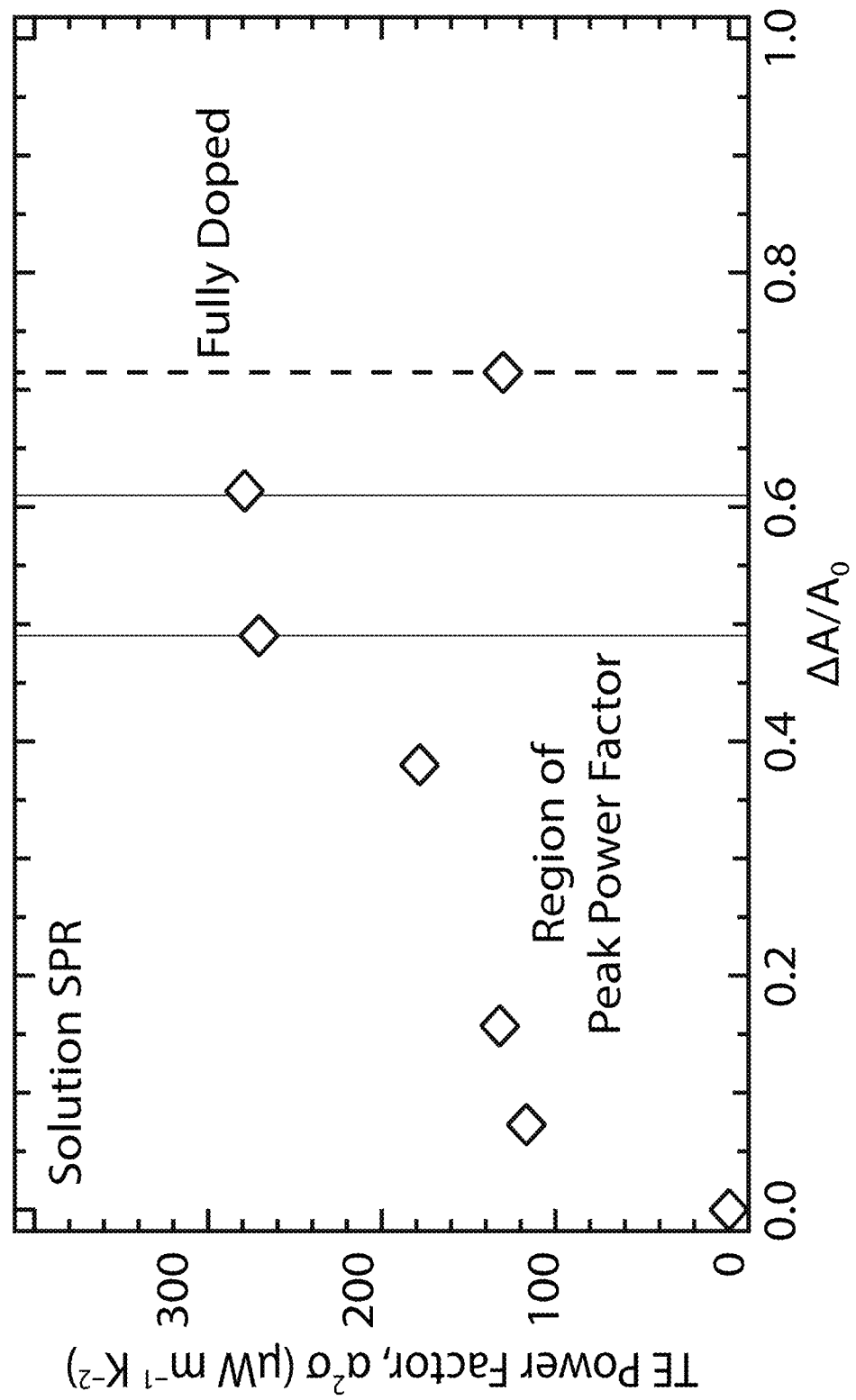

As shown in FIGS. 20(g)-20(i), the TE power factor $\alpha^2\sigma$ may be graphed as a function of the fractional bleach of the absorption spectrum $\Delta A/A_0$. FIG. 20(g) shows a plot of the TE power factor $\alpha^2\sigma$ as a function of the fractional bleach of the absorption spectrum $\Delta A/A_0$ for a PFO-BPy:LV sample with residual PFO-BPy in the LV s-SWCNT network (at an approximately 1:1 mass ratio), whereas FIGS. 20(h) and 20(i) show similar plots of s-SWCNT networks where the polymer has been completely removed after (Solid SPR sample) or before (Solution SPR sample) network formation, respectively.

The fractional bleach of the absorption spectrum $\Delta A/A_0$ may serve as a proxy for the doping level of the s-SWCNT network. Accordingly, as shown in FIGS. 20(g)-20(i), the range of optimum doping may be defined by the fractional bleach of the absorption spectrum $\Delta A/A_0$ that results in a desired TE power factor $\alpha^2\sigma$ for the s-SWCNT network, which may be the peak TE power factor $\alpha^2\sigma$. The desired TE power factor $\alpha^2\sigma$ may be a single TE power factor $\alpha^2\sigma$, or a range of TE power factors $\alpha^2\sigma$ over a corresponding range of fractional bleach values $\Delta A/A_0$, as indicated by the two solid vertical lines. As shown in FIGS. 20(d)-20(f), this may occur close to the transition between the two conductivity regimes in a plot of electrical conductivity σ as a function of the fractional bleach of the absorption spectrum $\Delta A/A_0$. The range of optimal doping corresponds to the doping conditions for which the desired TE power factor $\alpha^2\sigma$ was obtained. Once the range of optimal doping has been determined, samples of s-SWCNT networks may be prepared to obtain the desired TE power factor $\alpha^2\sigma$ by using the corresponding doping conditions.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for estimating the maximum thermoelectric (TE) power factor for a semiconducting single-walled carbon nanotube (s-SWCNT) network, the method comprising, in order:
   determining an undoped absorption value ($A_0$) by:
      measuring a first absorption spectrum for the s-SWCNT network in an undoped state;
      determining the location of at least one of a first excitonic peak envelope ($S_{11}$) or a second excitonic peak envelope ($S_{22}$) in the first absorption spectrum; and
      integrating the first absorption spectrum between a range that includes at least one of $S_{11}$ or $S_{22}$ to obtain $A_0$;
   determining a doped absorption value ($A_i$) by:
      measuring a second absorption spectrum for the s-SWCNT network for at least three different doping levels;
      integrating the second absorption spectrum for each of the doping levels between the range to obtain at least three values for $A_i$; and
      measuring an electrical conductivity for each of the doping levels;
   calculating for each of the doping levels:
      a difference of $A_0-A_i$; and
      a fractional bleach value defined as $(A_0-A_i)/A_0$;
   creating a plot of the electrical conductivity versus the fractional bleach value for each of the doping levels; and
   determining a transition fractional bleach value corresponding to a change in slope of the plot, wherein:
   the transition fractional bleach value corresponds to an optimum doping level for providing the maximum TE power factor.

2. The method according to claim 1, wherein the at least three doping levels are achieved by:
   immersing the s-SWCNT network in a solution comprising a charge-transfer dopant until a charge carrier doping level of the s-SWCNT network is saturated; and
   subsequently reducing the charge carrier doping level of the s-SWCNT network.

3. The method according to claim 2, wherein the charge-transfer dopant comprises triethyloxonium hexachloroantimonate (OA).

4. The method according to claim 1, wherein the at least three doping levels are achieved by sequentially immersing the s-SWCNT network in solutions comprising increasing concentrations of a charge-transfer dopant.

5. The method according to claim 4, wherein the charge-transfer dopant comprises triethyloxonium hexachloroantimonate (OA).

6. The method according to claim 1, wherein the range is between 650 nm and 2400 nm, inclusively.

7. The method according to claim 1, wherein the s-SWCNT network comprises s-SWCNTs having a diameter between 0.8 nm and 1.8 nm, inclusively.

8. The method according to claim 1, wherein the transitional fractional bleach value is between 0.43 and 0.61, inclusively.

9. The method according to claim 1, wherein:
   the change in slope is at an intersection of a first line and a second line,
   the first line has a slope between 42,000 S/m and 112,000 S/m, inclusively, and
   the second line has a slope between 195,000 S/m and 787,000 S/m, inclusively.

10. The method according to claim 1, wherein the maximum TE power factor is between 139 $\mu W\ m^{-1}K^{-2}$ and 349 $\mu W\ m^{-1}K^{-2}$, inclusively.

* * * * *